US012626785B2

(12) United States Patent
Yamazaki et al.

(10) Patent No.: US 12,626,785 B2
(45) Date of Patent: *May 12, 2026

(54) METHODS AND SYSTEMS FOR QUANTUM COMPUTING ENABLED MOLECULAR AB INITIO SIMULATIONS

(71) Applicant: GOOD CHEMISTRY INC., Vancouver (CA)

(72) Inventors: Takeshi Yamazaki, Vancouver (CA); Arman Zaribafiyan, Vancouver (CA); Shunji Matsuura, Vancouver (CA); Rudolf Plesch, Vancouver (CA)

(73) Assignee: Good Chemistry Inc., Vancouver (CA)

( * ) Notice: Subject to any disclaimer, the term of this patent is extended or adjusted under 35 U.S.C. 154(b) by 1023 days.

This patent is subject to a terminal disclaimer.

(21) Appl. No.: 17/522,498

(22) Filed: Nov. 9, 2021

(65) Prior Publication Data

US 2022/0068439 A1    Mar. 3, 2022

Related U.S. Application Data

(63) Continuation of application No. PCT/CA2020/050641, filed on May 12, 2020.

(60) Provisional application No. 62/949,263, filed on Dec. 17, 2019, provisional application No. 62/847,141, filed on May 13, 2019.

(51) Int. Cl.
| | |
|---|---|
| *G16C 10/00* | (2019.01) |
| *G06J 1/00* | (2006.01) |
| *G06N 10/20* | (2022.01) |
| *G06N 10/60* | (2022.01) |
| *G06N 10/80* | (2022.01) |

(52) U.S. Cl.
CPC ............... *G16C 10/00* (2019.02); *G06J 1/00* (2013.01); *G06N 10/20* (2022.01); *G06N 10/60* (2022.01); *G06N 10/80* (2022.01)

(58) Field of Classification Search
CPC ...................................................... G16C 10/00
See application file for complete search history.

(56) References Cited

U.S. PATENT DOCUMENTS

| | | | |
|---|---|---|---|
| 6,811,771 | B1 | 11/2004 | Sugo et al. |
| 7,113,967 | B2 | 9/2006 | Cleve et al. |
| 7,135,701 | B2 | 11/2006 | Amin et al. |
| 7,234,144 | B2 | 6/2007 | Wilt et al. |
| 7,418,283 | B2 | 8/2008 | Amin et al. |
| 7,533,068 | B2 | 5/2009 | Maassen Van Den Brink et al. |
| 7,619,437 | B2 | 11/2009 | Thom et al. |
| 7,639,035 | B2 | 12/2009 | Berkley |
| 7,660,533 | B1 | 2/2010 | Meyers et al. |
| 7,898,282 | B2 | 3/2011 | Harris et al. |
| 7,984,012 | B2 | 7/2011 | Coury et al. |
| 8,008,942 | B2 | 8/2011 | Van Den Brink et al. |

| | | | |
|---|---|---|---|
| 8,126,649 | B2 | 2/2012 | Frasch et al. |
| 8,175,995 | B2 | 5/2012 | Amin |
| 8,195,596 | B2 | 6/2012 | Rose et al. |
| 8,195,726 | B2 | 6/2012 | Macready et al. |
| 8,219,605 | B2 | 7/2012 | Cowlishaw et al. |
| 8,230,432 | B2 | 7/2012 | Bryant et al. |
| 8,244,662 | B2 | 8/2012 | Coury et al. |
| 8,283,943 | B2 | 10/2012 | Van Den Brink et al. |
| 8,421,053 | B2 | 4/2013 | Bunyk et al. |
| 8,503,885 | B2 | 8/2013 | Meyers et al. |
| 8,655,828 | B2 | 2/2014 | Rose |
| 8,832,165 | B2 | 9/2014 | Allen et al. |
| 9,537,953 | B1 | 1/2017 | Dadashikelayeh et al. |
| 9,660,859 | B1 | 5/2017 | Dadashikelayeh et al. |
| 9,727,824 | B2 | 8/2017 | Rose et al. |
| 9,870,273 | B2 | 1/2018 | Dadashikelayeh et al. |
| 9,881,256 | B2 | 1/2018 | Hamze et al. |
| 10,044,638 | B2 | 8/2018 | Dadashikelayeh et al. |
| 10,152,358 | B2 | 12/2018 | Dadashikelayeh et al. |
| 10,223,084 | B1 | 3/2019 | Dunn |
| 10,339,466 | B1 | 7/2019 | Ding et al. |
| 10,484,479 | B2 | 11/2019 | Johnson et al. |
| 10,558,932 | B1 | 2/2020 | Neven et al. |
| 10,614,370 | B2 | 4/2020 | Johnson et al. |
| 10,713,582 | B2 | 7/2020 | Dadashikelayeh |
| 10,824,478 | B2 | 11/2020 | Dadashikelayeh et al. |
| 10,826,845 | B2 | 11/2020 | Dadashikelayeh et al. |
| 10,929,294 | B2 | 2/2021 | Brahm et al. |

(Continued)

FOREIGN PATENT DOCUMENTS

| | | |
|---|---|---|
| CA | 2840958 A1 | 1/2013 |
| CA | 2881033 A1 | 4/2015 |

(Continued)

OTHER PUBLICATIONS

Lanzagorta, M. et. al. "Hybrid quantum-classical computing with applications to computer graphics." ACM SIGGRAPH 2005 Courses (pp. 2-es) (2005) (Year: 2005).*

Li, Q. et. al. "A hybrid classical-quantum clustering algorithm based on quantum walks." Quantum Information Process 10, 13-26 (2011) (Year: 2011).*

Niklasson et al., "Fast method for quantum mechanical molecular dynamics." Physical Review B 86(17):174308 (2012) (Year: 2012).*

Moll et. al., "Optimizing qubit resources for quantum chemistry simulations in second quantization on quantum computer." Journal of Physics A: Mathematical and Theoretical 49(29):295301 (2016) (Year: 2016).*

Yamamoto Y. et. al. "Quantum Computing vs. Coherent Computing" New Generation Computing 30:327-356 (2012) (Year: 2012).*

(Continued)

*Primary Examiner* — G. Steven Vanni
*Assistant Examiner* — Francini Alvarenga Fonseca Lopez
(74) *Attorney, Agent, or Firm* — Fish & Richardson P.C.

(57) ABSTRACT

The present disclosure provides methods and systems for using a hybrid architecture of classical and non-classical (e.g., quantum) computing to compute the quantum mechanical energy and/or electronic structure of a chemical system, as well as to identify stable conformations of a chemical system (e.g., a molecule) and/or to perform an ab initio molecular dynamics calculation or simulation on the chemical system.

17 Claims, 21 Drawing Sheets

(56)                  References Cited

U.S. PATENT DOCUMENTS

| | | |
|---|---|---|
| 11,017,289 B2 | 5/2021 | Crawford et al. |
| 2003/0005068 A1 | 1/2003 | Nickel et al. |
| 2003/0121028 A1 | 6/2003 | Coury et al. |
| 2004/0254735 A1* | 12/2004 | Horn ..................... G16C 20/40 |
| | | 702/19 |
| 2004/0267916 A1 | 12/2004 | Chambliss et al. |
| 2005/0027458 A1 | 2/2005 | Merz, Jr. et al. |
| 2005/0182614 A1 | 8/2005 | Meredith |
| 2005/0187844 A1 | 8/2005 | Chalermkraivuth et al. |
| 2005/0250651 A1 | 11/2005 | Amin et al. |
| 2005/0273306 A1 | 12/2005 | Hilton et al. |
| 2006/0221978 A1 | 10/2006 | Venkatachalam |
| 2006/0225165 A1 | 10/2006 | Maassen Van Den Brink et al. |
| 2007/0180586 A1 | 8/2007 | Amin |
| 2007/0239366 A1 | 10/2007 | Hilton et al. |
| 2008/0059547 A1 | 3/2008 | Taylor |
| 2008/0186918 A1 | 8/2008 | Tinnakornsrisuphap et al. |
| 2008/0215850 A1 | 9/2008 | Berkley et al. |
| 2008/0218519 A1 | 9/2008 | Coury et al. |
| 2008/0262990 A1 | 10/2008 | Kapoor et al. |
| 2008/0313430 A1 | 12/2008 | Bunyk |
| 2009/0070402 A1 | 3/2009 | Rose et al. |
| 2009/0078932 A1 | 3/2009 | Amin |
| 2009/0164435 A1 | 6/2009 | Routt |
| 2009/0182542 A9* | 7/2009 | Hilton .................... G06N 10/00 |
| | | 703/11 |
| 2009/0306902 A1 | 12/2009 | Lemmen et al. |
| 2009/0325694 A1 | 12/2009 | Beckman et al. |
| 2010/0261481 A1 | 10/2010 | Resende et al. |
| 2010/0306142 A1 | 12/2010 | Amin |
| 2011/0231462 A1 | 9/2011 | Macready et al. |
| 2011/0238378 A1 | 9/2011 | Allen et al. |
| 2011/0238855 A1 | 9/2011 | Korsunsky et al. |
| 2011/0296229 A1 | 12/2011 | Cowlishaw et al. |
| 2012/0072579 A1 | 3/2012 | Teather |
| 2012/0084242 A1 | 4/2012 | Levin |
| 2012/0159506 A1 | 6/2012 | Barham et al. |
| 2012/0215821 A1 | 8/2012 | Macready et al. |
| 2012/0240185 A1 | 9/2012 | Kapoor et al. |
| 2012/0253926 A1 | 10/2012 | Chen et al. |
| 2012/0254586 A1 | 10/2012 | Amin et al. |
| 2012/0278374 A1 | 11/2012 | Cowlishaw et al. |
| 2012/0326720 A1 | 12/2012 | Gambetta et al. |
| 2013/0026183 A1 | 1/2013 | Foster |
| 2013/0144925 A1 | 6/2013 | Macready et al. |
| 2013/0263131 A1 | 10/2013 | Beda, III et al. |
| 2013/0308956 A1 | 11/2013 | Meyers et al. |
| 2013/0336472 A1 | 12/2013 | Fahlgren et al. |
| 2014/0025606 A1 | 1/2014 | Macready |
| 2014/0122702 A1 | 5/2014 | Jung et al. |
| 2014/0123325 A1 | 5/2014 | Jung et al. |
| 2014/0187427 A1 | 7/2014 | Macready et al. |
| 2014/0214257 A1 | 7/2014 | Williams et al. |
| 2014/0250288 A1 | 9/2014 | Roy |
| 2014/0258730 A1 | 9/2014 | Stecher |
| 2014/0324933 A1 | 10/2014 | Macready et al. |
| 2014/0337612 A1 | 11/2014 | Williams |
| 2014/0344322 A1 | 11/2014 | Ranjbar |
| 2014/0379924 A1 | 12/2014 | Das et al. |
| 2015/0006443 A1 | 1/2015 | Rose et al. |
| 2015/0032991 A1 | 1/2015 | Lanting et al. |
| 2015/0032993 A1 | 1/2015 | Amin et al. |
| 2015/0055961 A1 | 2/2015 | Meyers et al. |
| 2015/0111754 A1 | 4/2015 | Harris et al. |
| 2015/0120551 A1 | 4/2015 | Jung et al. |
| 2015/0120555 A1 | 4/2015 | Jung et al. |
| 2015/0142398 A1* | 5/2015 | Miller, III .............. G16C 10/00 |
| | | 703/2 |
| 2015/0169746 A1 | 6/2015 | Hatami-Hanza |
| 2015/0178349 A1 | 6/2015 | Niewodniczanski et al. |
| 2015/0193692 A1 | 7/2015 | Israel |
| 2015/0205759 A1 | 7/2015 | Israel et al. |
| 2015/0220852 A1 | 8/2015 | Hatami-Hanza |
| 2015/0227559 A1 | 8/2015 | Hatami-Hanza |
| 2015/0262074 A1 | 9/2015 | Bruestle et al. |

| | | |
|---|---|---|
| 2015/0269124 A1 | 9/2015 | Hamze et al. |
| 2015/0332994 A1 | 11/2015 | Mallik et al. |
| 2015/0349960 A1 | 12/2015 | Bagley |
| 2015/0358251 A1 | 12/2015 | Varga et al. |
| 2015/0363358 A1 | 12/2015 | Ronagh et al. |
| 2015/0363708 A1 | 12/2015 | Amin et al. |
| 2016/0026183 A1 | 1/2016 | Williams et al. |
| 2016/0071021 A1 | 3/2016 | Raymond |
| 2016/0132785 A1 | 5/2016 | Amin et al. |
| 2016/0162798 A1 | 6/2016 | Marandi et al. |
| 2016/0171368 A1 | 6/2016 | Aspuru-Guzik et al. |
| 2016/0224515 A1 | 8/2016 | Ronagh et al. |
| 2016/0321559 A1 | 11/2016 | Rose et al. |
| 2016/0328253 A1 | 11/2016 | Majumdar |
| 2016/0328659 A1 | 11/2016 | Mohseni et al. |
| 2016/0338075 A1 | 11/2016 | McKibben |
| 2016/0342891 A1 | 11/2016 | Ross et al. |
| 2017/0011305 A1 | 1/2017 | Williams |
| 2017/0017894 A1 | 1/2017 | Lanting et al. |
| 2017/0060642 A1 | 3/2017 | Castellano et al. |
| 2017/0147303 A1 | 5/2017 | Amy et al. |
| 2017/0147695 A1 | 5/2017 | Shih |
| 2017/0214701 A1 | 7/2017 | Hasan |
| 2017/0223143 A1 | 8/2017 | Johnson et al. |
| 2017/0242824 A1 | 8/2017 | Karimi et al. |
| 2017/0255592 A1 | 9/2017 | Karimi et al. |
| 2017/0255629 A1 | 9/2017 | Thom et al. |
| 2017/0255872 A1 | 9/2017 | Hamze et al. |
| 2017/0286852 A1 | 10/2017 | Rezaie et al. |
| 2017/0286858 A1 | 10/2017 | La Cour et al. |
| 2017/0300808 A1 | 10/2017 | Ronagh et al. |
| 2017/0323195 A1 | 11/2017 | Crawford et al. |
| 2017/0344898 A1 | 11/2017 | Karimi et al. |
| 2017/0351974 A1 | 12/2017 | Rose et al. |
| 2017/0372427 A1 | 12/2017 | Johnson et al. |
| 2017/0373940 A1 | 12/2017 | Shahab et al. |
| 2018/0014970 A1 | 1/2018 | Conde De Paiva et al. |
| 2018/0039903 A1 | 2/2018 | Mosca et al. |
| 2018/0091440 A1 | 3/2018 | Dadashikelayeh et al. |
| 2018/0096085 A1 | 4/2018 | Rubin |
| 2018/0107526 A1 | 4/2018 | Dadashikelayeh et al. |
| 2018/0114138 A1 | 4/2018 | Monroe et al. |
| 2018/0218279 A1 | 8/2018 | Lechner et al. |
| 2018/0218281 A1 | 8/2018 | Reinhardt et al. |
| 2018/0246851 A1 | 8/2018 | Zaribafiyan et al. |
| 2018/0260730 A1 | 9/2018 | Reagor et al. |
| 2018/0267937 A1 | 9/2018 | Pelc et al. |
| 2018/0308007 A1 | 10/2018 | Amin et al. |
| 2019/0009581 A1 | 1/2019 | Schalk et al. |
| 2019/0095811 A1 | 3/2019 | Antonio et al. |
| 2019/0205790 A1 | 7/2019 | Dukatz et al. |
| 2019/0378047 A1 | 12/2019 | Pistoia et al. |
| 2020/0005186 A1 | 1/2020 | Romero et al. |
| 2020/0057957 A1 | 2/2020 | Johnson et al. |
| 2020/0104740 A1 | 4/2020 | Cao |
| 2020/0143910 A1 | 5/2020 | Noori et al. |
| 2020/0272683 A1 | 8/2020 | Ronagh et al. |
| 2020/0272684 A1 | 8/2020 | Karimi et al. |
| 2020/0364597 A1 | 11/2020 | Friedlander et al. |
| 2020/0364601 A1* | 11/2020 | Yamazaki .............. G16C 20/90 |
| 2020/0410343 A1 | 12/2020 | Niu et al. |
| 2021/0166148 A1 | 6/2021 | Matsuura et al. |
| 2021/0374611 A1 | 12/2021 | Ronagh et al. |
| 2023/0080393 A1 | 3/2023 | Matsuura |

FOREIGN PATENT DOCUMENTS

| | | | |
|---|---|---|---|
| CA | 2902015 A1 | 1/2016 | |
| CA | 2921711 A1 | 8/2017 | |
| CA | 3026824 A1 | 12/2017 | |
| CN | 106874506 A | 6/2017 | |
| CN | 110069348 A | 7/2019 | |
| EP | 3113084 A1 | 1/2017 | |
| JP | 2004503011 A | 1/2004 | |
| JP | 2006061926 A | 3/2006 | |
| JP | 2008506203 A | 2/2008 | |
| JP | 2008525873 A | 7/2008 | |
| JP | 2010182106 A | 8/2010 | |
| JP | 2012083427 A | 4/2012 | |

(56) References Cited

FOREIGN PATENT DOCUMENTS

| JP | 2013114366 A | 6/2013 |
|----|----|----|
| JP | 7312173 B2 | 7/2023 |
| WO | WO-2005122052 A1 | 12/2005 |
| WO | WO-2006026985 A2 | 3/2006 |
| WO | WO-2007089674 A2 | 8/2007 |
| WO | WO-2010148120 A2 | 12/2010 |
| WO | WO-2014210368 A1 | 12/2014 |
| WO | WO-2015006494 A1 | 1/2015 |
| WO | WO-2015060915 A2 | 4/2015 |
| WO | WO-2015121619 A2 | 8/2015 |
| WO | WO-2016029172 A1 | 2/2016 |
| WO | WO-2017068228 A1 | 4/2017 |
| WO | WO-2017111937 A1 | 6/2017 |
| WO | WO-2017145086 A1 | 8/2017 |
| WO | WO-2017149491 A1 | 9/2017 |
| WO | WO-2017152289 A1 | 9/2017 |
| WO | WO-2017201626 A1 | 11/2017 |
| WO | WO-2017214717 A1 | 12/2017 |
| WO | WO-2018119522 A1 | 7/2018 |
| WO | WO-2018160599 A1 | 9/2018 |
| WO | WO-2019104440 A1 | 6/2019 |
| WO | WO-2019104443 A1 | 6/2019 |
| WO | WO-2019152020 A1 | 8/2019 |
| WO | WO-2019157228 A1 | 8/2019 |
| WO | WO-2019222748 A1 | 11/2019 |
| WO | WO-2019229527 A2 | 12/2019 |
| WO | WO-2019241879 A1 | 12/2019 |
| WO | WO-2019244105 A1 | 12/2019 |
| WO | WO-2020113339 A1 | 6/2020 |
| WO | WO-2020227825 A1 | 11/2020 |
| WO | WO-2020255076 A1 | 12/2020 |
| WO | WO-2021111368 A1 | 6/2021 |
| WO | WO-2021181281 A1 | 9/2021 |
| WO | WO-2021207847 A1 | 10/2021 |
| WO | WO-2021243454 A1 | 12/2021 |

OTHER PUBLICATIONS

Cao Y. et. al. "Potential of quantum computing for drug discovery" IBM Journal of Research and Development 62(6):6:1-6:20 (2018) (Year: 2018).*

Ibrahim et. al. "Cross-scale efficient tensor contractions for coupled cluster computations through multiple programming model backends" J. Parallel Distrib. Comput. 106:92-105 (2017) (Year: 2017).*

Oskin et. al. "A Practical Architecture for Reliable Quantum Computers" in Computer 35(1):79-87 (2002) (Year: 2002).*

Co-pending U.S. Appl. No. 18/046,320, inventor Matsuura; Shunji, filed Oct. 13, 2022.

U.S. Appl. No. 16/888,446 Office Action dated Jun. 9, 2022.

Yamazaki, et al. Towards the practical application of near-term quantum computers in quantum chemistry simulations: A problem decomposition approach. arXiv preprint arXiv:1806.01305 (2018).

Yang. Direct calculation of electron density in density-functional theory. Phys Rev Lett. Mar. 18, 1991;66(11):1438-1441. doi: 10.1103/PhysRevLett.66.1438.

Baiardi, et al. Expansive Quantum Mechanical Exploration of Chemical Reaction Paths. arXiv preprint arXiv:2112.04944 (2021). (24 pages).

Bernstein, et al. De novo exploration and self-guided learning of potential-energy surfaces. arXiv preprint arXiv:1905.10407 (2019). (11 pages).

Bisbo, et al. Efficient global structure optimization with a machine learned surrogate model. arXiv preprint arXiv:1907.05741 (2019). https://doi.org/10.48550/arXiv.1907.05741 (13 pages).

Corso, et al. Diffdock: Diffusion steps, twists, and turns for molecular docking. arXiv preprint arXiv:2210.01776 (2022). (29 pages).

Del Rio, et al. Local Bayesian optimizer for atomic structures. Physical Review B 100.10 (2019): 104103. https://doi.org/10.1103/PhysRevB.100.104103 (10 pages).

Dewyer, et al. Methods for exploring reaction space in molecular systems. Wiley Interdisciplinary Reviews: Computational Molecular Science 8.2 (2018): e1354. doi: 10.1002/wcms.1354 (20 pages).

Fedorov, et al. Coupled-cluster theory based upon the fragment molecular-orbital method. J Chem Phys. Oct. 1, 2005;123(13):134103. doi: 10.1063/1.2007588. (12 pages).

Fontalvo, J.R. Variational Quantum Information Processing. Doctoral dissertation, Harvard University. Graduate School of Arts & Sciences. Jan. 20, 2019. URL: https://dash.harvard.edu/bitstream/handle/1/42029810/ROMEROFONTALVO-DISSERTATION-2019.pdf?sequence=1&isAllowed=y (281 pages).

Gaussian, Inc. Changes Between Gaussian 16 and Gaussian 09. Last updated on: Jan. 5, 2017. Available online at: https://gaussian.com/gdiffs/ (3 pages).

Gómez-Bombarelli, et al. Automatic chemical design using a data-driven continuous representation of molecules. arXiv preprint arXiv:1610.02415 (2016). (23 pages).

Goldsmith, et al. Machine learning for heterogeneous catalyst design and discovery. AIChE J., (2018), 64: 2311-2323. https://doi.org/10.1002/aic.16198.

Grambow, et al. Reactants, products, and transition states of elementary chemical reactions based on quantum chemistry. Sci Data. May 8, 2020;7(1):137. doi: 10.1038/s41597-020-0460-4.

Hydrogen Bond. In The MacMillan encyclopedia (2nd ed.). Market House Books Ltd. Credo Reference. 2 pages. (Year: 2003).

Imamoglu, et al. Quantum information processing using quantum dot spins and cavity-QED. arXiv preprint quant-ph/9904096 (1999).

Kako, et al. Coherent Ising machines with error correction feedback. arXiv preprint arXiv:2005.10895 (2020).

Kato K. Simulation of Toner fixing Phenomena. Ricoh Technical Report, Ricoh Corporation. Sep. 25, 1997. No. 23. pp. 27-33 (English Abstract).

Keith, et al. Combining Machine Learning and Computational Chemistry for Predictive Insights Into Chemical Systems. Chem Rev. Aug. 25, 2021; 121(16): 9816-9872. Published online Jul. 7, 2021. doi: 10.1021/acs.chemrev.1c00107.

Kobayashi, et al. Extension of linear-scaling divide-and-conquer-based correlation method to coupled cluster theory with singles and doubles excitations. J Chem Phys. Jul. 28, 2008;129(4):044103. doi: 10.1063/1.2956490. (10 pages).

Koes, et al. Lessons learned in empirical scoring with smina from the CSAR 2011 benchmarking exercise. J Chem Inf Model. Aug. 26, 2013;53(8):1893-904. doi: 10.1021/ci300604z. Epub Feb. 12, 2013.

Komp, et al. Progress towards machine learning reaction rate constants. Phys Chem Chem Phys. Feb. 2, 2022;24(5):2692-2705. doi: 10.1039/d1cp04422b.

Lahey, et al. Simulating protein-ligand binding with neural network potentials. Chem Sci. Jan. 23, 2020;11(9):2362-2368. doi: 10.1039/c9sc06017k.

Li, et al. Structure-based de novo drug design using 3D deep generative models. Chem Sci. Sep. 9, 2021;12(41):13664-13675. doi: 10.1039/d1sc04444c. eCollection Oct. 27, 2021.

Mcnutt, et al. GNINA 1.0: molecular docking with deep learning. J Cheminform. Jun. 9, 2021;13(1):43. doi: 10.1186/s13321-021-00522-2. (20 pages).

Meldgaard, et al. Machine learning enhanced global optimization by clustering local environments to enable bundled atomic energies. arXiv preprint arXiv:1807.04605 (2018). (10 pages).

Meyer, et al. Machine Learning in Computational Chemistry: An Evaluation of Method Performance for Nudged Elastic Band Calculations. J Chem Theory Comput. Nov. 12, 2019;15(11):6513-6523. doi: 10.1021/acs.jctc.9b00708. Epub Oct. 9, 2019.

Nakayama S. Study on Numerical Gradient Estimation by Adiabatic Quantum Computation. Research Report Mathematical Modeling and Problem Solving (MPS). IPSJ SIG Technical Report. Sep. 26, 2013. vol. 2013-MPS-95 No. 10. pp. 1-6. (English Abstract).

Pattanaik, et al. Generating transition states of isomerization reactions with deep learning. Physical Chemistry Chemical Physics 22.41 (2020): 23618-23626.

PCT/IB2023/051819 International Search Report and Written Opinion dated May 19, 2023.

Peterson, A.A. Acceleration of saddle-point searches with machine learning. J Chem Phys. Aug. 21, 2016;145(7):074106. doi: 10.1063/1.4960708. (5 pages).

US 12,626,785 B2

(56) References Cited

OTHER PUBLICATIONS

Ragoza, et al. Generating 3D Molecules Conditional on Receptor Binding Sites with Deep Generative Models. arXiv preprint arXiv:2110. 15200 (2021). (16 pages).

Schneuing, et al. Structure-based drug design with equivariant diffusion models. arXiv preprint arXiv:2210.13695 (2022). (21 pages).

Schreiner, et al. NeuralNEB—Neural Networks can find Reaction Paths Fast. arXiv preprint arXiv:2207.09971 (2022). (13 pages).

Schreiner, et al. Transition1x—a Dataset for Building Generalizable Reactive Machine Learning Potentials. arXiv preprint arXiv:2207. 12858 (2022). (13 pages).

Shehab, et al. Noise reduction using past causal cones in variational quantum algorithms. arXiv preprint arXiv:1906.00476 (2019). (19 pages).

Smith, et al. ANI-1: An extensible neural network potential with DFT accuracy at force field computational cost. arXiv preprint arXiv:1610.08935 (2016). (30 pages).

Smith, et al. Approaching coupled cluster accuracy with a general-purpose neural network potential through transfer learning. Nat Commun. Jul. 1, 2019;10(1):2903. doi: 10.1038/s41467-019-10827-4.

Smith, et al. Less is more: sampling chemical space with active learning. arXiv preprint arXiv:1801.09319 (2018). (29 pages).

Smith, et al. Less is more: Sampling chemical space with active learning. J Chem Phys. Jun. 28, 2018;148(24):241733. doi: 10.1063/1.5023802.

Smith, et al. The ANI-1ccx and ANI-1x data sets, coupled-cluster and density functional theory properties for molecules. Sci Data. May 1, 2020;7(1):134. doi: 10.1038/s41597-020-0473-z. (10 pages).

Spiekermann, et al. High accuracy barrier heights, enthalpies, and rate coefficients for chemical reactions. Sci Data. Jul. 18, 2022;9(1):417. doi: 10.1038/s41597-022-01529-6. (12 pages).

Svensson, et al. Conformal Regression for Quantitative Structure-Activity Relationship Modeling-Quantifying Prediction Uncertainty. J Chem Inf Model. May 29, 2018;58(5):1132-1140. doi: 10.1021/acs.jcim.8b00054. Epub May 10, 2018.

Torres, et al. Low-Scaling Algorithm for Nudged Elastic Band Calculations Using a Surrogate Machine Learning Model. arXiv preprint arXiv:1811.08022 (2018). https://doi.org/10.48550/arXiv. 1811.08022 (12 pages).

U.S. Appl. No. 16/888,446 Office Action dated Feb. 6, 2023.

U.S. Appl. No. 16/888,446 Office Action dated Oct. 13, 2023.

Wang, et al. A fully differentiable ligand pose optimization framework guided by deep learning and traditional scoring functions. arXiv preprint arXiv:2206.13345 (2022). (19 pages).

Wang, et al. Relation: A Deep Generative Model for Structure-Based De Novo Drug Design. J Med Chem. Jul. 14, 2022;65(13):9478-9492. doi: 10.1021/acs.jmedchem.2c00732. Epub Jun. 17, 2022.

Zhang, et al. E3bind: An end-to-end equivariant network for protein-ligand docking. arXiv preprint arXiv:2210.06069 (2022). (16 pages).

Zhao, Q. Training and retraining of neural network trees. IJCNN'01. International Joint Conference on Neural Networks. Proceedings (Cat. No.01CH37222). vol. 1. IEEE, Jul. 2001. https://doi.org/10. 1109/IJCNN.2001.939114.

Zimmerman, P. Reliable Transition State Searches Integrated with the Growing String Method. J Chem Theory Comput. Jul. 9, 2013;9(7):3043-3050. doi: 10.1021/ct400319w. Epub Jun. 11, 2013.

Zimmerman, P.M. Automated discovery of chemically reasonable elementary reaction steps. J Comput Chem. Jun. 15, 2013;34(16):1385-92. doi: 10.1002/jcc.23271. Epub Mar. 18, 2013.

Zimmerman, P.M. Growing string method with interpolation and optimization in internal coordinates: method and examples. J Chem Phys. May 14, 2013;138(18):184102. doi: 10.1063/1.4804162.

Zimmerman, P.M. Navigating molecular space for reaction mechanisms: an efficient, automated procedure. Molecular Simulation, 41(1-3), 43-54. (2015) https://doi.org/10.1080/08927022.2014. 894999 (12 pages).

Zimmerman, P.M. Single-ended transition state finding with the growing string method. J Comput Chem. Apr. 5, 2015;36(9):601-11. doi: 10.1002/jcc.23833. Epub Jan. 8, 2015.

Aggarwal et al.: Evolutionary network analysis: A survey. ACM Computing Surveys 47(1):10:1-10:36 (2014).

Akama et al. Implementation of divide-and-conquer method including Hartree-Fock exchange interaction. J Comput Chem 28(12):2003-2012 (2007).

Alidaee et al. Solving the maximum edge weight clique problem via unconstrained quadratic programming. European Journal of Operational Research 181(2):592-597 (2007).

Amelio et al.: Community mining in signed networks: A multiobjective approach. ASONAM 2013: Proceedings of the 2013 IEEE/ACM International Conference on Advances in Social Networks Analysis and Mining, pp. 95-99 https://doi.org/10.1145/2492517. 2492641 (2013).

Amin et al.: Quantum Boltzmann Machine. arXiv reprint arXiv:1601. 02036 [1-10] 2016.

Anchuri et al.: Communities and balance in signed networks: A spectral approach. In Proceedings of the 2012 International Conference on Advances in Social Networks Analysis and Mining (ASONAM 2012), ASONAM 2012, pp. 235-242, Washington, DC, USA (2012).

Anthony et al. Quadratization of symmetric pseudo-Boolean functions. Discrete Appl. Math. 203:1-12 (2016).

Aspuru-Guzik et al. Simulated Quantum Computation of Molecular Energies. Science 309:1704 (2005).

Assad et al. The quadratic minimum spanning tree problem. Naval Research Logistics 39:399-417(1992).

Babbush et al. Resource Efficient Gadgets for Compiling Adiabatic Quantum Optimization Problems. arXiv:1307.8041v1 [quant-ph] (pp. 1-11) (Jul. 2013) Retrieved from the Internet: (https://arxiv. org/pdf/1307.8041.pdf5).

Babbush. Towards Viable Quantum Computation for Chemistry, 2015, [Retrieved on Feb. 27, 2020]. Retrieved from the internet: <url: <a=""href="https://pdfs.sennanticscholar.org/aff0/ 5ecf5f58c2206c923b767d76bed7f43b2a66.pdf">https://pdfs. sennanticscholar.org/aff0/5ecf5f58c2206c923b767d76bed7f43b2a66. pdf? ga=2.2412147.276222377.1582743768639821531.1551220934 376 Pages (1376) (2015).</url:>.

Barends et al. Digitized adiabatic quantum computing with a superconducting circuit. Nature 534(7606):222-226 (2016).

Bartak et al. Constraint Satisfaction Techniques for Planning and Scheduling Problems (Coplas-15), Jul. 6, 2015. Retrieved on Nov. 17, 2019 at https://www.cs.bgu.ac.il/-icapsl5/workshops/Proceedings% 2000PLAS%202015.pdf (pp. 1-41) (2015).

Beasley. Integer programming solution methods. Available at URL: http://people.brunel.ac.uk/-mastjjb/jeb/natcor_ip_rest.pdf (20 pgs.) (2011).

Berry et al. Simulating Hamiltonian dynamics with a truncated Taylor series. Phys Rev Lett 114(9):090502 (2015).

Bertoni et al. Quantum logic gates based on coherent electron transport in quantum wires. Physical Review Letters 84(25):5912 (2000).

Bhagat et al.: Node Classification in Social Networks. arXiv:1101. 3291v1 Social Network Data Analytics, pp. 115-148 (2011).

Bian et al. The Ising model: teaching an old problem new tricks. D-Wave Systems 2 (32 pgs.) (2010).

Bojchevski et al.: Deep Gaussian Embedding of Graphs: Unsupervised Inductive Learning via Ranking. arXiv.org, Cornell University, arXiv:1707.03815v4 [stat.ML], pp. 1-13 (2018).

Boros et al. On quadratization of pseudo-Boolean functions. arXiv:1404. 6538v1 [math.OC] (11 pgs.) (2014).

Boros et al. Pseudo-boolean optimization. Discrete Applied Mathematics 123(1):155-225 (2002).

Bravyi et al. Fermionic quantum computation. arXiv:quant-ph/ 0003137 (2000).

Bromley et al.: Applications of near-term photonic quantum computers: software and algorithms. Quantum Science and Technology 5:034010DOI:10.1088/2058-9565/ab8504 arXiv:1912.07634 [1-36] (2019).

Burell: An Introduction to Quantum Computing using Cavity QED concepts. arXiv preprint arXiv:1210.6512 (2012).

(56)         References Cited

OTHER PUBLICATIONS

Byrnes et al. Macroscopic quantum computation using Bose-Einstein condensates. arXiv preprint quantum-ph/1103.5512 (2011).

Cai et al. A practical heuristic for finding graph minors.arXiv:1406.2741 [quant-ph] (16 pgs) (2014).

Cai et al.: A survey on network community detection based on evolutionary computation. International Journal of Bio-Inspired Computation 8(2):84-98 (2016).

Cao et al.: Advances in Knowledge Discovery and Data Mining. Springer International, pp. 82-95 (2015).

Carleo et al.: Constructing exact representations of quantum many-body systems with deep neural networks. Nat Commun. 9(1):5322, pp. 1-11 doi: 10.1038/s41467-018-07520-3 (2018).

Carleo et al.: Solving the quantum many-body problem with artificial neural networks. pre-print arXiv:1606.02318 Science 355(6325):602-606 doi:10.1126/science.aag2302 (2016).

Carrasquilla et al.: Reconstructing quantum states with generative models. arXiv:1810.10584 Nature Machine Intelligence 1(3):155-161 arXiv:1810.10584 (2019).

Carrasquilla. Machine learning for quantum matter. https://arxiv.org/pdf/2003.11040.pdf (2020).

Chen et al.: Community Detection via Maximization of Modularity and Its Variants. IEEE Transactions on Computational Social Systems 1(1):46-65 DOI:10.1109/TCSS.2014.2307458 (2014).

Chen et al.: Epidemic spreading on networks with overlapping community structure. Physica A: Statistical Mechanics and its Applications 391(4):1848-1854 (2012).

Chiang et al.: Exploiting longer cycles for link prediction in signed networks. In Proceedings of the 20th ACM International Conference on Information and Knowledge Management, CIKM 2011, pp. 1157-1162, New York, NY, USA [1-6] (2011).

Choi. Minor-embedding in adiabatic quantum computation: I. The parameter setting problem. Quantum Information Processing 7(5):193-209 (2008).

Chowdhury et al.: Quantum algorithms for Gibbs sampling and hitting-time estimation. arXiv:1603.02940 Quant. Inf. Comp. 17(1-2):41-64 (2017).

Chuang et al.: Experimental implementation of fast quantum searching. Physical Review Letters 80(15):3408-3411 DOI:10.1103/PhysRevLett.80.3408 (1998).

Clarke et al. Superconducting quantum bits. Nature 453(7198):1031 (2008).

Conforti et al.: Integer Programming: Graduate Texts in Mathematics 271. Springer [1-466] (2014).

Conway et al. An FPGA-based instrumentation platform for use at deep cryogenic temperatures. arxiv.org/abs/1509.06809 (2015).

Cory et al. Nuclear magnetic resonance spectroscopy: An experimentally accessible paradigm for quantum computing. arXiv preprint quant-ph/97090 01(1997).

Cowtan et al. On the qubit routing problem. arXiv:1902.08091v2 (2019).

Cramer et al. Efficient quantum state tomography, Nature Communications 1:149 (2010).

Debnath et al.: Demonstration of a small programmable quantum computer with atomic qubits. arXiv:1603.04512 Nature 536(7614):63-66 doi:10.1038/nature18648 (2016).

Deutsch et al. Quantum computing with neutral atoms in an optical lattice. arXiv preprint quant-ph/0003022 Fortschritte der Physik Progress of Physics; Oct. 2000, vol. 48, No. 9-11, pp. 925-943 (2000).

Durr et al. A Quantum Algorithm for Finding the Minimum. arXiv:quant-ph/9607014 (1996).

Dwave, Reverse Quantum Annealing for Local Refinement of Solutions, D-Wave Whitepaper Series, Nov. 9, 2017. Retrieved online on Aug. 14, 2019 from https://www.dwavesys.com/sites/default/files/14-1018A-A_Reverse_Quantum_Annealing_for_Local_Refinement_Of_Solutions.pdf (2 pgs.).

Elvira et al.: Efficient Multiple Importance Sampling Estimators. pre-print arxiv.org/pdf/1505.05391, pp. 1-7 (2015).

EP17812349.3 Third Party Observations dated Oct. 29, 2020.

Esmailian et al.: Mesoscopic analysis of online social networks: The role of negative ties. arXiv:1411.6057v1 Phys. Rev. E90:042817, pp. 1-13 (2014).

Farhi et al. A Quantum Approximate Optimization Algorithm. arXiv:1411.4028 (2014).

Farhi et al. Quantum Adiabatic Evolution Algorithms versus Simulated Annealing.arXiv.org:quant ph/0201031 pp. 1-16 (2002).

Farhi et al. Quantum computation by adiabatic evolution. arXiv preprint quant-ph/0001106 (24 pgs) (2000).

Fedichkin et al. Novel coherent quantum bit using spatial quantization levels in semiconductor quantum dot. arXiv preprint quant-ph/0006097 (2000).

Fedorov et al. Exploring chemistry with the fragment molecular orbital method. Physical Chemistry Chemical Physics 14:7562-7577 (2012).

Ferrara et al.: Detecting criminal organizations in mobile phone networks. arXiv:1404.1295v1 Expert Systems with Applications 41(13):5733-5750 (2014).

Fortunato: Community detection in graphs. arXiv.org, Cornell University, arXiv:0906.0612v1 [physics.soc-ph], pp. 1-89 (2009).

Freund. Applied Lagrange Duality for Constrained Optimization. Massachusetts Institute of Technology (pp. 1-35) (2004).

Gelman et al.: Simulating normalizing constants: from importance sampling to bridge sampling to path sampling. Statist. Sci. 13(2):163-185 DOI:10.1214/ss/1028905934 (1998).

Geoffrion. Lagrangean relaxation for integer programming. Mathematics Programming Study 2, North-Holland Publishing Company (pp. 1-34) (1974).

Glover et al. Polynomial unconstrained binary optimisation Part 1, 2011, [Retrieved on Feb. 27, 2020]. Retrieved from the internet: <url: <a="”href="http://leedsfaculty.colorado.edu/glover/fred%2Opubs/424%20%20%20Polynonnial”>http://leedsfaculty.colorado.edu/glover/fred%2Opubs/424%20%20%20Polynonnial 25 Pages (231256) (2011).</url:>.

Glover et al.: Tabu Search: Modern Heuristic Techniques for Combinatorial Problems. Colin R. Reeves (Ed.) Black Scientific Publications, Oxford [1-62] (1993).

Glover: Tabu search—part II. ORSA Journal on computing 2(1):4-32.1 4-32 DOI:10.1287/ijoc.2.1.4 (1990).

Greene et al. Simulated annealing without rejected moves. IEEE Transactions on Computer-Aided Design of Integrated Circuits and Systems 5(1):221-228 (1986).

Grover. A fast quantum mechanical algorithm for database search. Proceedings of the 28th Annual ACM Symposium on the Theory of Computing (pp. 212-219) (1996).

Gwennap: Groq Rocks Neural Networks. The Linley Group Microprocessor Report www.groq.com/groq-tsp-leads-in-inference-performance/ [1-5] (2020).

Hamilton et al.: Representation Learning on Graphs: Methods and Applications. arXiv.org, Cornell University, arXiv:1709.05584v3 [cs.SI], pp. 1-24 (2018).

Harneit. Spin Quantum Computing with Endohedral Fullerenes. arXiv preprint arXiv:1708.092 98 (2017).

He et al.: MISAGA: An Algorithm for Mining Interesting Subgraphs in Attributed Graphs. IEEE Transactions on Cybernetics 48(5):1369-1382 (2018).

Heider: Attitudes and cognitive organization. The Journal of Psychology 21(1):107-112 (1946).

Huang et al.: Predicting many properties of a quantum system from very few measurements. Nature Physics 16(10)1050-1057 doi:arxiv.org/abs/2002.08953 [1-40](2020).

Hukushima et al. Exchange Monte Carlo Method and Application to Spin Glass Simulations. Journal of the Physical Society of Japan 65:1604 (1996).

Humble et al.: Software Systems for High-performance Quantum Computing. IEEE Xplore doi:10.1109/HPEC.2016.7761628 [1-8](2016).

Imamoglu et al.: Quantum information processing using quantum dot spins and cavity QED. Phys. Rev. Lett.; Nov. 1999, vol. 83, No. 20, pp. 4204-4207 http://134.34.147.128/burkard/sites/default/files/images/Imamoglu_Phys.%20Rev.%20Lett._1999-01-01.pdf (1999).

Ishikawa. Transformation of General Binary MRF Minimization to the First-Order Case. IEEE Transactions on Pattern Analysis and Machine Intelligence. 33(6):1234-1249 (2011).

(56)  References Cited

OTHER PUBLICATIONS

Izmaylov et al.: Revising the measurement process in the variational quantum eigensolver: is it possible to reduce the number of separately measured operators? Chem Sci. 10(13):3746-3755 (2019).
Johnson et al. Quantum annealing with manufactured spins. Nature 473(7346):194-198 (2011).
Jones et al.: Implementation of a quantum algorithm to solve Deutsch's problem on a nuclear magnetic resonance quantum computer. arXiv:quant-ph/9801027v2 The Journal of chemical physics, 109(5):1648-1653 DOI:10.1063/1.476739 (1998).
Jordan. Fast Quantum Algorithm for Numerical Gradient Estimation. Physical Review Letters 95:050501 (2015).
Kaminsky et al.: Scalable architecture for adiabatic quantum computing of NP-hard problems. Quantum Computing & Quantum Bits in Mesoscopic Systems, pp. 229-236 DOI:10.1007/978-1-4419-9092-1_25 [arXiv:quant-ph/0211152 1-10] (2004).
Kane. A silicon-based nuclear spin quantum computer. Nature 393(6681):133 (1998).
Karimi et al. A subgradient approach for constrained binary programming via quantum adiabatic evolution. arXiv preprint arXiv:1605.09462 (16 pgs.) (2016).
Karimi et al. Boosting quantum annealer performance via quantum persistence. Online publication eprint arXiv:1606.07797 (Jun. 27/27 and updated Aug. 30, 2016). Accessed May 17, 2017 and available from https://www.arxiv.org/pdf/1606.07797.pdf (25 pgs).
Kassal et al.: Simulating chemistry using quantum computers. Annu Rev Phys Chem. 62:185-207 (2011).
Katzgraber et al. Seeking quantum speedup through spin glasses: the good, the bad, and the ugly. Physical Review 5(3):031026 (2015).
Kellerer et al. Knapsack Problems. Springer (15 pgs.) (2004).
Kempe et al.: The Complexity of the Local Hamiltonian Problem. SIAM Journal of Computing. 35(5):1070-1097 Rev.2008 DOI: arXiv:quant-ph/0406180v2 [1-30] (2005).
Kielpinski et al. Architecture for a large-scale ion-trap quantum computer. Nature 417(6890):709 (2002).
Kirkpatrick et al. Optimization by simulated annealing. Science 220:671-680 (1983).
Kitaura et al. Fragment molecular orbital method: an approximate computational method for large molecules. Chemical Physics Letters 313(3-4):701-706 (1999).
Knill et al. Efficient linear optics quantum computation. arXiv preprint quant-ph/0006088 (2000).
Knizia et al. Density Matrix Embedding: A Simple Alternative to Dynamical Mean-Field Theory. Phys Rev Lett 109:186404 (2012).
Kobayashi et al. Chapter 5: Divide-and-conquer approaches to quantum chemistry: Theory and implementation, in Linear-Scaling Techniques in Computational Chemistry and Physics: Methods and Applications, edited by Zalesny et al. (Springer Netherlands, Dordrecht, 2011) pp. 97-127.
Kochenberger et al.: The unconstrained binary quadratic programming problem: A survey. J Comb Optim. 28(1)58-81 DOI:10.1007/s10878-014-9734-0 (2014).
Kokail et al. Self-verifying variational quantum simulation of lattice models. Nature 569(7756):355-360 (2019).
Konda et al. Actor-Critic Algorithms. Advances in Neural Information Processing Systems. pp. 1008-1014 (2000).
Kunegis et al.: The slashdot zoo: Mining a social network with negative edges. In Proceedings of the 18th International 20 Conference on World Wide Web, WWW 2009, pp. 741-750, New York, NY, USA DOI:10.1145/1526709.1526809 (2009).
Lemieux et al.: Efficient Quantum Walk Circuits for Metropolis-Hastings Algorithm. Quantum 4:287 [1-15] (2020).
Lemieux et al.: Resource estimate for quantum many-body ground-state preparation on a quantum computer. Physical Review A 103(5)052408 DOI:10.1103/PhysRevA.103.052408 [1-9] (2021).
Lenstra: Integer programming with a fixed number of variables. 8(4):538-548 URL: https://doi.org/10.1287/moor.8.4.538 (1983).

Leskovec et al.: Empirical Comparison of Algorithms for Network Community Detection. Proceedings of International World Wide Web Conference 2010, Raleigh, North Carolina, USA, pp. 1-10 (2010).
Leskovec et al.: Predicting positive and negative links in online social networks. In Proceedings of the 19th International Conference on World Wide Web, WWW 2010, pp. 1-10, New York, NY, USA (2010).
Leuenberger et al. Quantum computing in molecular magnets. arXiv preprint cond-mat/0011415 (2001).
Levit et al. Free energy-based reinforcement learning using a quantum processor. Available at https://arxiv.org/pdf/1706.00074.pdf (May 2017) (8 pgs.).
Leyffer. Deterministic Methods for Mixed Integer Nonlinear Programming. University of Dundee (pp. 1-60 and pp. 1-58) (1993).
Li et al. Nonlinear Integer Programming. New York, NY (pp. 1-452) (2006).
Li: Tackling the Qubit Mapping Problem for NISQ-Era Quantum Devices. arXiv:1809.02573v2 Proceedings of the Twenty-Fourth International Conference on Architectural Support for Programming Languages and Operating Systems. (2019).
Liben-Nowell et al.: The link prediction problem for social networks. In Proceedings of the Twelfth International Conference on Information and Knowledge Management, CIKM 2003, pp. 556-559, New York, NY, USA [1-19](2004).
Lin et al.: Understanding community effects on information diffusion. Advances in Knowledge Discovery and Data Mining, pp. 82-95 DOI:10.1007/978-3-319-18038-0_7 (2015).
Low et al.: Hamiltonian simulation by Qubitization. arXiv:1610.06546v3 Quantum 3:163 URL:https://doi.org/10.22331/q-2019-07-12-163 [1-23] (2019).
Lu et al.: Demonstration of Shor's quantum factoring algorithm using photonic qubits. arXiv:0705.1684v3 Physical Review Letters 99(25):250504 DOI:10.1103/PhysRevLett.99.250504 [1-5] (2007).
Lu et al.: KKT Solution and Conic Relaxation for Solving Quadratically Constrained Quadratic Programming Problem. Siam J. Optim. 21(4):1475-1490 DOI:10.1137/100793955 (2011).
Lu et al., Quantum chemistry simulation on quantum computers: theories and experiments. Physical Chemistry Chemical Physics 14(26):9411-9420 (2012).
Lyon. Spin-based quantum computing using electrons on liquid helium. arXiv preprint cond-mat/030158 1 (2006).
Martinis et al. Rabi oscillations in a large Josephson-junction qubit. Physical Review Letters 89:117901 (2002).
Marx et al. Chapter 1. Setting the stage: why ab initio molecular dynamics? In Ab Initio Molecular Dynamics: Basic Theory and Advanced Methods. Cambridge, UK Cambridge University Press (pp. 1-8) (2009).
Massa et al.: Controversial users demand local trust metrics: An experimental study on Epinions.com community. In Proceedings of the 20th National Conference on Artificial Intelligence AAA Press vol. 1, AAAI-05:121-126 (2005).
Matsuura et al. VanQver: The Variational and Adiabatically Navigated Quantum Eigensolver. New Journal of Physics 22:053023 (2020).
Mcclean et al. The Theory Of Variational Hybrid Quantum-Classical Algorithms. New Journal of Physics 18:023023. Retrieved online on Aug. 14, 2019 from https://iopscience.iop.org/article/10.1088/1367-2630/18/2/023023/ampdf (21 pgs) (2016).
Mcgeoch et al. Experimental Evaluation of an Adiabatic Quantum System for Combinatorial Optimization. Computing Frontiers. Proceeding CF '13 Proceedings of the ACM International Conference on Computing Frontiers. Article No. 23. Available athttp://www.cs.amherst.edu/ccm/cf14-mcgeoch.pdf (11 pgs) (May 14-16, 2013).
Mckiernan et al. Automated quantum programming via reinforcement learning for combinatorial optimization. Quantum Physics. arXiv.org quant-ph arXiv:1908.08054 (2019).
Medus et al.: Detection of community structures in networks via global optimization. Physica A: Statistical Mechanics and its Applications 358(2-4):593-604 DOI:10.1016/j.physa.2005.04.022 (2005).
Melko et al.: Restricted Boltzmann machines in quantum physics. Nature Physics 15(9):887-892 DOI:10.1038/s41567-019-0545-1 (2019).

(56) References Cited

OTHER PUBLICATIONS

Metz. IBM Is Now Letting Anyone Play With Its Quantum Computer. Wired. (5 pgs.) (May 2016).

Mnih et al. Asynchronous Methods for Deep Reinforcement Learning, in International Conference on Machine Learning, pp. 1928-1937 (2016).

Mnih et al. Playing Atari with Deep Reinforcement Learning. arXiv:1312.5602 (2013).

Moll et al., Optimizing qubit resources for quantum chemistry simulations in second quantization on quantum computer. Journal of Physics A: Mathematical and Theoretical 49(29):295301 (2016).

Moll et al.: Quantum optimization using variational algorithms on near-term quantum devices. Quantum Sci. Technol. 3 030503 [1-17] (2018).

Montanaro. Quantum walk speedup of backtracking algorithms. arXiv:1509.02374v2 [quant-ph] (23 pgs) (2015).

Monz et al.: Realization of a scalable Shor algorithm. arXiv:1507.08852 Science 351(6277):1068-1070 DOI:10.1126/science.aad9480 (2015).

Motzkin et al.: Maxima for graphs as a new proof of a theorem of Turan. Canadian Journal of Mathematics 17:533-540 DOI:10.4153/CJM-1965-053-6 (1965).

Nafradi et al. Room temperature manipulation of long lifetime spins in metallic-like carbon nanospheres. Nat Commun 7:12232 (2016).

Nagy et al.: Variational quantum Monte Carlo method with a neural-network ansatz for open quantum systems. Phys Rev Letters 122(25):250501 doi:arxiv.org/abs/1902.09483 [1-10](2019).

Nam et al.: Ground-state energy estimation of the water molecule on a trapped ion quantum computer. arXiv preprint arXiv:1902.10171, pp. 1-14 (2019).

Newman et al.: Finding and evaluating community structure in networks. Phys. Rev. E. 69:026113, pp. 1-16 (2004).

Newman: Modularity and community structure in networks. PNAS 103(23):8577-8582 (2006).

Niklasson et al., Fast method for quantum mechanical molecular dynamics. Physical Review B 86(17):174308 (2012).

Nishikawa et al. Quantum Chemistry Grid/Gaussian Portal, Journal of the twenty second Annual Research Society, Japan Simulation Society, Jun. 18, 2003, pp. 369 to 372 (English Abstract).

Nizovtsev et al. A quantum computer based on NV centers in diamond: optically detected nutations of single electron and nuclear spins. Optics and spectroscopy 99(2):233-244 (2005).

O'Gorman et al. Compiling planning into quantum optimization problems: a comparative study. Proc. of the Workshop on Constraint Satisfaction Techniques for Planning and Scheduling Problems (COPLAS-15) (pp. 11-20) (Jun. 2015) Retrieved from the Internet: <https://www.cs.bgu.acilt--icaps15/workshops/Proceedings%2000PLAS%202015.pdf>.

Ohlsson et al. Quantum computer hardware based on rare-earth-ion-doped inorganic crystals. Optics Communications 201(1-3):71-77 (2002).

Olsson et al.: Solving Large Scale Binary Quadratic Problems: Spectral Methods vs. Semidefinite Programming. IEEE Conference on Computer Vision and Pattern Recognition, pp. 1-8, doi:10.1109/CVPR.2007.383202 (2007).

O'Malley et al. Scalable Quantum Simulation of Molecular Energies. Phys. Rev. X 6:031007 (2016).

Orus. Tensor networks for complex quantum systems. Nature Reviews Physics 1:538 (2019).

Papamakarios: Comparison of Modern Stochastic Optimization Algorithms. Scholar article. [1-13] (2014) www.richtarik.org/papers/Papamakarios.pdf.

PCT/CA2017/050320 International Search Report and Written Opinion dated Jun. 27, 2017.

PCT/CA2017/050637 International Search Report and Written Opinion dated Aug. 25, 2017.

PCT/CA2017/050709 International Search Report and Written Opinion dated Sep. 19, 2017.

PCT/CA2017/051610 International Search Report and Written Opinion dated Mar. 21, 2018.

PCT/CA2018/051531 International Search Report and Written Opinion dated Feb. 20, 2019.

PCT/CA2018/051534 International Search Report and Written Opinion dated Feb. 21, 2019.

PCT/CA2019/050852 International Search Report and Written Opinion dated Aug. 15, 2019.

PCT/CA2019/051752 International Search Report and Written Opinion dated Mar. 17, 2020.

PCT/CA2020/050641 International Search Report and Written Opinion dated Jul. 21, 2020.

PCT/CA2021/050513 International Search Report and Written Opinion dated Jul. 14, 2021.

PCT/CA2021/050709 International Search Report and Written Opinion dated Aug. 3, 2021.

PCT/CA2021/050750 International Search Report and Written Opinion dated Aug. 6, 2021.

PCT/IB2017/051038 International Search Report dated May 16, 2017.

PCT/IB2017/051224 International Search Report dated May 18, 2017.

PCT/IB2019/055226 International Search Report and Written Opinion dated Nov. 26, 2019.

PCT/IB2020/055801 International Search Report and Written Opinion dated Oct. 30, 2020.

PCT/IB2020/061464 International Search Report and Written Opinion dated Mar. 4, 2021.

PCT/IB2021/051965 International Search Report and Written Opinion dated May 31, 2021.

Peruzzo et al. A variational eigenvalue solver on a quantum processor. arXiv:1304.3061 (2013).

Pizzuti: A multi-objective genetic algorithm for community detection in networks. IEEE International Conference on Tools with Artificial Intelligence, pp. 379-386 DOI:10.1109/ICTAI.2009.58 (2009).

Poulin et al.: Sampling from the thermal quantum Gibbs state and evaluating partition functions with a quantum computer. arXiv:0905.2199 Physical Review Letters 103(22), pp. 1-7 DOI:10.1103/PhysRevLett.103.220502 (2009).

Preskill. Quantum Computing in the NISQ era and beyond. Quantum 2:79 arXiv:1801.00862 (2018).

Quek et al.: Adaptive Quantum State Tomography with Neural Networks. arXiv.org, Cornell University, arXiv:1812.06693v1 [quant-ph], pp. 1-13 pages (2018).

Reiher et al.: Elucidating reaction mechanisms on quantum computers. PNAS USA 114(29):7555-7560 (2017).

Ronagh et al. Solving constrained quadratic binary problems via quantum adiabatic evolution. arXiv preprint arXiv:1509.05001 (20 pgs.) (2015).

Rosenberg et al. Building an iterative heuristic solver for a quantum annealer. Computational Optimization and Applications 65:845 (2016).

Rubin: A Hybrid Classical/Quantum Approach for Large-Scale Studies of Quantum Systems with Density Matrix Embedding Theory. Cornell University Library, Ithaca, NY arXiv doi:arxiv.org/abs/1610.06910 [1-10](2016).

Salathe et al.: Dynamics and control of diseases in networks with community structure. PLoS Computational Biology 6(4):e1000736, pp. 1-11 (2010).

Schmidt et al. General Atomic and Molecular Electronic Structure System. Journal of Computational Chemistry 14:1347-1363 (1993).

Schollwock. The density-matrix renormalization group. Review of Modern Physics 77:259 arxiv.org:cond-mat/0409292 (2004).

Schuld et al., "Quantum machine learning in feature Hilbert spaces", Phys. Rev. Lett.; Feb. 1, 2019, vol. 122, pp. 040504-1-040504-12.

Schulman et al. Proximal Policy Optimization Algorithms. arXiv:1707.06347 (2017).

Schwabl: Quantum Mechanics. Springer, 4th Ed. [1-425] (2007).

Sepehry et al. Smooth Structured Prediction Using Quantum and Classical Gibbs Samplers. Available at https://1qbit.com/wp-content/uploads/2018/09/1QBit-Research-Paper-Smooth_Structured-Prediction-Using-Quantum-And_classical-Giobbs-Samplers.pdf (Accessed Feb. 20, 2018) (32 pgs).

(56) References Cited

OTHER PUBLICATIONS

Shapiro et al. A survey of Lagrangean techniques for discrete optimization. Operations Research Center, Massachusetts Institute of Technology, Cambridge, Massachusetts (pp. 1-18 and pp. 1-29) (May 1977).

Shen et al.: Quantum implementation of the unitary coupled cluster for simulating molecular electronic structure. Phys. Rev. A 95, 020501(R) doi:10.1103/PhysRevA.95.020501 [1-6] (2017).

Siraichi et al. Qubit Allocation. CGO 2018—International Symposium on Code Generation and Optimization, Feb. 2018, Vienna, Austria (12 pgs) (2018). pp.1-12.

Sloss et al. Evolutionary Algorithms Review, arXiv:1906.08870 (2019).

Srinivas et al.: Muiltiobjective optimization using non-dominated sorting in genetic algorithms. Evolutionary Computation 2(3):221-248 (1994).

Sun et al. A single-photon switch and transistor enabled by a solid-state quantum memory. arXiv preprint quant-ph/1805.01964 (2018).

Suzuki. Fractal decomposition of exponential operators with applications to many-body theories and Monte Carlo simulations. Physics Letters A 146(6):319-323 (1990).

Svore et al. Toward a Software Architecture for Quantum Computing Design Tools. QPL 2004, pp. 127-144, Retrieved from the Internet: URL:https://www.microsoft.com/en-us/research/wp-content/uploads/2016/02/10Svore-Cros s-Aho-Chuang-Markov.pdf.

SymPy Python. Internals of the Polynomial Manupulation Module. Available online at http://docs.sympy.org/latest/modules/polys/internals.html (Accessed Jun. 2016) (136 pgs).

Tang et al.: A Survey of Signed Network Mining in Social Media. ACM Computing Surveys 9(4):pp. 39:1 to 39:38, arXiv.org, Cornell University, arXiv:1511.07569v3 [cs.SI] (2016).

Tavares et al. New algorithms for Quadratic Unconstrained Binary Optimization (QUBO) with applications in engineering and social sciences. Rutgers University Community Repository. Dissertation—Retrieved from the Internet <URL: https://rucorelibrariessutgers.edu/rutgers-lib/25771/> on Feb. 2, 2018 (460 pgs) ( May 2008).

Temme et al.: Quantum metropolis sampling. Nature 471(7336):87-90 (2011).

Terhal et al.: The problem of equilibration and the computation of correlation functions on a quantum computer. arXiv:quant-ph/9810063 Phys.Rev. A61:22301, pp. 1-35 DOI:10.1103/PhysRevA.61.022301 (2000).

The D-Wave 2X™ Quantum Computer Technology Overview (12 pgs) (2015).

The D-Wave Quantum Computer. Brochure. D-Wave Systems Inc. 2016. www.dwavesys.com.

Torlai et al.: Neural-network quantum state tomography. pre-print arXiv:1703.05334v2 Nature Physics 14:447-450 DOI:10.1038/s41567-018-0048-5 (2017).

Tran et al. A hybrid quantum-classical approach to solving scheduling problems. AAAI Publications, Ninth Annual Symposium on Combinatorial Search. pp. 98-106 (SoCS 2016).

Tran et al. Explorations of Quantum-Classical Approaches to Scheduling a MarsLander Activity Problem. The Workshops of the Thirtieth AAAI Conference on Artificial Intelligence Planning for Hybrid Systems: Technical Report WS-16-12, p. 641-649, published on Mar. 29, 2016.

Trotter. On the product of semi-groups of operators. Proceedings of the American Mathematical Society 10(4):545-551 (1959).

U.S. Appl. No. 16/811,479 Non-Final Office Action dated Aug. 30, 2021.

U.S. Appl. No. 15/014,576 Office Action dated Dec. 26, 2017.

U.S. Appl. No. 15/014,576 Office Action dated Jul. 10, 2017.

U.S. Appl. No. 15/051,271 Office Action dated Mar. 13, 2018.

U.S. Appl. No. 15/051,271 Office Action dated Nov. 24, 2017.

U.S. Appl. No. 15/165,655 1st Action Interview dated Feb. 24, 2017.

U.S. Appl. No. 15/165,655 1st Action Interview dated Oct. 25, 2016.

U.S. Appl. No. 15/165,655 Office Action dated Jun. 2, 2017.

U.S. Appl. No. 15/486,960 Office Action dated Jun. 22, 2017.

U.S. Appl. No. 15/830,953 Office Action dated Feb. 14, 2018.

U.S. Appl. No. 15/831,967 Office Action dated Feb. 27, 2018.

U.S. Appl. No. 15/900,643 Miscellaneous Communication re: Third Party Submission dated Dec. 14, 2018.

U.S. Appl. No. 16/010,244 Miscellaneous Communication re: Third Party Submission dated Apr. 23, 2019.

U.S. Appl. No. 16/010,244 Office Action dated Dec. 2, 2019.

U.S. Appl. No. 16/010,244 Office Action dated Jun. 10, 2019.

U.S. Appl. No. 16/124,083 Miscellaneous Communication re: Third Party Submission dated Jul. 11, 2019.

U.S. Appl. No. 16/124,083 Office Action dated Jul. 18, 2019.

U.S. Appl. No. 16/124,083 Office Action dated Nov. 21, 2019.

U.S. Appl. No. 16/162,249 Miscellaneous Communication re: Third Party Submission dated May 2, 2019.

U.S. Appl. No. 16/162,249 Office Action dated Dec. 2, 2019.

U.S. Appl. No. 16/162,249 Office Action dated Jun. 12, 2019.

U.S. Appl. No. 16/888,446 3rd Party Submission dated Apr. 7, 2021.

Van Dam et al. How powerful is adiabatic quantum computation Proceedings 42nd IEEE Symposium on Foundations of Computer Science (pp. 279-287) (Oct. 2001).

Vartiainen: Unitary Transformations for Quantum Computing. Doctoral Dissertation. Helsinki University of Technology TKK dissertations. DOI: aaltodoc.aalto.fi/handle/123456789/2551 [1-56] (2005).

Veis et al.: Quantum computing applied to calculations of molecular energies: CH2 benchmark. J Chem Phys. 133(19):194106 doi:10.1063/1.3503767 [1-29](2010).

Venuti et al.: Adiabaticity in open quantum systems. arXiv:1508.05558v2 Phys. Rev. A93(3):032118, pp. 1-12 DOI:10.1103/PhysRevA.93.032118 (2016).

Vinci et al. Quantum annealing correction with minor embedding. Physical Review A 92.4 (34 pgs) (Jul. 2015).

Wang et al. Population Annealing: Theory and Application in Spin Glasses. Physics Review E 92:961 (2015).

Waskiewicz: Friend of a friend influence in terrorist social networks. In Proceedings on the International Conference on Artificial Intelligence (ICAO, pp. 1-5. The Steering Committee of The World Congress in Computer Science, Computer Engineering and Applied Computing (WorldComp) (2012).

Wendin: Quantum information processing with superconducting circuits: a review. Rep Prog Phys. 80(10):106001 doi:10.1088/1361-6633/aa7e1a [1-50](2017).

White. Density Matrix Formulation for Quantum Renormalization Groups. Physical Review Letters 69:286 (1992).

Whitfield et al., Simulation of electronic structure Hamiltonians using quantum computers. Molecular Physics 109(5):735-750 (2011).

Wigner et al. Paulische equivalence ban. Magazine for physics 47:631 (1928) (English Abstract).

Wooters et al. The no-cloning theorem. Physics Today 62(2):76-77 (2009).

Wouters et al. A Practical Guide to Density Matrix Embedding Theory in Quantum Chemistry. J Chem Theory Comput. 12(6):2706-19 (2016).

Xu et al.: Neural network state estimation for full quantum state tomography. ArXiv preprint doi:arxiv.org/abs/1811.06654 [1-8] (2018).

Yang. Direct calculation of electron density in density-functional theory: Implementation for benzene and a tetrapeptide, Physical Review A 44:(11):7823-7826 (1991).

Zahedinejad et al.: Multi-Community Detection in Signed Graphs Using Quantum Hardware. arXiv.org, 1QBit online research paper, Cornell University, arXiv:1901.04873v1 [quant-ph], pp. 1-10 (2019).

Zimmerman et al. Strong Correlation in Incremental Full Configuration Interaction. Journal of Chemical Physics 146:224104 (2017).

Zulehner et al. Efficient mapping of quantum circuits to the IBM QX architectures. In Design, Automation & Test in Europe Conference & Exhibition 2018 38(7):1226-1236 (2018).

Office Action in Japanese Appln. No. 2021-567060, mailed on Feb. 13, 2025, 7 pages (with English translation).

* cited by examiner

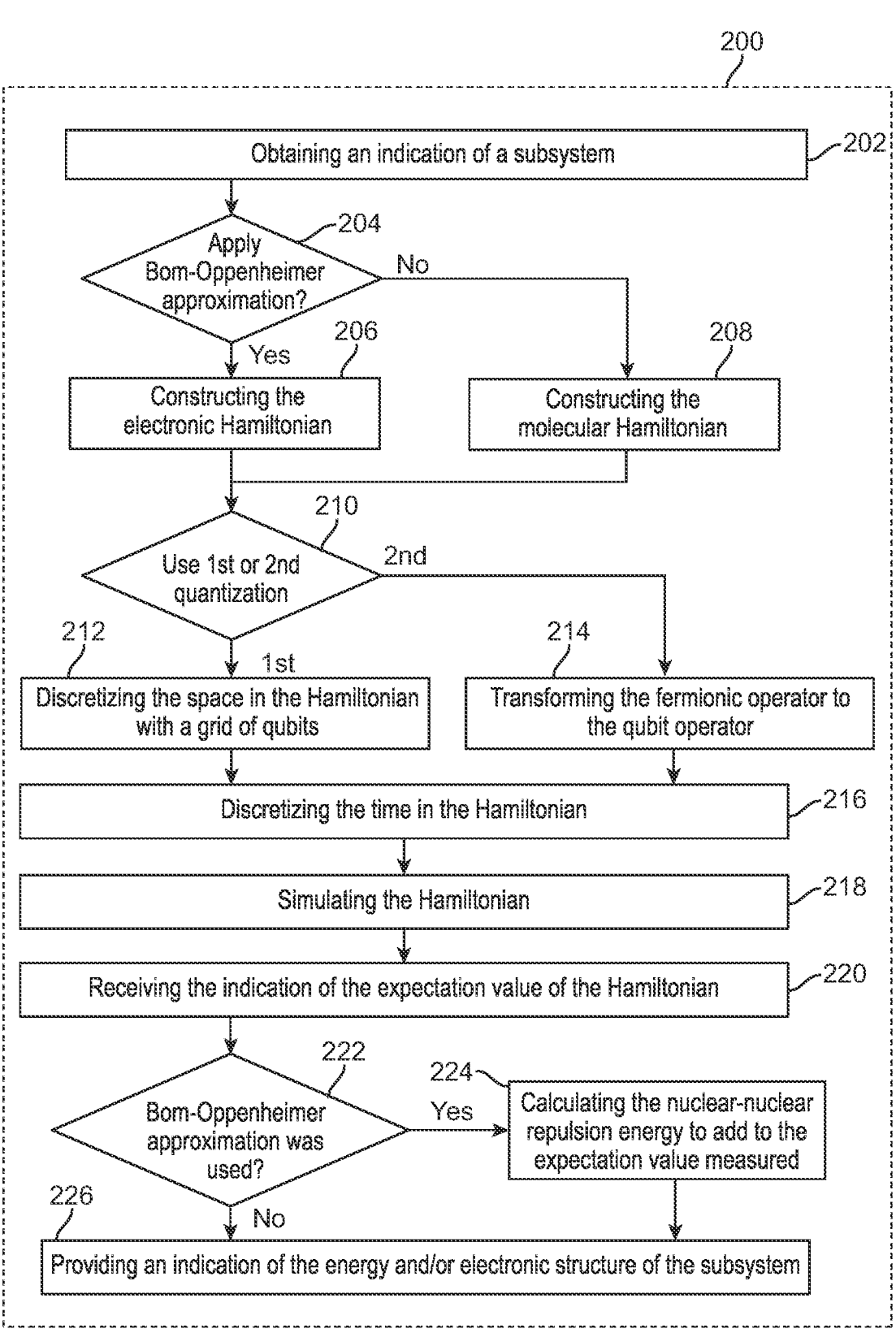

200

Obtaining an indication of a subsystem — 202

204

Apply Bom-Oppenheimer approximation? — No

Yes — 206

Constructing the electronic Hamiltonian

208

Constructing the molecular Hamiltonian

210

Use 1st or 2nd quantization — 2nd

212

1st

Discretizing the space in the Hamiltonian with a grid of qubits

214

Transforming the fermionic operator to the qubit operator

Discretizing the time in the Hamiltonian — 216

Simulating the Hamiltonian — 218

Receiving the indication of the expectation value of the Hamiltonian — 220

222

Bom-Oppenheimer approximation was used? — Yes

224

Calculating the nuclear-nuclear repulsion energy to add to the expectation value measured No

226

Providing an indication of the energy and/or electronic structure of the subsystem

FIG. 2

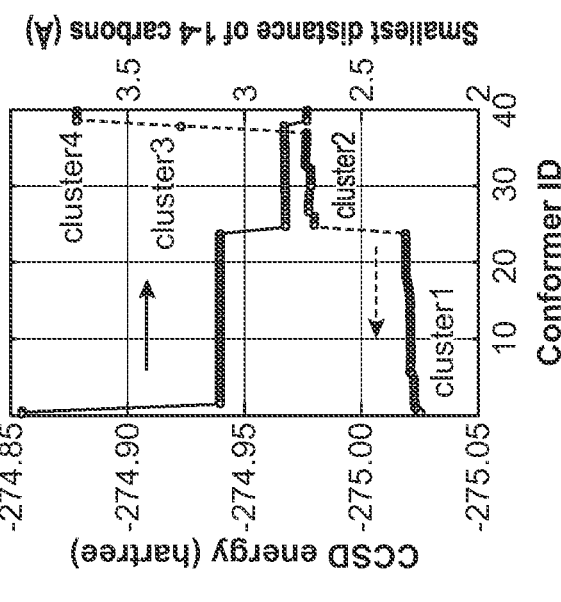
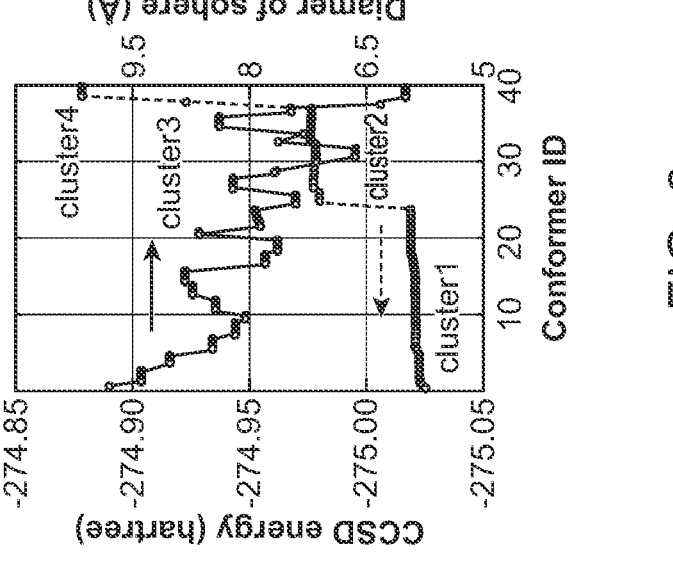
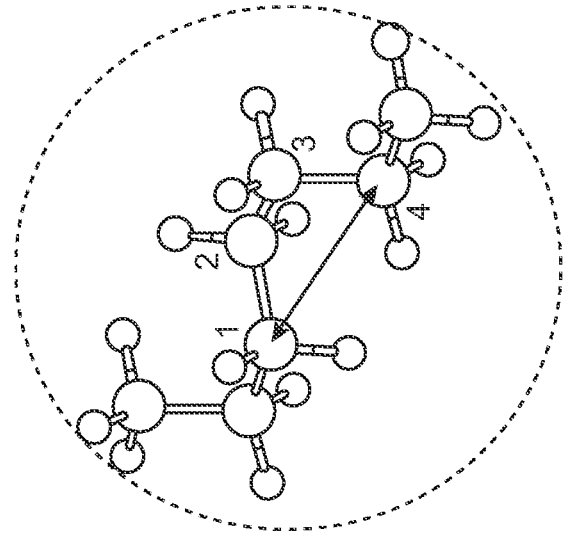
FIG 6

• atoms
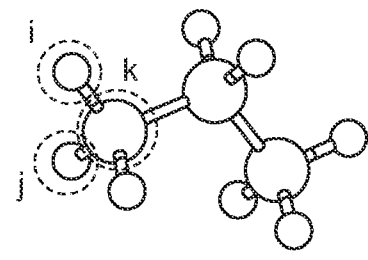
• fragments
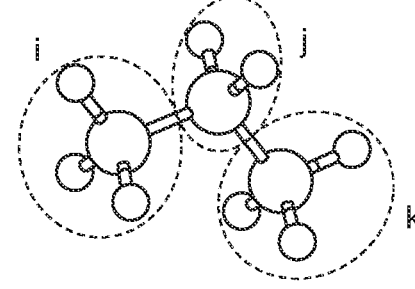
• molecules
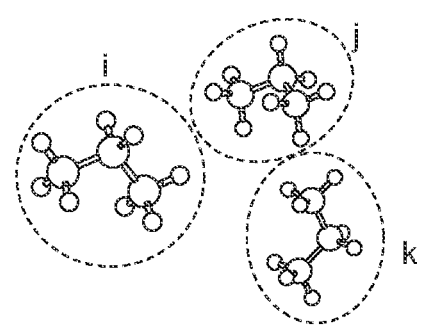
• molecules orbitals
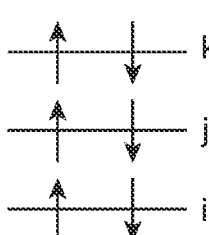
FIG. 12

METHODS AND SYSTEMS FOR QUANTUM COMPUTING ENABLED MOLECULAR AB INITIO SIMULATIONS

CROSS-REFERENCE

This application is a continuation of International Application No. PCT/CA2020/050641, filed May 12, 2020, which claims the benefit of U.S. Provisional Application Ser. No. 62/949,263, filed Dec. 17, 2019, and U.S. Provisional Application Ser. No. 62/847,141, filed May 13, 2019, each of which is entirely incorporated herein by reference for all purposes.

BACKGROUND

In chemistry and biology, the identification and the prediction of the electronic structure and the most energetically stable conformers of a molecule have significant importance as molecular function is inherently embedded in molecular conformation. For example, the reaction rate in a catalyzed reaction can vary significantly based on which of several different conformations of the catalyst are used. As another example, a protein is more functional or functional at all when it forms a certain tertiary structure.

In order to accurately identify and predict the electronic structure and the most stable conformers, highly accurate quantum chemistry methods, such as Coupled-Cluster theory (CC) or Full Configuration Interaction (Full CI), may be performed. However, the computational costs of such methods can exponentially increase with the size of a molecule, and they often become intractable in cases where the size of a molecule exceeds about 50 atoms for CC, and about 10 atoms for Full CI, even when performed on some current state-of-the-art classical computers. Therefore, a highly efficient and accurate computational framework is needed to identify the most stable conformers of industry-relevant chemical compounds and biologically-relevant large molecules.

Quantum computing (QC) technology may be capable of computing the quantum mechanical energy and/or electronic structure of a molecule with exponentially less computational resources compared to classical computing. Thus, high-accuracy quantum chemistry calculations that are intractable using classical computing may become tractable using the QC approaches. However, QC approaches may face challenges, such as the high expense and rarity of QC resources. In addition, increasing the number of qubits in a quantum computer is a technologically challenge, which has limited the size of quantum computing devices. In addition, qubits are very sensitive to noise and environmental effects, which may cause them to decohere in a very short amount of time, thereby providing a relatively small window for running meaningful calculations.

SUMMARY

Recognized herein is the need for quantum algorithms and circuits that efficiently leverage current and near-term quantum computing systems to solve complex quantum chemistry problems. One approach is to decompose an industry-sized problem into subproblems, identify the more complex subproblems, and then use quantum computers to process a subset of problems, for example, those subproblems that are challenging for classical computers.

Systems and methods provided herein utilize problem decomposition (PD) techniques in quantum chemistry toward identification and prediction of the electronic structure and a set of the most energetically stable conformers of a molecule. Such PD techniques may include the fragment molecular orbital (FMO) method, the divide-and-conquer (DC) method, the density matrix embedding theory (DMET) method, the density matrix renormalization group (DMRG) method, tensor networks, the method of increments, and others, as described herein.

In quantum chemistry, PD techniques have been developed to efficiently compute molecular energies and/or electronic structures with reasonable accuracy using classical computing. In PD techniques, the molecule may be decomposed into smaller fragments such that the quantum mechanical energy and/or electronic structure computation becomes tractable for each fragment. The quantum mechanical energy and/or electronic structure computation may then be performed individually for each fragment. The quantum mechanical energy and/or electronic structure computations resulting from each fragment may be recombined into a solution for the original molecule.

Systems and methods provided herein to perform PD techniques on a QC platform may enable quantum mechanical energy and/or electronic structure computations to be performed with a high level of accuracy for each fragment. Further, the small size of each fragment may allow highly accurate computations to be performed on QC devices on which the scale of computations is rather restricted, thereby obtaining the energies and/or electronic structures of complex, industry-relevant molecules efficiently and accurately.

The identification of the electronic structure and the most energetically stable conformers of a molecule is a fundamental process in chemistry- and biology-related research and development. While such processes may be performed by actually synthesizing the molecule and using a variety of physicochemical measurements to identify its electronic structure and conformations, such experimental processes may require a very large amount of resources, such as human effort and time. Thus, highly efficient, and accurate computational methods and systems, such as those provided by the present disclosure, may significantly reduce the need for such resources and render common R&D processes more efficient. Further, methods and systems described herein can be applied not simply to single chemical systems structures (e.g., chemical compounds and biomolecules) but also to molecular aggregates with different associations. For example, methods and systems disclosed herein may be applied toward the identification of the most stable binding orientation of a drug candidate, relative to a target protein, determined from an ensemble of possible binding orientations.

The present disclosure provides methods and systems for using a hybrid architecture of quantum and classical computing processors to efficiently identify the electronic structure and the stable conformations of a chemical system (e.g., a molecule). A method may comprise obtaining an indication of a molecule; calculating or obtaining an ensemble of conformations of the molecule; and decomposing the chemical system into fragments (subsystems) for each conformation (which may be optionally stored in a list). The method may further comprise calculating the fermionic Hamiltonian (molecular Hamiltonian or electronic Hamiltonian) of each fragment of each conformation of the molecule; transforming each fermionic Hamiltonian to an equivalent qubit Hamiltonian; transforming the qubit Hamiltonian into a quantum circuit; calculating an initial state for qubits involved in the calculation of the total quantum mechanical energy and/or electronic structure; generating (e.g., through computational simulation) molecular quantum mechanical energy and/or electronic structure on a quantum hardware or classical simulator of a quantum circuit; and combining the energies and/or electronic structures for the plurality of the fragments to obtain an estimation of the total energy of the chemical system. The method may further comprise repeating these operations for all conformations in the ensemble of conformations and sorting the conformations in the ensemble of conformations based on the estimated total quantum mechanical energy and/or electronic structure. The method may further comprise providing an indication of the sorted conformation ensemble (e.g., in a list).

In one aspect, the present disclosure provides a method for performing a quantum mechanical energy or electronic structure calculation for a chemical system, the method being implemented by a hybrid computing unit comprising a classical computer and a distributed computing system comprising a plurality of one non-classical computers, the method comprising: (a) decomposing at least one conformation within an ensemble of conformations of the chemical system into a plurality of molecular fragments; (b) determining, using the hybrid computing unit, quantum mechanical energies or electronic structures of each of at least a subset of the plurality of molecular fragments; (c) combining the quantum mechanical energies or electronic structure determined in (b); and (d) electronically outputting a report indicative of the quantum mechanical energies or electronic structure combined in (c).

In some embodiments, the plurality of non-classical computers comprises at least one quantum computer. In some embodiments, the at least one quantum computer comprises one or more members selected from the group consisting of a quantum hardware device and a classical simulator of a quantum circuit. In some embodiments, a quantum mechanical energy of the quantum mechanical energies comprises nuclear-nuclear repulsion energy.

In some embodiments, the method further comprises providing an input to the hybrid computing unit, the input comprising a set of atomic coordinates for the chemical system. In some embodiments, the method further comprises performing (a)-(c) for two or more conformations within the ensemble of conformations of the chemical system. In some embodiments, the method further comprises sorting the combined quantum mechanical energies or electronic structures of the at least the subset of the plurality of molecular fragments.

In some embodiments, (a) comprises applying one or more members selected from the group consisting of: a fragment molecular orbital (FMO) method, a divide-and-conquer (DC) method, a density matrix embedding theory (DMET) method, a density matrix renormalization group (DMRG) method, a tensor network, and a method of increments.

In some embodiments, (d) comprises: determining a fermionic Hamiltonian (molecular Hamiltonian or electronic Hamiltonian) of a molecular fragment of the at least the subset of the plurality of molecular fragments; transforming the fermionic Hamiltonian into an equivalent qubit Hamiltonian; transforming the qubit Hamiltonian into a quantum circuit; and determining, using the quantum circuit, the quantum mechanical energy or electronic structure of the molecular fragment. In some embodiments, the method further comprises determining the quantum mechanical energy or electronic structure using a molecular Hamiltonian. In some embodiments, the method further comprises determining the quantum mechanical energy or electronic structure using an electronic Hamiltonian. In some embodiments, transforming the fermionic Hamiltonian into an equivalent qubit Hamiltonian comprises transforming a fermionic operator of a Hamiltonian to a qubit operator.

In some embodiments, the method further comprises performing ab initio molecular dynamics (AIMD) simulation of the chemical system. In some embodiments, the AIMD simulation comprises: prior to (a), obtaining an indication of a chemical system, the indication comprising coordinates of each particle of a plurality of particles in the chemical system and velocities of each particle in the chemical system; and subsequent to (c): (i) determining, from the combined energy or electronic structure, a force on each particle in the systems; (ii) updating the coordinates of each particles in the chemical system and the velocities of each particle in the chemical system; and (iii) electronically outputting a report indicative of the coordinates or velocities. In some embodiments, (i) comprises applying Jordan's quantum algorithm for numerical gradient estimation to the quantum mechanical energy or electronic structure. In some embodiments, (ii) comprises applying one or more members selected from the group consisting of: a Verlet procedure, a velocity Verlet procedure, symplectic integration, Runge-Kutta integration, and Beeman integration.

In another aspect, a system for performing a quantum mechanical energy or electronic structure calculation for a chemical system may comprise: memory comprising instructions for performing the quantum mechanical energy or electronic structure calculation for the chemical system; and a hybrid computing unit operatively coupled to the memory, wherein the hybrid computing unit comprises at least one classical computer and a distributed computing system comprising a plurality of non-classical computers, wherein the hybrid computing unit is configured to execute the instructions to at least: (a) decompose at least one conformation within an ensemble of conformations of the chemical system into a plurality of molecular fragments; (b) determine quantum mechanical energies or electronic structures of at least a subset of the plurality of molecular fragments; (c) combine the quantum mechanical energies or electronic structures determined in (b); and (d) electronically output a report indicative of the quantum mechanical energies or electronic structures combined in (c).

In another aspect, a non-transitory computer readable medium may comprise machine-executable code that upon execution by a hybrid computing unit comprising at least one classical computer and a distributed computing system comprising a plurality of non-classical computers, implements a method for performing a quantum mechanical energy or electronic structure calculation for a chemical system, the method comprising: (a) decomposing at least one conformation within an ensemble of conformations of the chemical system into a plurality of molecular fragments; (b) determining quantum mechanical energies or electronic structures of at least a subset of the plurality of molecular fragments; (c) combining the quantum mechanical energies or electronic structures determined in (b); and (d) electronically outputting a report indicative of the quantum mechanical energies or electronic structures combined in (c).

In another aspect, the present disclosure provides a method for performing a quantum mechanical energy or electronic structure calculation for a chemical system, the method being implemented by a hybrid computing unit comprising a distributed computing system comprising a plurality of classical computers and at least one non-classical computer, the method comprising: (a) decomposing at least one conformation within an ensemble of conformations of the chemical system into a plurality of molecular fragments; (b) determining, using the hybrid computing unit, quantum mechanical energies or electronic structures of at least a subset of the plurality of molecular fragments; (c) combining the quantum mechanical energies or electronic structures determined in (b); and (d) electronically outputting a report indicative of the quantum mechanical energies or electronic structures combined in (c).

In some embodiments, the at least one non-classical computer comprises at least one quantum computer. In some embodiments, the at least one quantum computer comprises one or more members selected from the group consisting of a quantum hardware device and a classical simulator of a quantum circuit. In some embodiments, a quantum mechanical energy of the quantum mechanical energies comprises nuclear-nuclear repulsion energy.

In some embodiments, the method further comprises providing an input to the hybrid computing unit, the input comprising a set of atomic coordinates for the chemical system. In some embodiments, the method further comprises performing (a)-(c) for two or more conformations within the ensemble of conformations of the chemical system. In some embodiments, the method further comprises sorting the combined quantum mechanical energies or electronic structures of the at least the subset of the plurality of molecular fragments.

In some embodiments, (a) comprises applying one or more members selected from the group consisting of: a fragment molecular orbital (FMO) method, a divide-and-conquer (DC) method, a density matrix embedding theory (DMET) method, a density matrix renormalization group (DMRG) method, a tensor network, and a method of increments.

In some embodiments, (b) comprises: determining a fermionic Hamiltonian (molecular Hamiltonian or electronic Hamiltonian) of a molecular fragment of the at least the subset of the plurality of molecular fragments; transforming the fermionic Hamiltonian into an equivalent qubit Hamiltonian; transforming the qubit Hamiltonian into a quantum circuit; and determining, using the quantum circuit, the quantum mechanical energy or electronic structure of the molecular fragment. In some embodiments, the method further comprises determining the quantum mechanical energy or electronic structure using a molecular Hamiltonian. In some embodiments, the method further comprises determining the quantum mechanical energy or electronic structure using an electronic Hamiltonian. In some embodiments, transforming the fermionic Hamiltonian into an equivalent qubit Hamiltonian comprises transforming a fermionic operator of a Hamiltonian to a qubit operator.

In some embodiments, the method further comprises performing ab initio molecular dynamics (AIMD) simulation of the chemical system. In some embodiments, the AIMD simulation comprises: prior to (a), obtaining an indication of a chemical system, the indication comprising coordinates of each particle of a plurality of particles in the chemical system and velocities of each particle in the chemical system; and subsequent to (c): (i) determining, from the combined energy or electronic structure, a force on each particle in the systems; (ii) updating the coordinates of each particles in the chemical system and the velocities of each particle in the chemical system; and (iii) electronically outputting a report indicative of the coordinates or velocities. In some embodiments, (i) comprises applying Jordan's quantum algorithm for numerical gradient estimation to the quantum mechanical energy or electronic structure. In some embodiments, (ii) comprises applying one or more members selected from the group consisting of: a Verlet procedure, a velocity Verlet procedure, symplectic integration, Runge-Kutta integration, and Beeman integration.

In some embodiments, the method further comprises dispatching one or more of the plurality of fragments to one or more remote endpoints and receiving the quantum mechanical energies or electronic structures from the one or more remote endpoints. In some embodiments, at least one of the one or more remote endpoints comprises a non-classical computer. In some embodiments, the one or more remote endpoints comprises portions of a cloud computing system. In some embodiments, the method further comprises, prior to (a), receiving the at least one conformation from a client-side library and dispatching the at least one conformation to a first remote endpoint. In some embodiments, at least one of (a) and (c) occurs at the first remote endpoint. In some embodiments, the method further comprises dispatching one or more of the plurality of fragments to one or more remote second endpoints and receiving the quantum mechanical energies or electronic structures from the second one or more remote endpoints. In some embodiments, the method further comprises transmitting the report to the client-side library. In some embodiments, at least one of the second remote endpoints comprises a non-classical computer. In some embodiments, the one or more remote endpoints comprise portions of a cloud computing system.

In another aspect, a system for performing a quantum mechanical energy or electronic structure calculation for a chemical system may comprise: computer memory comprising instructions for performing the quantum mechanical energy or electronic structure calculation for the chemical system; and a hybrid computing unit operatively coupled to the memory, wherein the hybrid computing unit comprises a distributed computing system comprising a plurality of classical computers and at least one non-classical computer, wherein the hybrid computing unit is configured to execute the instructions to at least: (a) decompose at least one conformation within an ensemble of conformations of the chemical system into a plurality of molecular fragments; (b) determine quantum mechanical energies or electronic structures of at least a subset of the plurality of molecular fragments; (c) combine the quantum mechanical energies or electronic structures determined in (b); and (d) electronically output a report indicative of the quantum mechanical energies or electronic structures combined in (c).

In another aspect, a non-transitory computer readable medium may comprise machine-executable code that upon execution by a hybrid computing unit comprising a distributed computing system comprising a plurality of classical computers and at least one non-classical computer, implements a method for performing a quantum mechanical energy or electronic structure calculation for a chemical system, the method comprising: (a) decomposing at least one conformation within an ensemble of conformations of the chemical system into a plurality of molecular fragments; (b) determining quantum mechanical energies or electronic structures of at least a subset of the plurality of molecular fragments; (c) combining the quantum mechanical energies or electronic structures determined in (b); and (d) electronically outputting a report indicative of the quantum mechanical energies or electronic structures combined in (c).

In another aspect, a method for performing a quantum mechanical energy or electronic structure calculation for a chemical system is provided. The method may be implemented by a hybrid computing unit comprising at least one classical computer and a distributed computing system comprising a plurality of non-classical computers. The method may comprise: (a) decomposing at least one conformation within an ensemble of conformations of said chemical system into a plurality of molecular fragments; (b) determining, using said hybrid computing unit, quantum mechanical energies or electronic structures of at least a subset of said plurality of molecular fragments; (c) combining said quantum mechanical energies or electronic structures determined in (b); and (d) electronically outputting a report indicative of said quantum mechanical energies or electronic structures combined in (c).

In some embodiments, said plurality of non-classical computers comprises at least one quantum computer. In some embodiments, said at least one quantum computer comprises one or more members selected from the group consisting of: a quantum hardware device and a classical simulator of a quantum circuit. In some embodiments, said plurality of non-classical computers comprises different types of non-classical computers. In some embodiments, a quantum mechanical energy of said quantum mechanical energies comprises nuclear-nuclear repulsion energy. In some embodiments, the method further comprises providing an input to said hybrid computing unit, said input comprising a set of atomic coordinates for said chemical system. In some embodiments, the method further comprises performing (a)-(c) for two or more conformations within said ensemble of conformations of said chemical system. In some embodiments, the method further comprises sorting said combined quantum mechanical energies or electronic structures of said at least said subset of said plurality of molecular fragments.

In some embodiments, (a) comprises applying one or more members selected from the group consisting of: a fragment molecular orbital (FMO) method, a divide-and-conquer (DC) method, a density matrix embedding theory (DMET) method, a density matrix renormalization group (DMRG) method, a tensor network, and a method of increments. In some embodiments, (b) comprises: determining a fermionic Hamiltonian of a molecular fragment of said at least said subset of said plurality of molecular fragments; transforming said fermionic Hamiltonian into an equivalent qubit Hamiltonian; transforming said qubit Hamiltonian into a quantum circuit; and determining, using said quantum circuit, a quantum mechanical energy or electronic structure of said molecular fragment. In some embodiments, the method further comprises determining said quantum mechanical energy or electronic structure using a molecular Hamiltonian. In some embodiments, the method further comprises determining said quantum mechanical energy or electronic structure using an electronic Hamiltonian. In some embodiments, transforming said fermionic Hamiltonian into an equivalent qubit Hamiltonian comprises transforming a fermionic operator of a Hamiltonian to a qubit operator.

In some embodiments, the method further comprises performing an ab initio molecular dynamics (AIMD) simulation of said chemical system. In some embodiments, said AIMD simulation comprises: prior to (a), obtaining an indication of a chemical system, said indication comprising coordinates of each particle of a plurality of particles in said chemical system and velocities of each particle in said chemical system; and subsequent to (c): (i) determining, from said combined energy or electronic structure, a force on each particle in said chemical system; (ii) updating said coordinates of said each particle in said chemical system and said velocities of said each particle in said chemical system; and (iii) electronically outputting a report indicative of said coordinates or said velocities. In some embodiments, (i) comprises applying Jordan's quantum algorithm for numerical gradient estimation to said quantum mechanical energy or electronic structure. In some embodiments, (ii) comprises applying one or more members selected from the group consisting of: a Verlet procedure, a velocity Verlet procedure, symplectic integration, Runge-Kutta integration, and Beeman integration.

In some embodiments, the method further comprises dispatching one or more of said plurality of fragments to one or more remote endpoints and receiving said quantum mechanical energies or electronic structures from said one or more remote endpoints. In some embodiments, at least one of said one or more remote endpoints comprises a non-classical computer. In some embodiments, said one or more remote endpoints comprise portions of a cloud computing system. In some embodiments, the method further comprises, prior to (a), receiving said at least one conformation from a client-side library and dispatching said at least one conformation to a first remote endpoint. In some embodiments, at least one of (a) and (c) occur at said first remote endpoint.

In some embodiments, the method further comprises dispatching one or more of said plurality of fragments to one or more remote second endpoints and receiving said quantum mechanical energies or electronic structures from said second one or more remote endpoints. In some embodiments, the method further comprises transmitting said report to said client-side library. In some embodiments, at least one of said second remote endpoints comprises a non-classical computer. In some embodiments, said one or more remote endpoints comprise portions of a cloud computing system. In some embodiments, said decomposing in (a) is performed using said at least one classical computer. In some embodiments, said determining in (b) is performed using at least one non-classical computer of said plurality of non-classical computers. In some embodiments, said combining in (c) is performed using said at least one classical computer.

In another aspect a system for performing a quantum mechanical energy or electronic structure calculation for a chemical system is provided. The system may comprise: a hybrid computing unit operatively coupled to said memory, wherein said hybrid computing unit comprises at least one classical computer and a distributed computing system comprising a plurality of non-classical computers, wherein said hybrid computing unit is configured to at least: (a) decompose at least one conformation within an ensemble of conformations of said chemical system into a plurality of molecular fragments; (b) determine quantum mechanical energies or electronic structures of at least a subset of said plurality of molecular fragments; (c) combine said quantum mechanical energies or electronic structures determined in (b); and (d) electronically output a report indicative of said quantum mechanical energies or electronic structures combined in (c).

In some embodiments, the system further comprises computer memory comprising instructions for performing said quantum mechanical energy or electronic structure calculation for said chemical system, wherein said hybrid computing unit is configured to implement said instructions to perform at least (a)-(d).

In another aspect, a non-transitory computer readable medium comprising machine-executable code that upon execution by a hybrid computing unit comprising at least one classical computer and a distributed computing system comprising a plurality of non-classical computers, implements a method for performing a quantum mechanical energy or electronic structure calculation for a chemical system is provided. The method may comprise: (a) decomposing at least one conformation within an ensemble of conformations of said chemical system into a plurality of molecular fragments; (b) determining quantum mechanical energies or electronic structures of at least a subset of said plurality of molecular fragments; (c) combining said quantum mechanical energies or electronic structures determined in (b); and (d) electronically outputting a report indicative of said quantum mechanical energies or electronic structures combined in (c).

In another aspect, a method for performing a quantum mechanical energy or electronic structure calculation for a chemical system is provided. The method may be implemented by a hybrid computing unit comprising a distributed computing system comprising a plurality of classical computers and at least one non-classical computer. The method may comprise: (a) decomposing at least one conformation within an ensemble of conformations of said chemical system into a plurality of molecular fragments; (b) determining, using said hybrid computing unit, quantum mechanical energies or electronic structures of at least a subset of said plurality of molecular fragments; (c) combining said quantum mechanical energies or electronic structures determined in (b); and (d) electronically outputting a report indicative of said quantum mechanical energies or electronic structures combined in (c).

In some embodiments, said at least one non-classical computer comprises at least one quantum computer. In some embodiments, said at least one quantum computer comprises one or more members selected from the group consisting of: a quantum hardware device and a classical simulator of a quantum circuit. In some embodiments, said at least one non-classical computer comprises a plurality of different types of non-classical computers. In some embodiments, an energy of said quantum mechanical energies comprises nuclear-nuclear repulsion energy. In some embodiments, the method further comprises providing an input to said hybrid computing unit, said input comprising a set of atomic coordinates for said chemical system. In some embodiments, the method further comprises performing (a)-(c) for two or more conformations within said ensemble of conformations of said chemical system. In some embodiments, the method further comprises sorting said combined quantum mechanical energies or electronic structures of said at least said subset of said plurality of molecular fragments.

In some embodiments, (a) comprises applying one or more members selected from the group consisting of: a fragment molecular orbital (FMO) method, a divide-and-conquer (DC) method, a density matrix embedding theory (DMET) method, a density matrix renormalization group (DMRG) method, a tensor network, and a method of increments.

In some embodiments, (b) comprises: (i) determining a fermionic Hamiltonian of a molecular fragment of said at least said subset of said plurality of molecular fragments; (ii) transforming said fermionic Hamiltonian into an equivalent qubit Hamiltonian; (iii) transforming said qubit Hamiltonian into a quantum circuit; and (iv) determining, using said quantum circuit, a quantum mechanical energy or electronic structure of said molecular fragment. In some embodiments, the method further comprises determining said quantum mechanical energy or electronic structure using a molecular Hamiltonian. In some embodiments, the method further comprises determining said quantum mechanical energy or electronic structure using an electronic Hamiltonian. In some embodiments, transforming said fermionic Hamiltonian into an equivalent qubit Hamiltonian comprises transforming a fermionic operator of a Hamiltonian to a qubit operator.

In some embodiments, the method further comprises performing an ab initio molecular dynamics (AIMD) simulation of said chemical system. In some embodiments, said AIMD simulation comprises: prior to (a), obtaining an indication of a chemical system, said indication comprising coordinates of each particle of a plurality of particles in said chemical system and velocities of each particle in said chemical system; and subsequent to (c): (i) determining, from said combined energy or electronic structure, a force on each particle in said chemical system; (ii) updating said coordinates of said each particle in said chemical system and said velocities of said each particle in said chemical system; and (iii) electronically outputting a report indicative of said coordinates or said velocities. In some embodiments, (i) comprises applying Jordan's quantum algorithm for numerical gradient estimation to said quantum mechanical energy or electronic structure. In some embodiments, (ii) comprises applying one or more members selected from the group consisting of: a Verlet procedure, a velocity Verlet procedure, symplectic integration, Runge-Kutta integration, and Beeman integration.

In some embodiments, the method further comprises dispatching one or more of said plurality of fragments to one or more remote endpoints and receiving said quantum mechanical energies or electronic structures from said one or more remote endpoints. In some embodiments, at least one of said one or more remote endpoints comprises a non-classical computer. In some embodiments, said one or more remote endpoints comprise portions of a cloud computing system.

In some embodiments, the method further comprises, prior to (a), receiving said at least one conformation from a client-side library and dispatching said at least one conformation to a first remote endpoint. In some embodiments, at least one of (a) and (c) occur at said first remote endpoint. In some embodiments, the method further comprises dispatching one or more of said plurality of fragments to one or more remote second endpoints and receiving said quantum mechanical energies or electronic structures from said second one or more remote endpoints. In some embodiments, the method further comprises transmitting said report to said client-side library. In some embodiments, at least one of said second remote endpoints comprises a non-classical computer. In some embodiments, said one or more remote endpoints comprise portions of a cloud computing system.

In some embodiments, said decomposing in (a) is performed using at least one classical computer of said plurality of classical computers. In some embodiments, said determining in (b) is performed using said at least one non-classical computer. In some embodiments, said combining in (c) is performed using at least one classical computer of said plurality of classical computers.

In another aspect, a system for performing a quantum mechanical energy or electronic structure calculation for a chemical system is provided. The system may comprise: a hybrid computing unit operatively coupled to said memory, wherein said hybrid computing unit comprises a distributed computing system comprising a plurality of classical computers and at least one non-classical computer, wherein said hybrid computing unit is configured to at least: (a) decompose at least one conformation within an ensemble of conformations of said chemical system into a plurality of molecular fragments; (b) determine quantum mechanical energies or electronic structures of at least a subset of said plurality of molecular fragments; (c) combine said quantum mechanical energies or electronic structures determined in (b); and (d) electronically output a report indicative of said quantum mechanical energies or electronic structures combined in (c).

In some embodiments, the system further comprises computer memory comprising instructions for performing said quantum mechanical energy or electronic structure calculation for said chemical system, wherein said hybrid computing unit is configured to implement said instructions to perform at least (a)-(d).

In another aspect, a non-transitory computer readable medium comprising machine-executable code that upon execution by a hybrid computing unit comprising a distributed computing system comprising a plurality of classical computers and at least one non-classical computer, implements a method for performing a quantum mechanical energy or electronic structure calculation for a chemical system is provided. The method may comprise: (a) decomposing at least one conformation within an ensemble of conformations of said chemical system into a plurality of molecular fragments; (b) determining quantum mechanical energies or electronic structures of at least a subset of said plurality of molecular fragments; (c) combining said quantum mechanical energies or electronic structures determined in (d); and (d) electronically outputting a report indicative of said quantum mechanical energies or electronic structures combined in (c).

In another aspect, a method for performing a quantum mechanical energy or electronic structure calculation for a chemical system is provided. The method may be implemented by a hybrid computing unit comprising at least one classical computer and a distributed computing system comprising a plurality of non-classical computers. The method may comprise: (a) decomposing at least one conformation within an ensemble of conformations of said chemical system into a plurality of molecular fragments; (b) dispatching a subset of the plurality of molecular fragments to a plurality of solvers; (c) determining, using said plurality of solvers, quantum mechanical energies or electronic structures of a plurality of molecular fragments of said subset of said plurality of molecular fragments; and (d) electronically outputting a report indicative of said quantum mechanical energies or electronic structures determined in (c).

In some embodiments, said plurality of non-classical computers comprises at least one quantum computer. In some embodiments, said at least one quantum computer comprises one or more members selected from the group consisting of: a quantum hardware device and a classical simulator of a quantum circuit. In some embodiments, said plurality of non-classical computers comprises different types of non-classical computers. In some embodiments, a quantum mechanical energy of said quantum mechanical energies comprises nuclear-nuclear repulsion energy. In some embodiments, the method further comprises: providing an input to said hybrid computing unit, said input comprising a set of atomic coordinates for said chemical system. In some embodiments, the method further comprises performing (a)-(c) for two or more conformations within said ensemble of conformations of said chemical system. In some embodiments, the method further comprises said combined quantum mechanical energies or electronic structures of said at least said subset of said plurality of molecular fragments. In some embodiments, (a) comprises applying one or more members selected from the group consisting of: a fragment molecular orbital (FMO) method, a divide-and-conquer (DC) method, a density matrix embedding theory (DMET) method, a density matrix renormalization group (DMRG) method, a tensor network, and a method of increments.

In some embodiments, (c) comprises: determining a fermionic Hamiltonian of a molecular fragment of said plurality of molecular fragments; transforming said fermionic Hamiltonian into an equivalent qubit Hamiltonian; transforming said qubit Hamiltonian into a quantum circuit; and determining, using said quantum circuit, a quantum mechanical energy or electronic structure of said molecular fragment. In some embodiments, the method further comprises determining said quantum mechanical energy or electronic structure using a molecular Hamiltonian. In some embodiments, the method further comprises determining said quantum mechanical energy or electronic structure using an electronic Hamiltonian. In some embodiments, transforming said fermionic Hamiltonian into an equivalent qubit Hamiltonian comprises transforming a fermionic operator of a Hamiltonian to a qubit operator.

In some embodiments, the method further comprises performing an ab initio molecular dynamics (AIMD) simulation of said chemical system. In some embodiments, said AIMD simulation comprises: prior to (a), obtaining an indication of a chemical system, said indication comprising coordinates of each particle of a plurality of particles in said chemical system and velocities of each particle in said chemical system; and subsequent to (c): (i) determining, from said combined energy or electronic structure, a force on each particle in said chemical system; (ii) updating said coordinates of said each particle in said chemical system and said velocities of said each particle in said chemical system; and (iii) electronically outputting a report indicative of said coordinates or said velocities. In some embodiments, (i) comprises applying Jordan's quantum algorithm for numerical gradient estimation to said quantum mechanical energy or electronic structure. In some embodiments, (ii) comprises applying one or more members selected from the group consisting of: a Verlet procedure, a velocity Verlet procedure, symplectic integration, Runge-Kutta integration, and Beeman integration.

In some embodiments, said plurality of solvers comprises one or more remote endpoints. In some embodiments, the method further comprises receiving said quantum mechanical energies or electronic structures from said one or more remote endpoints. In some embodiments, at least one of said one or more remote endpoints comprises a non-classical computer. In some embodiments, said one or more remote endpoints comprise portions of a cloud computing system.

In some embodiments, the method further comprises, prior to (a), receiving said at least one conformation from a client-side library and dispatching said at least one conformation to a first remote endpoint. In some embodiments, at least one of (a) and (c) occur at said first remote endpoint. In some embodiments, the method further comprises dispatching one or more of said plurality of fragments to one or more remote second endpoints and receiving said quantum mechanical energies or electronic structures from said second one or more remote endpoints. In some embodiments, the method further comprises transmitting said report to said client-side library. In some embodiments, at least one of said second remote endpoints comprises a non-classical computer. In some embodiments, said one or more remote endpoints comprises portions of a cloud computing system.

In some embodiments, said decomposing in (a) is performed using said at least one classical computer. In some embodiments, said dispatching in (b) is preformed using said at least one classical computer. In some embodiments, said dispatching in (b) is preformed using a classical computer remote from said at least one classical computer. In some embodiments, said determining in (c) is performed using at least one non-classical computer of said plurality of non-classical computers. In some embodiments, said outputting in (d) is performed using said at least one classical computer.

In another aspect, a system for performing a quantum mechanical energy or electronic structure calculation for a chemical system is provided. The system may comprise: a hybrid computing unit operatively coupled to said memory, wherein said hybrid computing unit comprises a distributed computing system comprising a plurality of classical computers and at least one non-classical computer, wherein said hybrid computing unit is configured to at least: (a) decompose at least one conformation within an ensemble of conformations of said chemical system into a plurality of molecular fragments; (b) dispatch a subset of the plurality of molecular fragments to a plurality of solvers; (c) determine, using said plurality of solvers, quantum mechanical energies or electronic structures of a plurality of molecular fragments of said subset of said plurality of molecular fragments; and (d) electronically output a report indicative of said quantum mechanical energies or electronic structures determined in (c). In some embodiments, the system further comprises: computer memory comprising instructions for performing said quantum mechanical energy or electronic structure calculation for said chemical system, wherein said hybrid computing unit is configured to implement said instructions to perform at least (a)-(d).

In another aspect, a non-transitory computer readable medium comprising machine-executable code that upon execution by a hybrid computing unit comprising a distributed computing system comprising a plurality of classical computers and at least one non-classical computer, implements a method for performing a quantum mechanical energy or electronic structure calculation for a chemical system is provided. The method may comprise: (a) decomposing at least one conformation within an ensemble of conformations of said chemical system into a plurality of molecular fragments; (b) determining quantum mechanical energies or electronic structures of at least a subset of said plurality of molecular fragments; (c) combining said quantum mechanical energies or electronic structures determined in (d); and (d) electronically outputting a report indicative of said quantum mechanical energies or electronic structures combined in (c).

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2 illustrates a flowchart for an example of a method for providing an indication of the quantum mechanical energy and/or electronic structure of a subsystem, which is defined by problem decomposition techniques, on quantum computing hardware, in accordance with some embodiments disclosed herein.

FIG. 6 is an example illustration of n-heptane, showing the minimal sphere (dotted circle) to accommodate the conformer, and the distance (solid line) between the end carbon-atoms involved in a dihedral angle (1-4 distance) [left]; a plot showing the relation between the total quantum mechanical energy (left arrow) and the diameter of the minimal sphere (right arrow) for each of the conformers, which are sorted based on the total quantum mechanical energy [middle]; and a plot showing the relation between the total quantum mechanical energy (left arrow) and the smallest 1-4 distance (right arrow) for each conformer [right].

FIG. 12 illustrates molecular orbitals, atoms, molecular fragments, and molecules used as bases for the method of increments.

DETAILED DESCRIPTION

Figure 1:
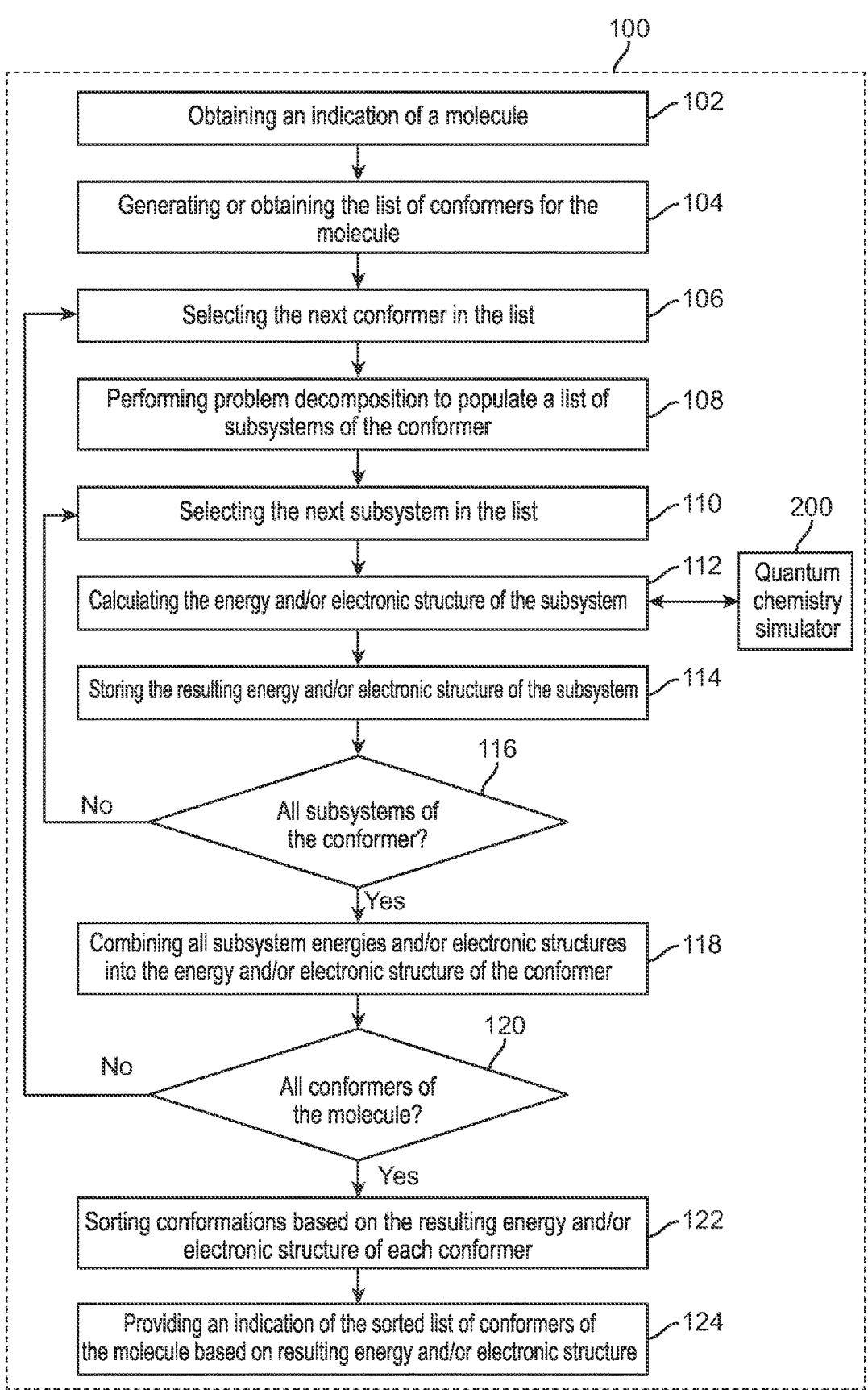
FIG. 1 illustrates a flowchart for an example of a method for providing an indication of a sorted list of conformers of a molecule using problem decomposition techniques on quantum computing hardware, in accordance with some embodiments disclosed herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present disclosure provides methods of applying problem decomposition (PD) techniques in quantum chemistry toward identification and prediction of the quantum mechanical energy and/or electronic structure of a chemical system or to identify a set of the most energetically stable conformers of a molecule. Systems and methods provided herein to perform PD techniques on a QC platform may enable quantum mechanical energy and/or electronic structure computations to be performed with a high level of accuracy for each fragment. Further, the small size of each fragment may allow highly accurate computations to be performed on QC devices on which the scale of computations is rather restricted, thereby obtaining the energies and/or electronic structures of complex, industry-relevant molecules efficiently and accurately. Methods and systems described herein can be applied not simply to single chemical systems but also to molecular aggregates with different association structures. For example, methods and systems disclosed herein may be applied toward the identification of the most stable binding orientation of a drug candidate to a target protein from the ensemble of possible binding orientations.

In some cases, a classical computer may be configured to perform one or more classical algorithms. A classical algorithm (or classical computational task) may comprise an algorithm (or computational task) that is able to be executed by one or more classical computers without the use of a quantum computer, a quantum-ready computing service, or a quantum-enabled computing service. A classical algorithm may comprise a non-quantum algorithm. A classical computer may comprise a computer which does not comprise a quantum computer, a quantum-ready computing service, or a quantum-enabled computer. A classical computer may process, or store data represented by digital bits (e.g., zeroes ("0") and ones ("1")) rather than quantum bits (qubits). Examples of classical computers include, but are not limited to, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles.

The hybrid computing unit may comprise a classical computer and quantum computer. The quantum computer may be configured to perform one or more quantum algorithms for solving a computational problem (e.g., at least a portion of a quantum chemistry simulation). The one or more quantum algorithms may be executed using a quantum computer, a quantum-ready computing service, or a quantum-enabled computing service. For instance, the one or more quantum algorithms may be executed using the systems or methods described in U.S. Patent Publication No. 2018/0107526, entitled "METHODS AND SYSETMS FOR QUANTUM READY AND QUANTUM ENABLED COMPUTATIONS", which is entirely incorporated herein by reference. The classical computer may comprise at least one classical processor and computer memory and may be configured to perform one or more classical algorithms for solving a computational problem (e.g., at least a portion of a quantum chemistry simulation). The digital computer may comprise at least one computer processor and computer memory, wherein the digital computer may include a computer program with instructions executable by the at least one computer processor to render an application. The application may facilitate use of the quantum computer and/or the classical computer by a user.

Some implementations may use quantum computers along with classical computers operating on bits, such as personal desktops, laptops, supercomputers, distributed computing, clusters, cloud-based computing resources, smartphones, or tablets.

The system may comprise an interface for a user. In some cases, the interface may comprise an application programming interface (API). The interface may provide a programmatic model that abstracts away (e.g., by hiding from the user) the internal details (e.g., architecture and operations) of the quantum computer. In some cases, the interface may minimize a need to update the application programs in response to changing quantum hardware. In some cases, the interface may remain unchanged when the quantum computer has a change in internal structure.

The present disclosure provides systems and methods that may include non-classical (e.g., quantum) computing or use of non-classical (e.g., quantum) computing. Quantum computers may be able to solve certain classes of computational tasks more efficiently than classical computers. However, quantum computation resources may be rare and expensive, and may involve a certain level of expertise to be used efficiently or effectively (e.g., cost-efficiently or cost-effectively). A number of parameters may be tuned in order for a quantum computer to deliver its potential computational power.

Quantum computers (or other types of non-classical computers) may be able to work alongside classical computers as co-processors. A hybrid architecture (e.g., computing system) comprising a classical computer and a quantum computer can be very efficient for addressing complex computational tasks, such as quantum chemistry simulations. Systems and methods disclosed herein may be able to efficiently and accurately decompose or break down a quantum chemistry problem and delegate appropriate components of the quantum chemistry simulations to the quantum computer or the classical computer.

Although the present disclosure has referred to quantum computers, methods and systems of the present disclosure may be employed for use with other types of computers, which may be non-classical computers. Such non-classical computers may comprise quantum computers, hybrid quantum computers, quantum-type computers, or other computers that are not classical computers. Examples of non-classical computers may include, but are not limited to, Hitachi Ising solvers, coherent Ising machines based on optical parameters, and other solvers which utilize different physical phenomena to obtain more efficiency in solving particular classes of problems.

In some cases, a quantum computer may comprise one or more adiabatic quantum computers, quantum gate arrays, one-way quantum computers, topological quantum computers, quantum Turing machines, superconductor-based quantum computers, trapped ion quantum computers, trapped atom quantum computers, optical lattices, quantum dot computers, spin-based quantum computers, spatial-based quantum computers, Loss-DiVincenzo quantum computers, nuclear magnetic resonance (NMR) based quantum computers, solution-state NMR quantum computers, solid-state NMR quantum computers, solid-state NMR Kane quantum computers, electrons-on-helium quantum computers, cavity-quantum-electrodynamics based quantum computers, molecular magnet quantum computers, fullerene-based quantum computers, linear optical quantum computers, diamond-based quantum computers, nitrogen vacancy (NV) diamond-based quantum computers, Bose-Einstein condensate-based quantum computers, transistor-based quantum computers, and rare-earth-metal-ion-doped inorganic crystal based quantum computers. A quantum computer may comprise one or more of: quantum annealers, Ising solvers, optical parametric oscillators (OPO), and gate models of quantum computing.

In some cases, a non-classical computer of the present disclosure may comprise a noisy intermediate-scale quantum device. The term Noisy Intermediate-Scale Quantum (NISQ) was introduced by John Preskill in "Quantum Computing in the NISQ era and beyond." arXiv:1801.00862. Here, "Noisy" may imply that incomplete control over the qubits is present and the "Intermediate-Scale" may refer to the number of qubits which may range from 50 to a few hundreds. Several physical systems made from superconducting qubits, artificial atoms, ion traps are proposed so far as feasible candidates to build NISQ quantum device and ultimately universal quantum computers.

In some cases, a classical simulator of the quantum circuit can be used which can run on a classical computer like a MacBook Pro laptop, a Windows laptop, or a Linux laptop. In some cases, the classical simulator can run on a cloud computing platform having access to multiple computing nodes in a parallel or distributed manner. In some cases, all or a portion of a quantum mechanical energy and/or electronic structure calculation may be performed using the classical simulator.

The methods described herein may be performed on an analogue quantum simulator. An analogue quantum simulator may be a quantum mechanical system consisting of a plurality of manufactured qubits. An analogue quantum simulator may be designed to simulate quantum systems by using physically different but mathematically equivalent or approximately equivalent systems. In an analogue quantum simulator, each qubit may be realized in an ion of strings of trapped atomic ions in linear radiofrequency traps. To each qubit may be coupled a source of bias called a local field bias. The local field biases on the qubits may be programmable and controllable. In some cases, a qubit control system comprising a digital processing unit is connected to the system of qubits and is capable of programming and tuning the local field biases on the qubits.

Classical Computer

In some cases, the systems, media, networks, and methods described herein comprise a classical computer, or use of the same. In some cases, the classical computer includes one or more hardware central processing units (CPUs) that carry out the classical computer's functions. In some cases, the classical computer further comprises an operating system (OS) configured to perform executable instructions. In some cases, the classical computer is connected to a computer network. In some cases, the classical computer is connected to the Internet such that it accesses the World Wide Web. In some cases, the classical computer is connected to a cloud computing infrastructure. In some cases, the classical computer is connected to an intranet. In some cases, the classical computer is connected to a data storage device.

In accordance with the description herein, suitable classical computers may include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Smartphones may be suitable for use with methods and systems described herein. Select televisions, video players, and digital music players, in some cases with computer network connectivity, may be suitable for use in the systems and methods described herein. Suitable tablet computers may include those with booklet, slate, and convertible configurations.

In some cases, the classical computer includes an operating system configured to perform executable instructions. The operating system may be, for example, software, including programs and data, which manages the device's hardware and provides services for execution of applications. Suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Suitable personal computer operating systems may include, by way of non-limiting examples, Microsoft® Windows®, Apple® Mac OS X®, UNIX®, and UNIX-like operating systems such as GNU/Linux®. In some cases, the operating system is provided by cloud computing. Suitable mobile smart phone operating systems may include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Suitable media streaming device operating systems may include, by way of non-limiting examples, Apple TV®, Roku®, Boxee®, Google TV®, Google Chromecast®, Amazon Fire®, and Samsung® HomeSync®. Suitable video game console operating systems may include, by way of non-limiting examples, Sony® PS3®, Sony® PS4®, Microsoft® Xbox 360®, Microsoft Xbox One, Nintendo® Wii®, Nintendo® Wii UR, and Ouya®.

In some cases, the classical computer includes a storage and/or memory device. In some cases, the storage and/or memory device is one or more physical apparatuses used to store data or programs on a temporary or permanent basis. In some cases, the device is volatile memory and requires power to maintain stored information. In some cases, the device is non-volatile memory and retains stored information when the classical computer is not powered. In some cases, the non-volatile memory comprises flash memory. In some cases, the non-volatile memory comprises dynamic random-access memory (DRAM). In some cases, the non-volatile memory comprises ferroelectric random access memory (FRAM). In some cases, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In some cases, the storage and/or memory device is a combination of devices such as those disclosed herein.

In some cases, the classical computer includes a display to send visual information to a user. In some cases, the display is a cathode ray tube (CRT). In some cases, the display is a liquid crystal display (LCD). In some cases, the display is a thin film transistor liquid crystal display (TFT-LCD). In some cases, the display is an organic light emitting diode (OLED) display. In some cases, on OLED display is a passive-matrix OLED (PMOLED) or active-matrix OLED (AMOLED) display. In some cases, the display is a plasma display. In other embodiments, the display is a video projector. In some cases, the display is a combination of devices such as those disclosed herein.

In some cases, the classical computer includes an input device to receive information from a user. In some cases, the input device is a keyboard. In some cases, the input device is a pointing device including, by way of non-limiting examples, a mouse, trackball, track pad, joystick, game controller, or stylus. In some cases, the input device is a touch screen or a multi-touch screen. In some cases, the input device is a microphone to capture voice or other sound input. In some cases, the input device is a video camera or other sensor to capture motion or visual input. In some cases, the input device is a Kinect, Leap Motion, or the like. In some cases, the input device is a combination of devices such as those disclosed herein.

Non-Transitory Computer Readable Storage Medium

In some cases, the systems and methods described herein include one or more non-transitory computer readable storage media encoded with a program including instructions executable by the operating system of an optionally networked digital processing device. In some cases, a computer readable storage medium is a tangible component of a classical computer. In some cases, a computer readable storage medium is optionally removable from a classical computer. In some cases, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Embodiments of the disclosed method for efficiently identifying the stable conformations of a chemical system are described below.

Identification of a Target Chemical System

A hybrid computing unit comprising a classical computer and a quantum computer may be used to perform a quantum mechanical energy and/or electronic structure calculation for a chemical system. For example, such a hybrid computing unit may be used to perform a method for efficiently identifying the stable conformations of a chemical system (e.g., a molecule).

FIG. 1 illustrates a flowchart for an example of a method 100 for providing an indication of a sorted list of conformers of a molecule using problem decomposition techniques on quantum computing hardware.

The method 100 may comprise obtaining an indication of an input molecule according to operation 102. The method 100 disclosed herein may be applicable to any type of chemical system. The chemical system may comprise, for example, an organic compound, an inorganic compound, a polymer, a peptide, a polypeptide, a protein, a nucleic acid, a carbohydrate, etc. Methods disclosed herein may also be applicable to complexes of molecules, such as one or more protein-drug complex (including or excluding solvent molecules).

Generation of an Ensemble of Conformers

The method 100 may comprise determining an ensemble of conformations of the chemical system. For example, the method 100 may comprise generating an ensemble (e.g., list) of conformers for the input chemical system according to operation 104. A variety of different approaches may be used to enumerate conformers for a chemical system. In some cases, an exhaustive conformation sampler can be used, in which the conformation of the molecule is sampled by varying all the dihedral angles around the rotatable bonds in the chemical system. In some cases, Monte Carlo simulation or molecular dynamics simulation may be performed to generate the ensemble of conformers. In another embodiment, the ensemble of conformers for the molecule is as an input together with the chemical system information.

Selection and Processing of Conformers from the Ensemble of Conformers

The method 100 may comprise, according to operation 106, selecting a conformer from the ensemble or list (e.g., ordered list) of conformers, and performing any at least 1, 2, 3, 4, 5, 6, or 7, or at most any 7, 6, 5, 4, 3, 2, or 1 of operations 108, 110, 112, 114, 116, 118, and/or 120 for the conformed select. Any at least 1, 2, 3, 4, 5, 6, or 7, or at most any 7, 6, 5, 4, 3, 2, or 1 of operations 108, 110, 112, 114, 116, 118, and/or 120 may be performed for each conformer in the ensemble of conformers.

(a) PD Frag-Mentation of a Chemical System

The method 100 may comprise decomposing at least one conformation within the ensemble into a plurality of molecular fragments. For example, the method 100 may comprise decomposing (e.g., performing problem decomposition on) the chemical system into a plurality (e.g., a list) of smaller fragments or subsystems according to operation 108. The specific scheme for decomposing the system into subsystems may vary depending on the PD technique used. Generally, a suitable PD fragment ("fragment") size may be selected such that the computational resources required to process the fragment do not exceed the capability of the quantum-classical hardware to be used.

Various fragmentation approaches for chemical systems may be suitable for use, including but not limited to: (i) Divide and Conquer (DC), (ii) Fragment Molecular Orbitals (FMO), (iii) Density Matrix Embedding Theory (DMET), (iv) Density Matrix Renormalization Group (DMRG), (v) Tensor Networks, (vi) the method of increments (as described herein with respect to FIG. 11), and others.

For example, the FMO method was first described by Kitaura et al., "Fragment molecular orbital method: an approximate computational method for large molecules," *Chemical Physics Letters,* 1999, 313, 701, which is hereby incorporated by reference in its entirety. The FMO method has been applied to many systems, such as those described by Fedorov et al., "Exploring chemistry with the fragment molecular orbital method," *Physical Chemistry Chemical-Physics,* 2012, 14, 7562, which is hereby incorporated by reference in its entirety.

For example, the DC method was first described by Yang, "Direct calculation of electron density in density-functional theory: Implementation for benzene and a tetrapeptide," *Physical Review A,* 1991, 44, 7823, which is hereby incorporated by reference in its entirety. The DC method has been further developed and described, for example, by Akama et al., "Implementation of divide-and-conquer method including Hartree-Fock exchange interaction," *Journal of Computational Chemistry,* 2007, 28, 2003 and Kobayashi et al., "Divide-and-conquer approaches to quantum chemistry: Theory and implementation," in *Linear-Scaling Techniques in Computational Chemistry and Physics: Methods and Applications,* edited by Zalesny et al. (Springer Netherlands, Dordrecht, 2011), 97-127, each of which is hereby incorporated by reference in its entirety.

For example, DMET was first described by Knizia et al., "Density Matrix Embedding: A Simple Alternative to Dynamical Mean-Field Theory," *Physical Review Letters,* 2012, 109, 186404, which is hereby incorporated by reference in its entirety. DMET was further developed and described, for example, by Wouters et al., "A Practical Guide to Density Matrix Embedding Theory in Quantum Chemistry," *Journal of Chemical Theory and Computation,* 2016, 12, 2706, which is hereby incorporated by reference in its entirety.

For example, DMRG was first described by Steven R. White "Density Matrix Formulation for Quantum Renormalization Groups," *Physical Review Letters,* 1992, 69, 2863, which is hereby incorporated by reference in its entirety. A review of DMRG is provided by Ulrich Schollwock, arxiv.org:cond-mat/0409292 [cond-mat.str-el] or *Review of Modern Physics,* 2005, 77, 259, which is hereby incorporated by reference in its entirety.

For example, tensor networks may be mathematical representations of quantum many-body states based on their entanglement structure. Different tensor network structures describe different physical situations, such as low-energy states of gapped 1D systems, 2D systems and scale-invariant systems. A tensor network may represent a quantum state as one or more matrix product states. A review of tensor networks is provided by Roman Orus "Tensor networks for complex quantum systems," *Nature Reviews Physics,* 2019, 1, 538, which is hereby incorporated by reference in its entirety.

Figure 11:
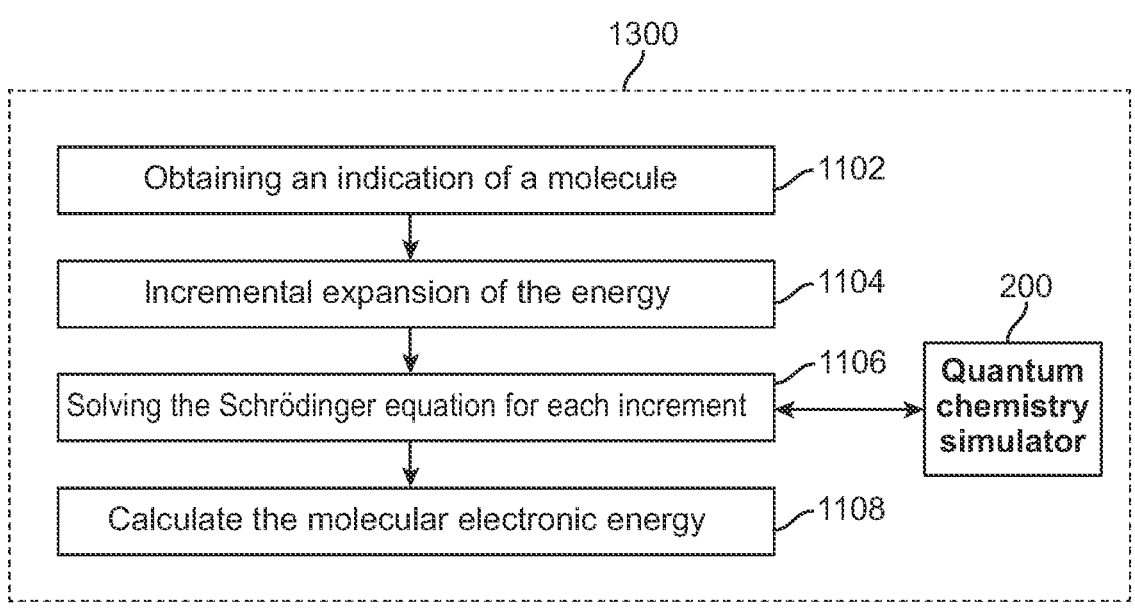
FIG. 11 illustrates a flowchart for an example of a method of increments for performing problem decomposition.

FIG. 11 illustrates a flowchart for an example of a method 1100 of increments for performing problem decomposition. The method 1100 may be referred to as a "method of increments" in general or may be variously referred depending on the quantum chemistry method utilized. For example, the utilization of unitary coupled cluster (UCC) method in the method of increments may be referred to as "incremental unitary coupled-cluster" (iUCC) method. The method 1100 may comprise obtaining an indication of a molecule according to operation 1102. The method 1100 disclosed herein may be applicable to any type of molecule. The molecule may comprise, for example, an organic compound, an inorganic compound, a polymer, a peptide, a polypeptide, a protein, a nucleic acid, a carbohydrate, etc. Methods disclosed herein may also be applicable to complexes of molecules, such as one or more protein-drug complex (including or excluding solvent molecules).

The method 1100 may comprise performing an incremental expansion of the energy of the molecule, according to operation 1104. The incremental expansion may be performed according to Equation (1):

$$E_C = \Sigma_i \in_i + \Sigma_{i>j} \in_{ij} + \Sigma_{i>j>k} \in_{ijk} \qquad (1)$$

Here, the correlation energy $E_C$ (the difference between the total molecular energy and the mean-field Hartree-Fock energy) is expressed as an n-body Bethe-Goldstone expansion. The individual n-body correlation energy contributions are defined by Equation (2):

$$\in_i = E_C(i)$$

$$\in_{ij} = E_C(ij) - \in_i - \in_j$$

$$\in_{ijk} = E_C(ijk) - \in_{ij} - \in_{ik} - \in_{jk} - \in_i - \in_j - \in_k \quad (2)$$

Here, $E_C(i)$ are the individual 1-body correlation energies, $E_C(ij)$ are the individual 2-body correlation energies, and $E_C(ijk)$ are the individual 3-body correlation energies. The indices i,j, and k may correspond to any number of molecular orbitals, atoms, molecular fragments, or whole molecules. The indices i,j, and k may correspond to any possible combination of molecular orbitals, atoms, molecular fragments, and whole molecules. Thus, the incremental expansion may be expressed in terms of any possible combination of molecular orbitals, atoms, molecular fragments, and whole molecules.

FIG. 12 depicts molecular orbitals, atoms, molecular fragments, and molecules used as bases for the method of increments. When the incremental expansion is expressed in terms of any possible combination of atoms, fragments, and molecules, the resulting framework may become the framework of an FMO method. When the incremental expansion is expressed in terms of molecular orbitals, the resulting framework may become the framework of an incremental full configuration interaction (iFCI) method, such as that described by Zimmerman et al., "Strong Correlation in Incremental Full Configuration Interaction," *Journal of Chemical Physics,* 2017, 146, 224104, which is hereby incorporated by reference in its entirety.

Returning to the description of FIG. 11, the method 1100 may further comprise solving the Schrödinger equation (e.g., by using a quantum chemistry simulator to solve a quantum chemistry problem according to method 200) for each increment described with reference to operation 1104, according to operation 1106. In some cases, the solution of the Schrödinger equation may be achieved using a phase estimation procedure. For example, a phase estimation algorithm is described by Aspuru-Guzik et al., "Simulated Quantum Computation of Molecular Energies," *Science,* 2005, 309, 1704, which is hereby incorporated by reference in its entirety. In some cases, the solution of the Schrödinger equation may be achieved using an adiabatic quantum simulation. In some cases, the solution of the Schrödinger equation may be achieved by solving a unitary coupled-cluster (UCC) problem within a variational quantum eigensolver (VQE). For example, a VQE is described by McClean et al., "The theory of variational hybrid quantum-classical algorithms," *New Journal of Physics,* 2016, 18, 023023, which is hereby incorporated by reference in its entirety. In some cases, the UCC ansatz may comprise all possible excitations for an increment. In such cases, the UCC ansatz may be equivalent to an exact solution of the Schrödinger equation or to the full configuration interaction (FCI) for each increment. In some cases, truncations of the UCC ansatz to lower order excitations may be used to approximate the exact results (to any possible approximation) for each increment. The solution of the Schrödinger equation may be repeated for one or more increments. For instance, the solution of the Schrödinger equation may be repeated for any possible subset of all increments or may be repeated for all increments. In some cases, the solution of the Schrödinger equation for each increment may be parallelized. For instance, the solution of the Schrödinger equation for each increment may be parallelized using high-performing computing architectures.

The method 1100 may further comprise calculating the quantum mechanical molecular electronic energy, according to operation 1108. The quantum mechanical molecular electronic energy may be calculating by summing each of the incremental contributions according to Equation (1) to yield the quantum mechanical molecular correlation energy and thus the total quantum mechanical energy of the system under study.

Returning to the description of FIG. 1, in some cases, the same fragmentation scheme may be used for all conformers in the ensemble. Such a fragmentation scheme may be appropriate, for example, when the capability of the hardware is limited, and the fragment size has to be very small. This fragmentation scheme may relate to the error cancellation described in the Examples herein. In some cases, a different fragmentation scheme may be used for one or more conformers in the ensemble.

(b) Calculation of Quantum Mechanical Energies and/or Electronic Structures for Each PD Fragment The method 100 may comprise determining, using the hybrid computing unit, quantum mechanical energies and/or electronic structures of each of at least a subset of the plurality of molecular fragments. For example, the method 100 may comprise calculating quantum mechanical energies and/or electronic structures of one or more subsystems according to operations 110, 112, and 114).

According to operation 110, the next fragment or subsystem in the list may be selected. Then, the operations 112 and 114 may be considered for each PD fragment. For example, according to operation 112, the quantum mechanical energy and/or electronic structure of the subsystem may be calculated (e.g., by using a quantum chemistry simulator to solve a quantum chemistry problem according to method 200). According to operation 114, the resulting quantum mechanical energy and/or electronic structure of the subsystem may be stored.

(i) PD Molecular Hamiltonian Construction

In some cases, using the hybrid computing unit to determine quantum mechanical energies and/or electronic structures of the each of the molecular fragments may comprise determining quantum mechanical energies and/or electronic structures of the molecular fragments (e.g., by constructing a molecular Hamiltonian or an electronic Hamiltonian), transforming the quantum mechanical energies and/or electronic structures into equivalent qubit energies and/or electronic structures (e.g., by transforming a fermionic operator of a Hamiltonian to a qubit operator), and determining, using the quantum circuit, the quantum mechanical energy and/or electronic structure of the molecular fragment.

FIG. 2 illustrates a flowchart for an example of a method 200 for providing an indication of the quantum mechanical energy and/or electronic structure of a subsystem, which is defined by problem decomposition techniques, on quantum computing hardware.

The method 200 may comprise obtaining an indication of a subsystem according to operation 202. An approach to solving quantum chemistry problems using classical computing may be to use the Born-Oppenheimer approximation, in which the electron wave function and the nuclear wave function are decoupled and the electronic Hamiltonian is solved. However, the methods disclosed herein may or may not use the Born-Oppenheimer approximation. Such an option to use or not use the Born-Oppenheimer approximation may be selected according to operation 204, for example, by input from a user of the system.

If the Born-Oppenheimer approximation is selected by the user, then the electronic Hamiltonian for the fragment may be constructed according to operation 206. If the Born-Oppenheimer approximation is not selected by the user, then the molecular Hamiltonian for the fragment may be constructed according to operation 208.

The qubit Hamiltonian may be constructed for each fragment using either (a) the first quantization formalism according to operation 212, in which the space in the Hamiltonian is discretized with a grid of qubits, or (b) the second quantization formalism according to operation 214, in which the fermionic operator is transformed to the qubit operator. Such an option to use either the first quantization formalism or the second quantization formalism to generate the qubit Hamiltonian may be selected according to operation 210, for example, by input from a user of the system.

For example, in the case of second quantization formalism with the Born-Oppenheimer approximation, according to operation 206, the electronic Hamiltonian $H^{el}$ may be written as:

$$H^{el} = \sum_{pq} h_{pq} \hat{a}_p^\dagger \hat{a}_a + \frac{1}{2} \sum_{pqrs} V_{pqrs} \hat{a}_p^\dagger \hat{a}_q^\dagger \hat{a}_r \hat{a}_s \qquad (3)$$

where $h_{pq}$ and $V_{pqrs}$ are integrals which can be efficiently precomputed on a classical computer and ai and a are creation and annihilation operators on the basis of spin orbitals. The two-operator terms in the first summation in Equation (3) may correspond to single-electron terms, and the four-operator terms in the second summation in Equation (3) may correspond to electron-electron interaction terms.

The exact form of the molecular Hamiltonian may vary depending on the PD technique as well as the framework being used, such as Full configuration interaction (Full CI) or Coupled-Cluster theory (CC).

(ii) PD Qubit Hamiltonian Construction

According to operation 212, when the first quantization formalism is selected, the qubit Hamiltonian may be obtained by discretizing the 3-dimensional real space into a 3-dimensional grid of qubits. Each grid point may then be represented by a qubit variable.

According to operation 214, when the second quantization formalism is selected, the molecular Hamiltonian (which may be based on spin operators) may be transformed to a qubit Hamiltonian. The qubit Hamiltonian may be based on Pauli operators such as $\{\sigma^x, \sigma^y, \sigma^z\}$ on qubits.

The spin-to-qubit Hamiltonian transformation may be accomplished in a variety of ways, including but not limited to the Jordan-Wigner transformation or the Bravyi-Kitaev transformation.

For example, the Jordan-Wigner transformation provides the following qubit Hamiltonian:

$$H^{el} = \Sigma_{pqrs} \Sigma_{abcd} g_{pqrs}{}^{abcd} \otimes_{p>i>q} \sigma_i^z \otimes_{r>j>s} \sigma_j^z \\ (\sigma_p{}^a \sigma_q{}^b \sigma_r{}^c \sigma_s{}^d) \qquad (4)$$

Here, $\otimes$ indicates an outer product and $g_{pqrs}{}^{abcd}$ is the constant originated from $h_{pq}$ and $V_{pqrs}$ in Equation (3). The set of indices $\{p, q, r, s\}$ may be summed over the spin orbitals. The set of indices $\{a, b, c, d\}$ may be either x or y.

According to operation 216, the time in the Hamiltonian may be discretized, in preparation for performing the simulation of the Hamiltonian.

(iii) Circuit Preparation

According to operation 218, the qubit Hamiltonian may be simulated. The qubit Hamiltonian may be simulated by performing any at least 1, 2, 3, or 4, or at most 4, 3, 2, or 1 of operations 310, 312, 314, and 318 disclosed herein with respect to FIG. 3.

A bottleneck in the process of accurately differentiating the molecular conformations may be performing the total quantum mechanical energy and/or electronic structure calculation. To help ease this bottleneck, PD techniques may be used to break up a problem into smaller, more manageable pieces. In some cases, the total quantum mechanical energy and/or electronic structure calculation for each of a subset of sub-problems can be performed using a quantum computer. In some cases, the quantum computation process for each of a subset of sub-problems can be simulated on a classical computer. The process of calculating the total quantum mechanical energy and/or electronic structure using a quantum computer may comprise running a quantum algorithm to calculate the lowest eigenvalue of a Hamiltonian describing the subproblem.

Figure 3:
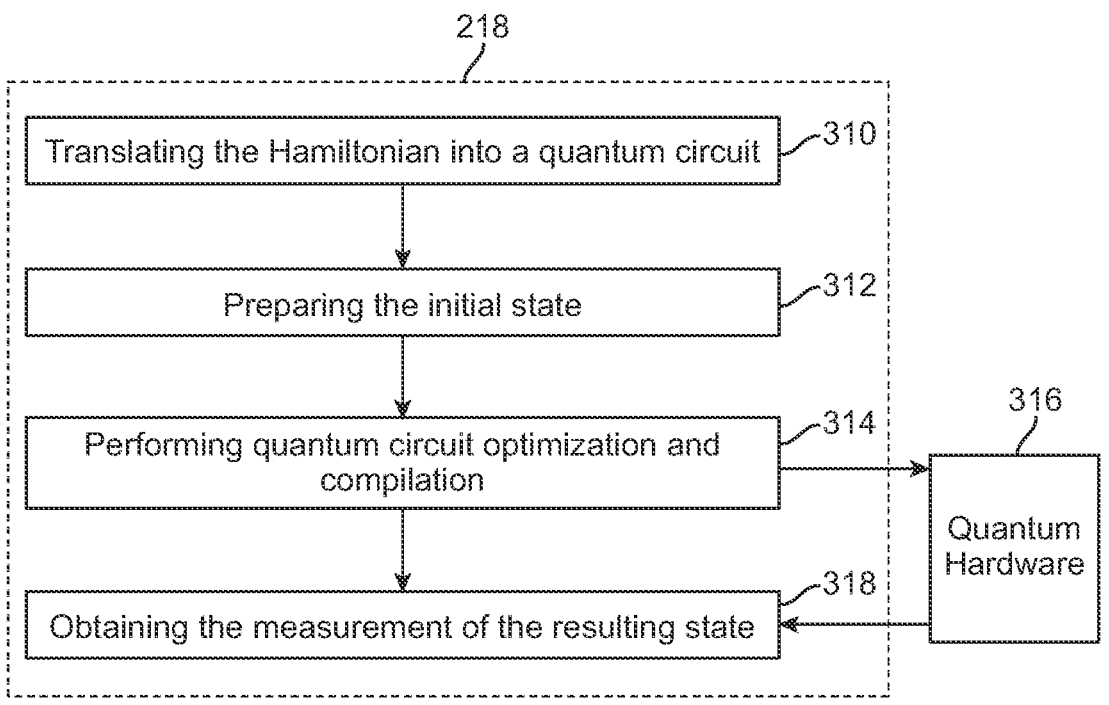
FIG. 3 illustrates a flowchart for an example of a method for providing an indication of the expectation value of the Hamiltonian, on quantum computing hardware, in accordance with some embodiments disclosed herein.

FIG. 3 illustrates a flowchart for an example of a method 218 for providing an indication of the expectation value of the Hamiltonian, on quantum computing hardware. The method 218 may comprise operation 218 of method 200.

The method 218 may comprise translating the Hamiltonian into a quantum circuit that matches to the characteristics of the computing system (e.g., quantum computing system or hardware, or quantum-classical system or hardware) being used (e.g., the connectivity of qubits and which gates are possible to apply) according to operation 310. Techniques for calculating the lowest energy eigenvalue of a Hamiltonian may include the phase estimation algorithm and the variational quantum eigensolver (VQE). For example, the phase estimation algorithm is described by Aspuru-Guzik et al., "Simulated Quantum Computation of Molecular Energies," *Science*, 2005, 309, 1704, which is hereby incorporated by reference in its entirety. For example, the VQE is described by McClean et al., "The theory of variational hybrid quantum-classical algorithms," *New Journal of Physics*, 2016, 18, 023023, which is hereby incorporated by reference in its entirety. These algorithms may be performed to encode the qubit Hamiltonian of a molecule or sub-molecule into the parameters of a quantum circuit.

(iv) Initial State Preparation for Each PD Fragment

The method 218 may comprise preparing an initial state (or initial guess) for the quantum chemistry simulation on the quantum-classical hardware according to operation 312. A suitable initial state may be the Hartree Fock wavefunction. A suitable initial state may be wavefunctions obtained by post Hartree Fock methods. A suitable initial state may be prepared, for instance, using any of the systems or methods described in Matsuura et al., "VanQver: The Variational and Adiabatically Navigated Quantum Eigensolver," arXiv: 1810.11511, Oct. 31, 2018, which is entirely incorporated herein by reference.

(v) Simulation of PD Hamiltonian on Quantum-Classical Hardware

Given the quantum circuit (from operation 310) and initial state (from operation 312), method 218 may comprise simulating the qubit Hamiltonian. The method 218 may comprise compiling and executing (e.g., optimizing) the initial state and/or the qubit Hamiltonian on the quantum computer according to operation 314. In some cases, the quantum computer comprises a quantum hardware device 316 or a classical simulator of a quantum circuit (e.g., a quantum hardware simulator 316). For example, according to operation 314, the transformed quantum circuit and the initial qubit state may be sent to the quantum hardware device 316 or to the quantum hardware simulator 316 in order to perform the quantum chemistry simulation for each fragment.

The sending of the circuit and initial states (according to operations 310 and 312, respectively) for calculating the total quantum mechanical energy and/or electronic structure of a fragment can be done in sequence as the transformed fragments are ready, or they can all be calculated and then sent to one or more quantum hardware devices or classical simulators in parallel.

In some cases, a quantum computer may comprise one or more adiabatic quantum computers, quantum gate arrays, one-way quantum computers, topological quantum computers, quantum Turing machines, superconductor-based quantum computers, trapped ion quantum computers, trapped atom quantum computers, optical lattices, quantum dot computers, spin-based quantum computers, spatial-based quantum computers, Loss-DiVincenzo quantum computers, nuclear magnetic resonance (NMR) based quantum computers, solution-state NMR quantum computers, solid-state NMR quantum computers, solid-state NMR Kane quantum computers, electrons-on-helium quantum computers, cavity-quantum-electrodynamics based quantum computers, molecular magnet quantum computers, fullerene-based quantum computers, linear optical quantum computers, diamond-based quantum computers, nitrogen vacancy (NV) diamond-based quantum computers, Bose-Einstein condensate-based quantum computers, transistor-based quantum computers, and rare-earth-metal-ion-doped inorganic crystal based quantum computers. A quantum computer may comprise one or more of: quantum annealers, Ising solvers, optical parametric oscillators (OPO), and gate models of quantum computing.

In some cases, a classical simulator of the quantum circuit can be used which can run on a classical computer like a MacBook Pro laptop, a Windows laptop, or a Linux laptop. In some cases, the classical simulator can run on a cloud computing platform having access to multiple computing nodes in a parallel or distributed manner. In some cases, the total quantum mechanical energy and/or electronic structure calculation for a subset of fragments can be performed using the classical simulator and the total quantum mechanical energy and/or electronic structure calculation for the remainder of the fragments can be performed using the quantum hardware.

(vi) Measurement of the Resulting State

The method 218 may comprise measuring the quantum bits to provide a classical indication of the lowest eigenvalue according to operation 318. Depending on the algorithm used, the parameters required to produce the electronic structure configuration that produced that lowest energy eigenvalue may also be provided. The basis of a measurement may be indicated by the Hamiltonian and the quantum algorithm being used. A measurement on the quantum data stored in quantum bits may transform that information into classical bits of information. In order to provide an accurate estimation of the data being measured, at least a portion of operation 218 may be repeated. In this case, the plurality of results obtained from a plurality of repeated executions of operation 218 may be averaged. Depending on the algorithm used, the parameters required to produce the electronic structure configuration that produced that lowest energy eigenvalue may also be provided.

Returning to the discussion of FIG. 2, after operation 218 has been performed one or more times, the method 200 may comprise measuring an indication of the expectation value of the Hamiltonian according to operation 220.

The method 200 may comprise determining whether the Born-Oppenheimer approximation was used (e.g., in operation 204) according to operation 222. If the Born-Oppenheimer approximation was used, the method 200 may comprise calculating the nuclear-nuclear repulsion energy and then adding the calculated nuclear-nuclear repulsion energy to the measured expectation value, according to operation 224. The method 200 may comprise providing an indication of the quantum mechanical energy and/or electronic structure of the subsystem according to operation 226, thereby concluding the quantum chemistry simulation performed by the method 200.

Returning to the discussion of FIG. 1, the method 100 may comprise storing the resulting quantum mechanical energy and/or electronic structure of the subsystem, such as in a list of quantum mechanical subsystem energies and/or electronic structures according to operation 112. The method 100 may comprise determining if all subsystems of the conformer have been processed to calculate their quantum mechanical energies and/or electronic structures according to operation 100; if not, then the next subsystem on the list may be selected (according to operation 110) and operations 112 and 114 may be performed thereon.

(c) Combining Quantum Mechanical Energies and/or Electronic Structures for PD Fragments After one or more molecular fragments of the chemical system have been processed to calculate their quantum mechanical energies and/or electronic structures, the method for using the hybrid computing unit to perform a quantum mechanical energy and/or electronic structure calculation for a chemical system may comprise combining the quantum mechanical energies and/or electronic structures determined for the molecular fragments. For example, the method for efficiently identifying the stable conformations of the chemical system may comprise recombining the energies and/or electronic structures obtained for each fragment to obtain the total quantum mechanical energy and/or electronic structure of the conformer of the whole chemical system (e.g., molecule), according to operation 118. The approach in operation 118 to perform recombination of the energies and/or electronic structures of the fragments to obtain the total quantum mechanical energy and/or electronic structure of the conformer of the chemical system may be dependent on and fully described by the problem decomposition (PD) method used in operation 108. The resulting quantum mechanical energy and/or electronic structure of the conformer may then be stored, such as in a list of quantum mechanical conformer energies and/or electronic structures.

According to operation 120, it is determined if all conformers of interest of the chemical system (e.g., molecule) have been processed to calculate their quantum mechanical energies and/or electronic structures; if not, then the next conformer on the list is selected (according to operation 106) and operations 108, 110, 112, 114, 116, and 118 are performed thereon.

In some cases, operations 108, 110, 112, 114, 116, and 118 are performed until a stopping criterion is satisfied. In one embodiment, the stopping criterion may be the convergence of the electronic structure energy of each fragment. In another embodiment, the stopping criterion may be the convergence of the molecular property of each fragment (the number of electrons of the fragment, reduced density matrices and etc.). While the problem decomposition may not change the properties of the molecule being calculated, for example, the energy, in some cases it may be useful to vary the manner and type of problem decomposition until a stopping criterion is met. For example, the number and/or size of fragments may be iteratively changed. For example, block decimation may be iteratively changed in a density matrix renormalization group approach. For example, fragment size may be varied from larger to smaller fragments to increase speed to convergence in systems with high numbers of fragments. For example, in a symmetric system, a number and/or size of fragments may be changed until a sufficient translational invariance between fragments is found to increase speed to convergence in systems by taking the advantage of the symmetry.

Prediction of the Most Stable Conformer

After conformers of interest within the ensemble of conformers have been processed to calculate their quantum mechanical energies and/or electronic structures, the conformers provided in the ensemble of conformers can be sorted in any order, such as sorted by increasing or decreasing order of stability, according to operation 122, based on the estimation of total quantum mechanical energy and/or electronic structure of each of the conformers provided by the operation 118. According to operation 124, an indication of the sorted list of conformers of the chemical system is provided based on the resulting quantum mechanical energy and/or electronic structure, which provides a prediction of the most stable conformer among the ensemble of conformers of the chemical system.

The PD approach may generally provide accurate results, as indicated by studies such as those described by Fedorov et al., "Exploring chemistry with the fragment molecular orbital method," *Physical Chemistry Chemical Physics*, 2012, 14, 7562; Kobayashi et al., "Divide-and-conquer approaches to quantum chemistry: Theory and implementation," in *Linear-Scaling Techniques in Computational Chemistry and Physics: Methods and Applications*, edited by Zalesny et al. (Springer Netherlands, Dordrecht, 2011), 97-127; and Wouters et al., "A Practical Guide to Density Matrix Embedding Theory in Quantum Chemistry," *Journal of Chemical Theory and Computation*, 2016, 12, 2706, each of which is incorporated herein by reference in its entirety.

In addition, the examples below illustrate a good correlation between the energies obtained by a certain method (for example, by CCSD) with and without PD, even when the fragment size is very small. Therefore, the most stable conformer of a chemical system can either be directly identified based on the energies obtained by PD or by using the methods disclosed above to narrow down the size of the conformer ensemble for more accurate computations.

Ab Initio Molecular Dynamics

The systems and methods of the present disclosure may be used to simulate evolution of molecular structures over time using ab initio molecular dynamics (AIMD) techniques. In such simulations, the quantum-enabled problem decomposition (PD) techniques described herein to calculate the quantum mechanical energy and/or electronic structure of a molecule (for instance, as described herein with respect to FIG. 1, FIG. 2, or FIG. 3). The quantum mechanical energy and/or electronic structure calculation may serve as the basis for a force calculation in the AIMD framework. The force on particles within the molecule (such as one or more atoms within the molecule) may be determined based on the quantum mechanical energy obtained by the quantum-enabled PD techniques described herein. The positions and velocities of the particles may then be updated using AIMD techniques.

Figure 13:
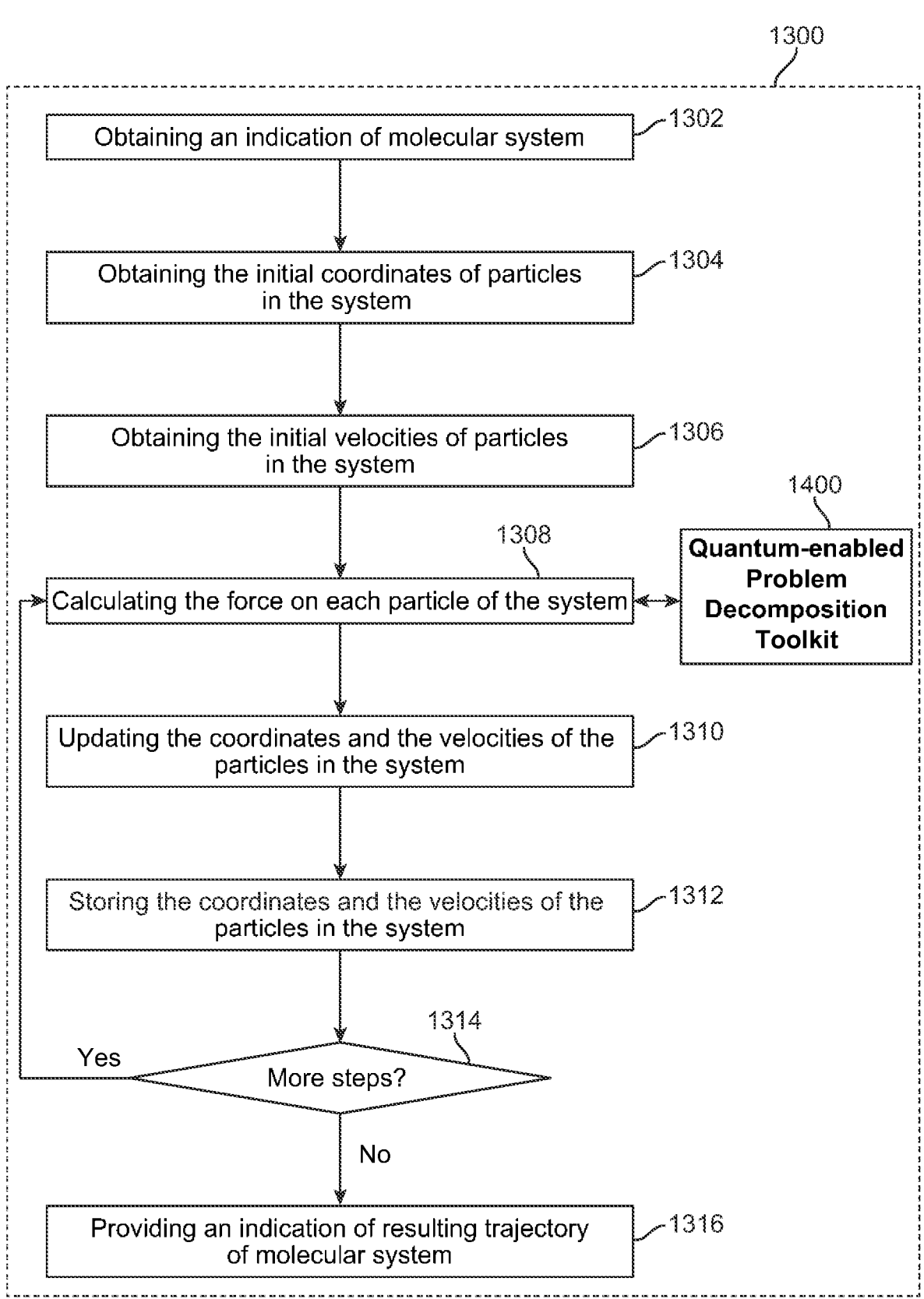
FIG. 13 illustrates a flowchart for an example of a method for performing ab initio molecular dynamics (AIMD) on a molecule using problem decomposition techniques on quantum computing hardware, in accordance with some embodiments disclosed herein.

FIG. 13 illustrates a flowchart for an example of a method 1300 for performing ab initio molecular dynamics (AIMD)

on a molecule using problem decomposition techniques on quantum computing hardware.

The method 1300 may comprise obtaining an indication of an input molecule according to operation 1302. The method 1300 disclosed herein may be applicable to any type of chemical system. The chemical system may comprise, for example, an organic compound, an inorganic compound, a polymer, a peptide, a polypeptide, a protein, a nucleic acid, a carbohydrate, etc. Methods disclosed herein may also be applicable to complexes of molecules, such as one or more protein-drug complex (including or excluding solvent molecules).

The method 1300 may comprise obtaining the initial coordinates of particles in the system according to operation 1304. The initial coordinates of particles in the system may correspond, for instance, to the coordinates of atomic nucleic within a molecule. The initial coordinates of particles in the system may be theoretically-derived or experimentally-derived. For instance, the initial coordinates of particles in the system may be derived from a predicted molecular structure. The initial coordinates of particles in the system may be derived from experimental procedures such as X-ray crystallography, transmission electron microscopy (TEM), scanning electron microscopy (SEM), scanning tunneling electron microscopy (STEM), atomic force microscopy (AFM), solution-state nuclear magnetic resonance (NMR), solid-state NMR, or other experimental procedures. The initial coordinates of particles in the system may be obtained from a database, such as PubChem, Chemical Entities of Biological Interest (ChEBI), DrugBank, small molecule pathway database (SMPDB), ChemDB, Protein Data Bank (PDB), or other databases.

The method 1300 may comprise obtaining the initial velocities of particles in the system according to operation 1306. The initial velocities of the particles may be obtained in a variety of manners. For instance, the initial velocities of the particles may be obtained by randomly choosing a velocity for each particle from a Maxwell-Boltzmann distribution at a temperature. In some cases, such a procedure may result in a net momentum of the system, resulting in an initial linear motion of the system as a whole. In some cases, the initial linear motion may be removed by calculating the net momentum of the system and adjusting the initial velocity of each particle to reduce the net momentum to zero. Similarly, the procedure may result in a net angular momentum of the system, resulting in an initial rotational motion of the system as a whole. In some cases, the initial rotational motion may be removed by calculating the net angular momentum of the system and adjusting the initial angular velocity of each particle to reduce the net angular momentum to zero.

During either operation 1304 or 1306, additional parameters may be set up. For instance, a target number of molecular dynamics time steps, a time increment, a target temperature, and/or a target pressure may be specified.

The method 1300 may comprise calculating the force on each particle of the system according to operation 1308.

Figure 14:
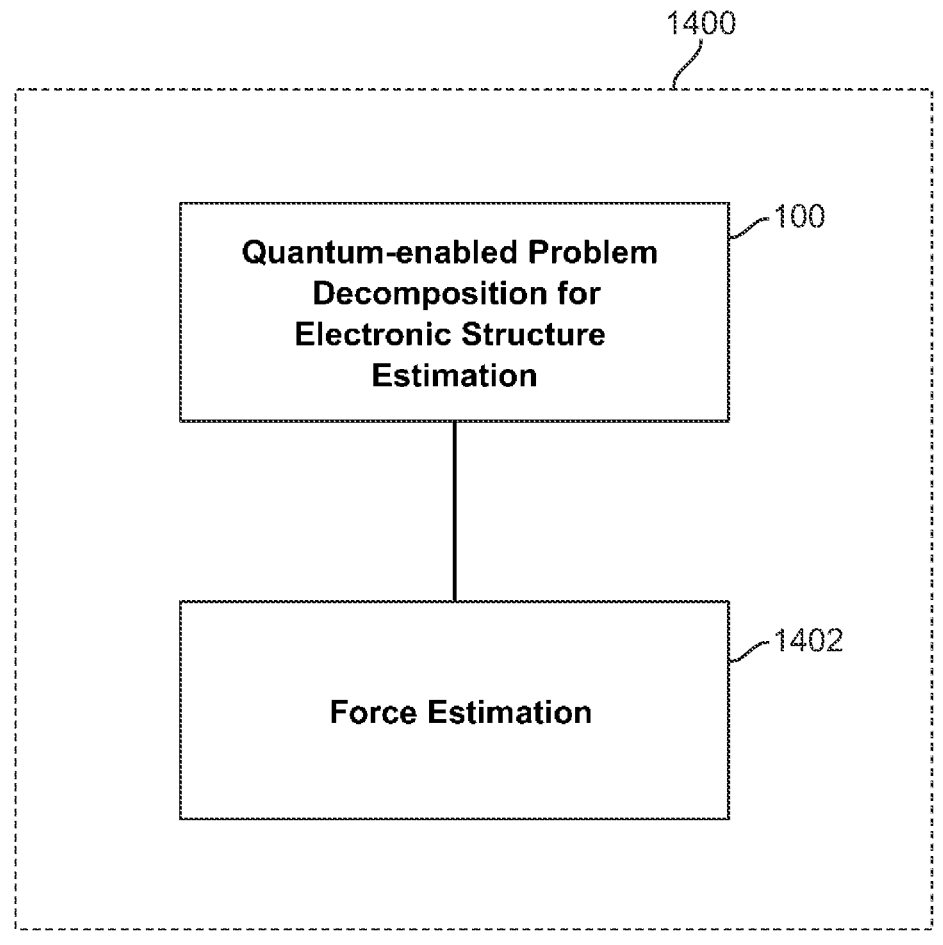
FIG. 14 illustrates a flowchart for an example of a method for calculating the force on each particle of a system in an ab initio molecular dynamics (AIMD) simulation, in accordance with some embodiments disclosed herein.

FIG. 14 illustrates a flowchart for an example of a method 1400 for calculating the force on each particle of a system in an ab initio molecular dynamics (AIMD) simulation. The method may comprise implementing a method for quantum-enabled PD for quantum mechanical energy and/or electronic structure calculation of the system, such as method 100 described herein.

The method may further comprise estimating the force on each particle of the system according to operation 1402. The force on each particle of the system may be calculated from the quantum mechanical energy and/or electronic structure calculation of the system. The force on each particle of the system may be calculated by a variety of procedures. For instance, the force on each particle of the system may be calculated using Jordan's quantum algorithm for numerical gradient estimation as disclosed in Jordan, "Fast Quantum Algorithm for Numerical Gradient Estimation", *Physical Review Letters,* 2015, 95, 050501, which is hereby incorporated by reference in its entirety. Jordan's quantum algorithm for numerical gradient estimation may be performed using quantum hardware (such as a quantum computer described herein) or on a quantum simulator (such as a quantum simulator described herein). The force on each particle of the system may be calculated using numerical gradient estimation techniques on classical hardware (such as a classical computer described herein).

Returning to the discussion of FIG. 13, the method 1300 may further comprise updating the coordinates and/or the velocities of the particles in the system for the next time step according to operation 1310. The coordinates and/or the velocities of the particles in the system may be updated according to a variety of procedures. For instance, the coordinates and/or the velocities of the particles in the system may be updated using a Verlet procedure, in which the coordinates and/or velocities are updated using a series expansion of the coordinates and/or velocities based on the most recent and second-most recent time steps. The coordinates and/or velocities of the particles in the system may be updated using a velocity Verlet procedure, in which the positions are updated based on the most recent velocities, the velocities are partially updated based on the most recent forces, updated forces are calculated using the updated positions, and the velocities are fully updated based on the most recent forces. The coordinates and/or velocities of the particles in the system may be updated by numerical integration of the forces using a variety of integration techniques, such as symplectic integration, Verlet-Stoermer integration, Runge-Kutta integration, Beeman integration, or other integration techniques. During the updating of the coordinates and/or velocities of the particles in the system, a variety of thermostats and/or barostats may be applied to maintain control of the temperature and/or pressure of the system. For instance, a Langevin thermostat and an Anderson barostat may be applied.

The method 1300 may comprise storing the coordinates and/or velocities of the particles in the system, such as in a list of coordinates and/or velocities according to operation 1312. The list of coordinates and/or velocities may comprise a trajectory of the system.

The method 1300 may comprise examining the number of molecular dynamics time steps according to operation 1314. Any one or more of operations 1302, 1304, 1306, 1308, 1310, and 1312 may be repeated until the number of time steps until a stopping criterion is met, for example, reaching a threshold value, a predetermined number of steps, etc. At such a point, the method 1300 may be halted.

The method 1300 may comprise providing an indication of the resulting trajectory of the system.

Distributed Computing

In some cases, the quantum mechanical energies and/or electronic structures of each of the subset of the plurality of molecular fragments may be determined or calculated using one or more distributed computing systems, such as one or more clusters or cloud-based computing systems. The distributed computing systems may comprise a plurality of non-classical computers (such as any non-classical computers described herein), a plurality of classical computers, or both. For instance, the distributed computing systems may comprise a plurality of non-classical computers. Each non-classical computer of the plurality of non-classical computers may be assigned (for instance, via a scheduling routine) to determine or calculate quantum mechanical energies and/or electronic structures of one or more molecular fragments of the plurality of molecular fragments. Each non-classical computer may be configured to determine or calculate quantum mechanical energies and/or electronic structures of the one or more molecular fragments assigned to the non-classical computer in parallel with the determination or calculation of quantum mechanical energies and/or electronic structures of other molecular fragments assigned to other non-classical computers of the plurality of non-classical computers. In this manner, the determination of the quantum mechanical molecular electronic energy and/or the molecular electronic structure may be greatly sped up.

The distributed computing system may comprise at least about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500, 000, 600,000, 700,000, 800,000, 900,000, 1,000,000, or more non-classical computers. The distributed computing system may comprise at most about 1,000,000, 900,000, 800,000, 700,000, 600,000, 500,000, 400,000, 300,000, 200, 000, 100,000, 90,000, 80,000, 70,000, 60,000, 50,000, 40,000, 30,000, 20,000, 10,000, 9,000, 8,000, 7,000, 6,000, 5,000, 4,000, 3,000, 2,000, 1,000, 900, 800, 700, 600, 500, 400, 300, 200, 100, 90, 80, 70, 60, 50, 40, 30, 20, 10, 9, 8, 7, 6, 5, 4, 3, 2, or 1 non-classical computers. The distributed computing system may comprise a number of non-classical computers that is within a range defined by any two of the preceding values.

Each non-classical computer of the plurality of non-classical computers may be configured to determine or calculate quantum mechanical energies and/or electronic structures of at least about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000, 000, 70,000,000, 80,000,000, 90,000,000, 100,000,000, 200, 000,000, 300,000,000, 400,000,000, 500,000,000, 600,000, 000, 700,000,000, 800,000,000, 900,000,000, 1,000,000, 000 or more fragments. Each non-classical computer may be configured to determine or calculate quantum mechanical energies and/or electronic structures of at most about 1,000, 000,000, 900,000,000, 80,000,000, 7000,000,000, 600,000, 000, 500,000,000, 400,000,000, 300,000,000, 200,000,000, 100,000,000, 90,000,000, 80,000,000, 70,000,000, 60,000, 000, 50,000,000, 40,000,000, 30,000,000, 20,000,000, 10,000,000, 9,000,000, 8,000,000, 7,000,000, 6,000,000, 5,000,000, 4,000,000, 3,000,000, 2,000,000, 1,000,000, 900, 000, 800,000, 700,000, 600,000, 500,000, 400,000, 300,000, 200,000, 100,000, 90,000, 80,000, 70,000, 60,000, 50,000, 40,000, 30,000, 20,000, 10,000, 9,000, 8,000, 7,000, 6,000, 5,000, 4,000, 3,000, 2,000, 1,000, 900, 800, 700, 600, 500, 400, 300, 200, 100, 90, 80, 70, 60, 50, 40, 30, 20, 10, 9, 8, 7, 6, 5, 4, 3, 2, or 1 fragments. Each non-classical computer may be configured to determine or calculate quantum mechanical energies and/or electronic structures of a number of fragments that is within a range defined by any two of the preceding values.

Figure 16:
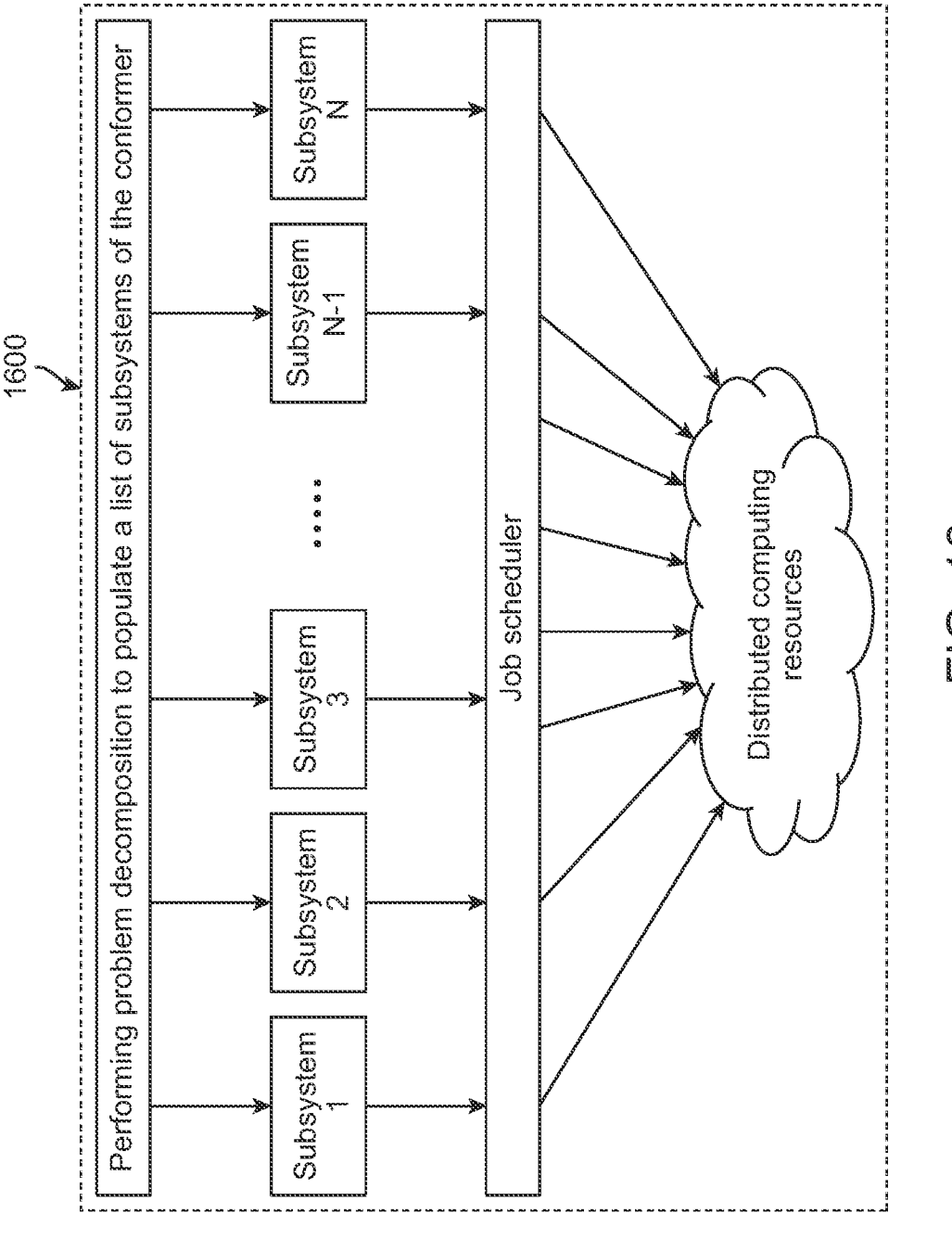
FIG. 16 illustrates a flowchart for an example of a method for performing a quantum mechanical energy or electronic structure calculation for a chemical system using a distributed computing system.

FIG. 16 illustrates a flowchart for an example of a method 1600 for performing a quantum mechanical energy or electronic structure calculation for a chemical system using a distributed computing system.

The method 1600 may comprise one or more operations described herein with respect to method 100 of FIG. 1. For instance, the method 1600 may comprise obtaining an indication of a molecule (operation 102 as described herein with respect to method 100 of FIG. 1, not shown in FIG. 16). The method 1600 may comprise generating or obtaining the list of conformers for the molecule (operation 104 as described herein with respect to method 100 of FIG. 1, not shown in FIG. 16). The method 1600 may comprise selecting the next conformer in the list (operation 106 as described herein with respect to method 100 of FIG. 1, not shown in FIG. 16). The method 1600 may comprise performing problem decomposition to populate a list of subsystems of the conformer (operation 108 described herein with respect to method 100 of FIG. 1).

As shown in FIG. 16, the method 1600 may comprise assigning each subsystem of the conformer to a job scheduler. Each subsystem of the conformer may comprise any molecular fragment described herein. The job scheduler may then assign each subsystem of the conformer to a distributed computing system described herein.

The method 1600 may comprise calculating the energy and/or electronic structure of each subsystem using the distributed computing system (operation 112 as described herein with respect to method 100 of FIG. 1, not shown in FIG. 16). The method 1600 may comprise storing the resulting energy and/or electronic structure of each subsystem (operation 114 as described herein with respect to method 100 of FIG. 1, not shown in FIG. 16). The method 1600 may comprise determining whether all subsystems of the conformer have been evaluated (operation 116 as described herein with respect to method 100 of FIG. 1, not shown in FIG. 16). The method 1600 may comprise combining all subsystem energies and/or electronic structures into the energy and/or electronic structure of the conformer (operation 118 as described herein with respect to method 100 of FIG. 1, not shown in FIG. 16). The method 1600 may comprise determining whether all conformers of the molecule have been evaluated (operation 120 as described herein with respect to method 100 of FIG. 1, not shown in FIG. 16). The method 1600 may comprise sorting conformations based on the resulting energy and/or electronic structure of each conformer (operation 122 as described herein with respect to method 100 of FIG. 1, not shown in FIG. 16). The method 1600 may comprise providing an indication of the sorted list of conformers of the molecule based on the resulting energy and/or electronic structure (operation 124 as described herein with respect to method 100 of FIG. 1, not shown in FIG. 16).

In some cases, the one or more distributed computing systems may be utilized to perform one or more operations of the methods described herein. For instance, the distributed computing systems may be utilized to perform one or more of operations 102, 104, 106, 108, 110, 112, 114, 116, 118, 120, 122, and 124 of method 100 described herein with respect to FIG. 1, one or more of operations 202, 204, 206, 208, 210, 212, 214, 216, 218, 220, 222, 224, or 226 of method 200 described herein with respect to FIG. 2, one or more of operations 310, 312, 314, or 318 of method 300 described herein with respect to FIG. 3, one or more of operations 1102, 1104, 1106, or 1108 of method 1100 described herein with respect to FIG. 11, one or more of operations 1302, 1304, 1306, 1308, 1310, 1312, 1314, or 1316 of method 1300 described herein with respect to FIG. 13, or operation 1402 of method 1400 described herein with respect to FIG. 14. The distributed computing systems may comprise a plurality of classical computers (such as any classical computers described herein). Each classical computer of the plurality of classical computers may be assigned (for instance, via a scheduling routine) to perform any one or more of the operations described herein with reference to the distributed computing systems for one or more molecular fragments of the plurality of molecular fragments. Each classical computer may be configured to perform any one or more of the operations for the one or more molecular fragments assigned to the classical computer in parallel with the performance of the one or more operations for other molecular fragments assigned to other classical computers of the plurality of classical computers. In this manner, execution of the operations may be greatly sped up.

The distributed computing system may comprise at least about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500, 000, 600,000, 700,000, 800,000, 900,000, 1,000,000, or more classical computers. The distributed computing system may comprise at most about 1,000,000, 900,000, 800,000, 700,000, 600,000, 500,000, 400,000, 300,000, 200,000, 100, 000, 90,000, 80,000, 70,000, 60,000, 50,000, 40,000, 30,000, 20,000, 10,000, 9,000, 8,000, 7,000, 6,000, 5,000, 4,000, 3,000, 2,000, 1,000, 900, 800, 700, 600, 500, 400, 300, 200, 100, 90, 80, 70, 60, 50, 40, 30, 20, 10, 9, 8, 7, 6, 5, 4, 3, 2, or 1 classical computer(s). The distributed computing system may comprise a number of classical computers that is within a range defined by any two of the preceding values.

Each classical computer of the plurality of classical computers may be configured to perform any one or more of the operations described herein with reference to the distributed computing systems for at least about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900, 000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000, 000, 70,000,000, 80,000,000, 90,000,000, 100,000,000, 200, 000,000, 300,000,000, 400,000,000, 500,000,000, 600,000, 000, 700,000,000, 800,000,000, 900,000,000, 1,000,000, 000 or more fragments. Each classical computer may be configured to perform any one or more of the operations described herein with reference to the distributed computing systems for at most about 1,000,000,000, 900,000,000, 80,000,000, 7000,000,000, 600,000,000, 500,000,000, 400, 000,000, 300,000,000, 200,000,000, 100,000,000, 90,000, 000, 80,000,000, 70,000,000, 60,000,000, 50,000,000, 40,000,000, 30,000,000, 20,000,000, 10,000,000, 9,000, 000, 8,000,000, 7,000,000, 6,000,000, 5,000,000, 4,000,000, 3,000,000, 2,000,000, 1,000,000, 900,000, 800,000, 700, 000, 600,000, 500,000, 400,000, 300,000, 200,000, 100,000, 90,000, 80,000, 70,000, 60,000, 50,000, 40,000, 30,000, 20,000, 10,000, 9,000, 8,000, 7,000, 6,000, 5,000, 4,000, 3,000, 2,000, 1,000, 900, 800, 700, 600, 500, 400, 300, 200, 100, 90, 80, 70, 60, 50, 40, 30, 20, 10, 9, 8, 7, 6, 5, 4, 3, 2, or 1 fragment(s). Each classical computer may be configured to perform any one or more of the operations described herein with reference to the distributed computing systems for a number of fragments that is within a range defined by any two of the preceding values.

In some cases, the distributed computing system may comprise a plurality of non-classical computers (such as any non-classical computers described herein) and a plurality of classical computers (such as any classical computers described herein). In some cases, a problem (such as a quantum chemistry problem or simulation) may be solved using a distributed computing system comprising various types or combinations of systems, such as, for example, one or more classical computers, one or more non-classical computers (such as one or more quantum computers), or a combination of one or more classical computers and one or more non-classical computers. For instance, FIG. 15 illustrates examples of systems or combinations of systems that may be used to solve a problem, such as a quantum chemistry problems or simulation.

Figure 15:
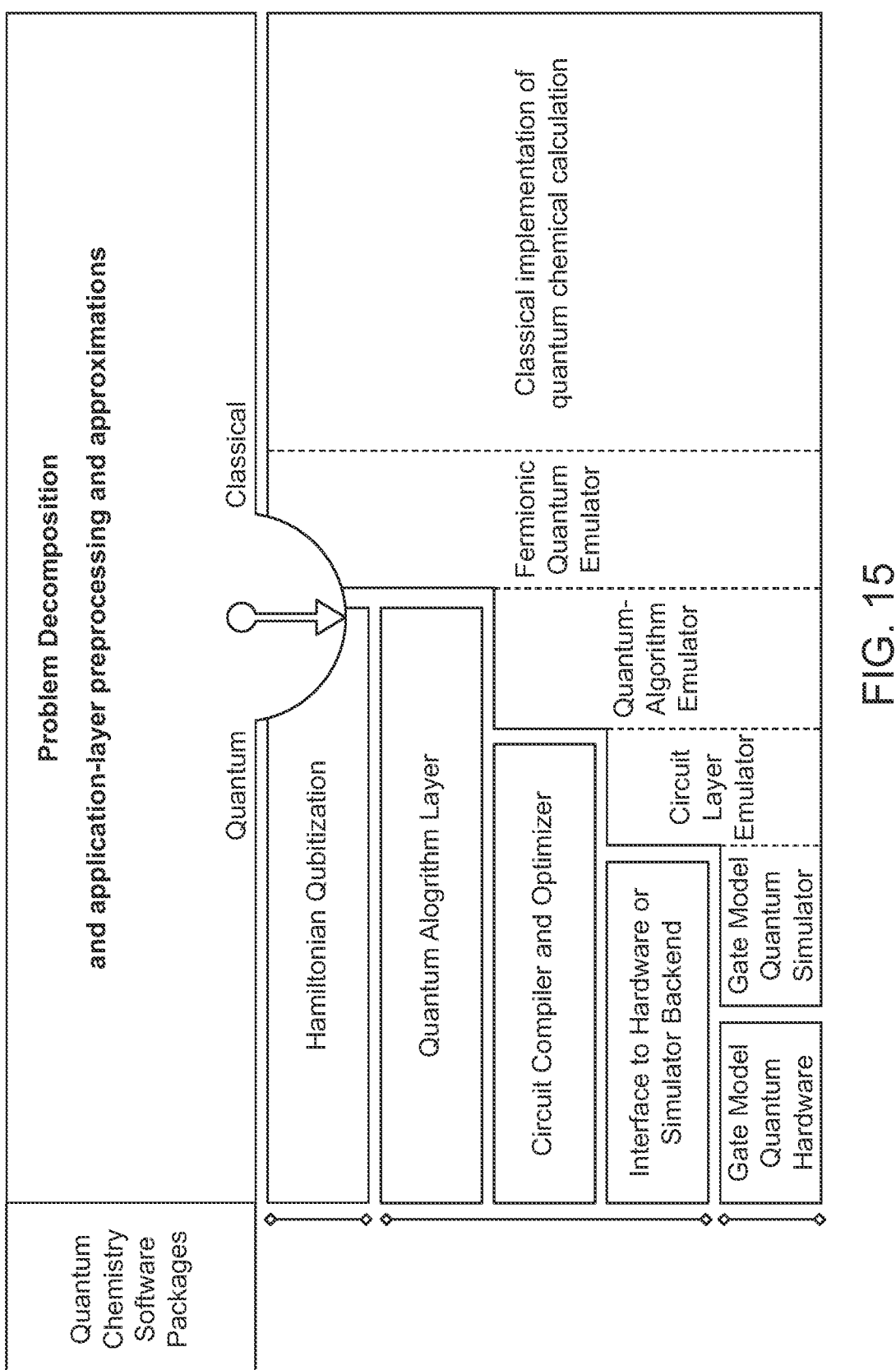
FIG. 15 illustrates examples of systems or combinations of systems that may be used to solve a problem, such as a quantum chemistry problem or simulation.

FIG. 15 illustrates varying types of application layer preprocessing methods and approximations, which may be used to solve a problem. On the right side, an implementation of a calculation may be fully implemented on classical computing systems. On the left side, an implementation of a calculation may be fully implemented on a non-classical computing system (e.g., gate model quantum hardware). In between, varying types of quantum simulators and quantum emulators may be used to implement a calculation.

For instance, methods described herein may be performed on an analogue quantum simulator (e.g., a gate model quantum simulator). An analogue quantum simulator may be a quantum mechanical system consisting of a plurality of manufactured qubits. An analogue quantum simulator may be designed to simulate quantum systems by using physically different but mathematically equivalent or approximately equivalent systems. For example, each qubit may be realized in an ion of strings of trapped atomic ions in linear radiofrequency traps. To each qubit may be coupled a source of bias called a local field bias. The local field biases on the qubits may be programmable and controllable. In some cases, a qubit control system comprising a digital processing unit is connected to the system of qubits and is capable of programming and tuning the local field biases on the qubits.

An analogue quantum simulator may comprise a set of gates and couplings which may be natively implemented on the hardware. An analogue quantum simulator may comprise a set of gates and couplings which may not be natively implemented on the hardware (e.g., non-native gates). An analogue quantum simulator may use secondary qubits (e.g., ancilla qubits) and combinations of native gates to simulate the action of non-native gates. A problem to be solved may utilize one or more of a qubitized Hamiltonian, a quantum algorithm layer, a circuit compiler and/or optimizer, or an interface to hardware or simulator backend.

In some cases, all or a portion of a quantum mechanical energy and/or electronic structure calculation may be performed using a classical simulator (e.g., a classical emulator). A classical simulator may be run on a classical computer like a MacBook Pro laptop, a Windows laptop, or a Linux laptop. In some cases, the classical simulator may be run on a cloud computing platform having access to multiple computing nodes in a parallel or distributed manner, as describe herein with respect to FIG. 18, FIG. 19, FIG. 20, and FIG. 21.

In some cases, a classical simulator of the quantum circuit can be used which can simulate the circuit layer of a calculation on quantum hardware (e.g., classical circuit layer emulator). A problem to be solved may utilize one or more of a qubitized Hamiltonian, a quantum algorithm layer, or a circuit compiler, a circuit optimizer, or both. A classical circuit layer emulator may allow for testing, prototyping, etc. of quantum machine code without use of expensive quantum hardware. A classical circuit layer emulator may emulate the gate operations of a gate model quantum computer or an analogue quantum simulator or both.

In some cases, a classical simulator of a quantum algorithm can be used which can simulate the circuit compiler and circuit layer of a calculation on quantum hardware (e.g., classical algorithm emulator). A problem to be solved may utilize one or more of a qubitized Hamiltonian, or a quantum algorithm layer. A classical algorithm emulator may allow for testing, prototyping, etc. of quantum machine code without use of expensive quantum hardware. A classical algorithm emulator may emulate the gate operations of a gate model quantum computer or an analogue quantum simulator or both. A classical algorithm emulator may emulate circuit compiling and optimizing of a gate model quantum computer or an analogue quantum simulator or both.

In some cases, a quantum mechanical energy and/or electronic structure calculation may be performed using a classical simulator which can simulate a quantum mechanical system without transforming a fermionic Hamiltonian into a qubit Hamiltonian (e.g., fermionic quantum emulator)

Figure 17:
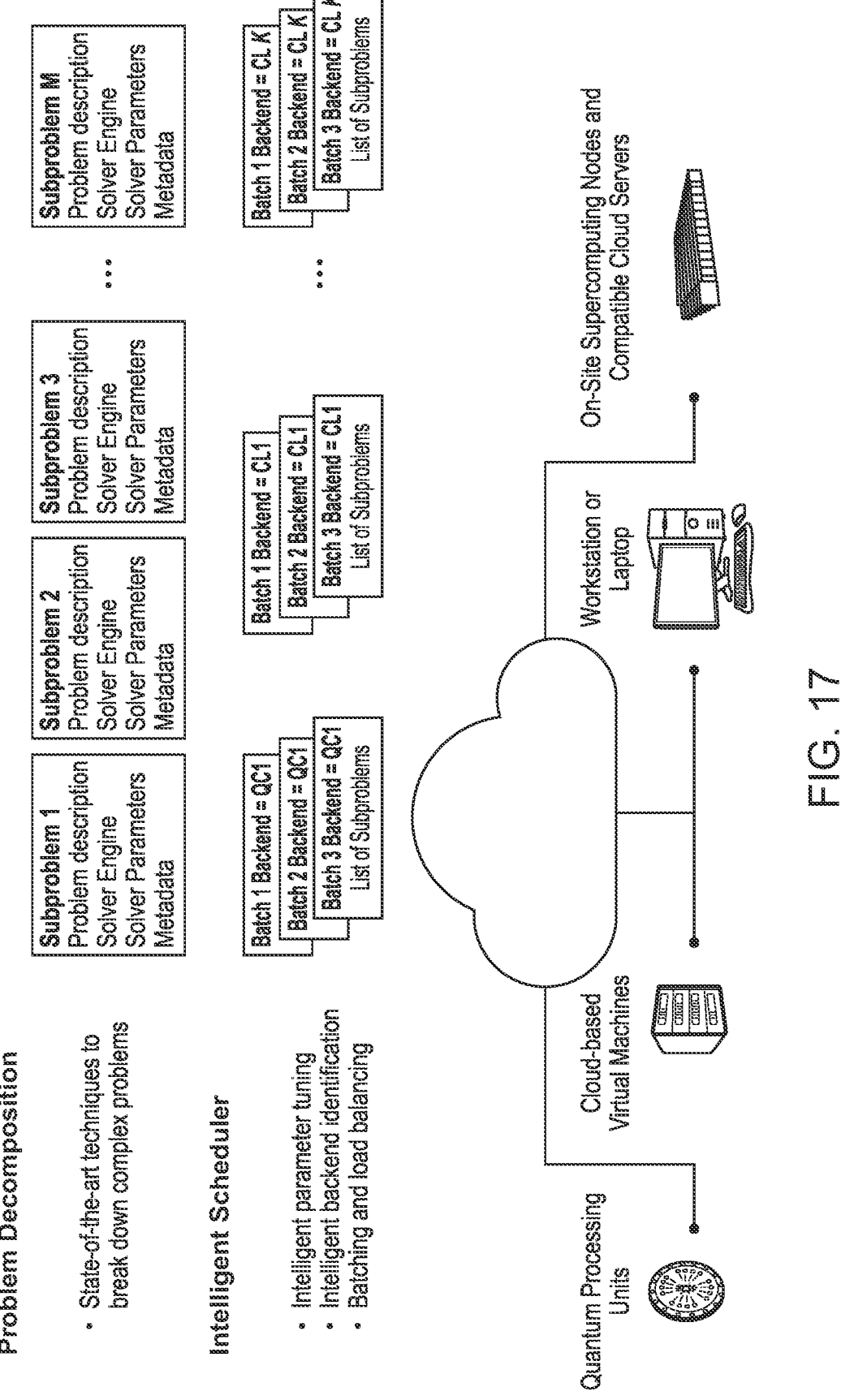
FIG. 17 illustrates an example of an architecture for a distributed computing system comprising a non-classical (e.g., quantum computer) and a plurality of classical computers.

FIG. 17 illustrates an example of an architecture for a distributed computing system comprising a non-classical or quantum computer (QC 1) and a plurality of classical computers (CL 1 through CL K, where K is an integer). A distributed computing system may include at least one classical computer and at least one non-classical computer. In some cases, a distributed computing system may comprise all classical computers. In some cases, a distributed computing system may have all quantum computers. The distributed computing system may include (i) at least or a plurality (e.g., at least 2, 3, 4, 5, 6, 7, 8, 9, 10, or more) of non-classical computers (e.g., a quantum computer), and (ii) at least or a plurality (e.g., at least 2, 3, 4, 5, 6, 7, 8, 9, 10, or more) of classical computers.

A distributed computing system may be managed by a scheduler. The scheduler may tune one or more parameters of at least one of the one or more subproblems. The scheduler may identify computing resources in the various nodes of the distributed computing network, e.g., one or more non-classical computers, one or more classical computers, one or more virtual machines, one or more cloud based machines, one or more work stations, one or more supercomputing nodes, one or more servers, etc. The scheduler may order subproblems, may prioritize subproblems, may distribute problems to the various computing resources, etc.

FIG. 18, FIG. 19, FIG. 20, and FIG. 21 illustrate various examples of organizations of distributed computing system of the present disclosure. In some cases, the distributed computing systems of any of FIG. 18, FIG. 19, FIG. 20, or FIG. 21 may be used to perform one or more operations of the methods described herein. For instance, the distributed computing systems any of FIG. 18, FIG. 19, FIG. 20, or FIG. 21 may be utilized to perform one or more of operations 102, 104, 106, 108, 110, 112, 114, 116, 118, 120, 122, and 124 of method 100 described herein with respect to FIG. 1, one or more of operations 202, 204, 206, 208, 210, 212, 214, 216, 218, 220, 222, 224, or 226 of method 200 described herein with respect to FIG. 2, one or more of operations 310, 312, 314, or 318 of method 300 described herein with respect to FIG. 3, one or more of operations 1102, 1104, 1106, or 1108 of method 1100 described herein with respect to FIG. 11, one or more of operations 1302, 1304, 1306, 1308, 1310, 1312, 1314, or 1316 of method 1300 described herein with respect to FIG. 13, or operation 1402 of method 1400 described herein with respect to FIG. 14.

Figure 18:
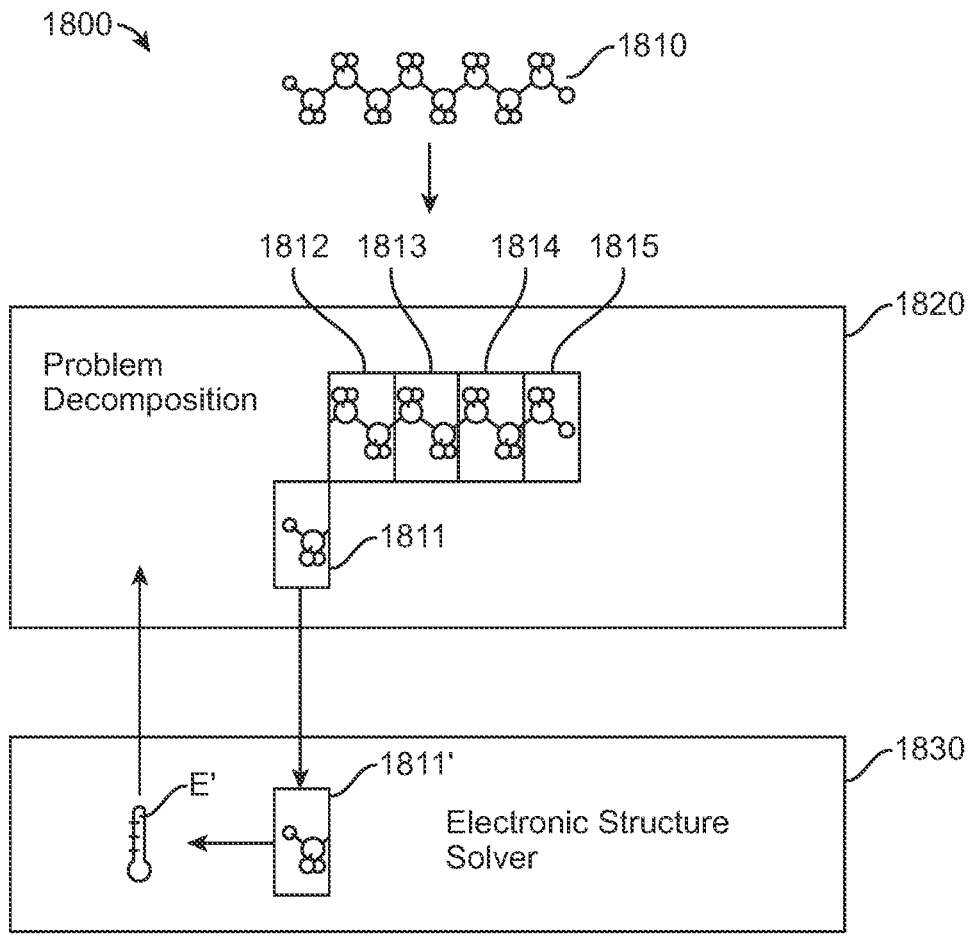
FIG. 18 illustrates a distributed computing system comprising a sequential problem decomposition, in accordance with some embodiments disclosed herein.

FIG. 18 illustrates a distributed computing system comprising a sequential problem decomposition, in accordance with some embodiments. The quantum-enabled problem decomposition (PD) techniques described herein to calculate the quantum mechanical energy and/or electronic structure of a molecule (for instance, as described herein with respect to FIG. 1, FIG. 2, or FIG. 3) may comprise embodiments, variations, or examples of sequential problem decomposition techniques implementable on the distributed computing system 1800 of FIG. 18.

A target 1810 may comprise a chemical system. A chemical system may comprise, for example, a molecule, a portion of a molecule, a fragment, an aggregate, etc. Target 1810 may be decomposed into one or a plurality of fragments. For example, target 1810 may be decomposed into fragments 1811, 1812, 1813, 1814, and 1815. FIG. 18 shows problem decomposer 1820. The problem decomposer may comprise any of the problem decomposition methods and/or techniques disclosed herein. After decomposition, a fragment 1811 may be encoded as fragment 1811' on an electronic structure solver 1830. Electronic structure solver 1830 may comprise a non-classical or quantum computing system, as described herein. Electronic structure solver 1830 may calculate energy E' for fragment 1811'. Electronic structure solver 1830 may pass energy E' to problem decomposer 1820, and fragment 1812 may be passed to electronic structure solver 1830. Each fragment of target 1810 may be sequentially passed to electronic structure solver 1830. All or a portion of the plurality of fragments may be passed to electronic structure solver 1830. The plurality of fragments may be passed to electronic structure solver 1830 in any order.

The problem decomposer 1820 and the electronic structure solver 1830 may comprise portions of a distributed computing system. For example, problem decomposer 1820 may be local to a user (e.g., on the same machine used by the user, in the same physical location on a separate machine, etc.) and electronic structure solver 1830 may be remote to a user. For example, problem decomposer 1820 may comprise a portion of a client-side library. For example, electronic structure solver 1830 may comprise a remote endpoint. For example, problem decomposer 1820 may be remote to a user at a first remote endpoint, and electronic structure solver 1830 may be remote to a user at a second remote endpoint. The first remote endpoint and the second remote endpoint may be the same endpoint. The first remote endpoint and the second remote endpoint may be remote to one another. For example, the first remote endpoint may comprise a remote server and the second remote endpoint may comprise a non-classical computer. A remote endpoint may comprise a classical computing system, a non-classical computing system, or a hybrid computing unit disclosed herein.

While the example illustrated in FIG. 18 shows five fragments and solves, methods of the present disclosure may be used with any number of fragments and solvers. For example, the distributed computing system of FIG. 18 may be configured to perform any one or more of the operations described herein for at least about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000, 000, 70,000,000, 80,000,000, 90,000,000, 100,000,000, 200, 000,000, 300,000,000, 400,000,000, 500,000,000, 600,000, 000, 700,000,000, 800,000,000, 900,000,000, 1,000,000, 000 or more fragments. For example, the distributed computing system of FIG. 18 may be configured to perform any one or more of the operations described herein for at most about 1,000,000,000, 900,000,000, 80,000,000, 7000, 000,000, 600,000,000, 500,000,000, 400,000,000, 300,000, 000, 200,000,000, 100,000,000, 90,000,000, 80,000,000, 70,000,000, 60,000,000, 50,000,000, 40,000,000, 30,000, 000, 20,000,000, 10,000,000, 9,000,000, 8,000,000, 7,000, 000, 6,000,000, 5,000,000, 4,000,000, 3,000,000, 2,000,000, 1,000,000, 900,000, 800,000, 700,000, 600,000, 500,000, 400,000, 300,000, 200,000, 100,000, 90,000, 80,000, 70,000, 60,000, 50,000, 40,000, 30,000, 20,000, 10,000, 9,000, 8,000, 7,000, 6,000, 5,000, 4,000, 3,000, 2,000, 1,000, 900, 800, 700, 600, 500, 400, 300, 200, 100, 90, 80, 70, 60, 50, 40, 30, 20, 10, 9, 8, 7, 6, 5, 4, 3, 2, or 1 fragment(s). For example, the distributed computing system of FIG. 18 may be configured to perform any one or more of the operations described herein for a number of fragments that is within a range defined by any two of the preceding values.

In some cases, method comprising a sequential problem decomposition may comprise generating an instance of an electronic structure solver; generating each of the plurality of fragments; and solving the electronic structure of each fragment with its electronic structure solver sequentially, thereby generating an energy for each fragment. A sequential problem decomposition may be improved by parallelization of the problem.

Parallelization of the problem may be facilitated by problem decomposition followed by distribution of subsystems of the problem over one or more nodes in a high-performance computer, which high performance computer may comprise one or more non-classical computers. FIGS. 18, 19, 20, and 21 show examples of distributed computing systems which may implement methods described herein for performing a quantum mechanical energy or electronic structure calculation for a chemical system using a distributed computing system (for instance, as described herein with respect to FIG. 16). The method 1600 may comprise one or more operations of the quantum-enabled problem decomposition (PD) techniques described herein to calculate the quantum mechanical energy and/or electronic structure of a molecule (for instance, as described herein with respect to FIG. 1, FIG. 2, or FIG. 3). Steps of the methods of FIG. 1, FIG. 2, FIG. 3, FIG. 11, FIG. 13, or FIG. 14 may be performed on a distributed computing system comprising a plurality of non-classical computers (such as any non-classical computers described herein) and a plurality of classical computers (such as any classical computers described herein).

Figure 19:
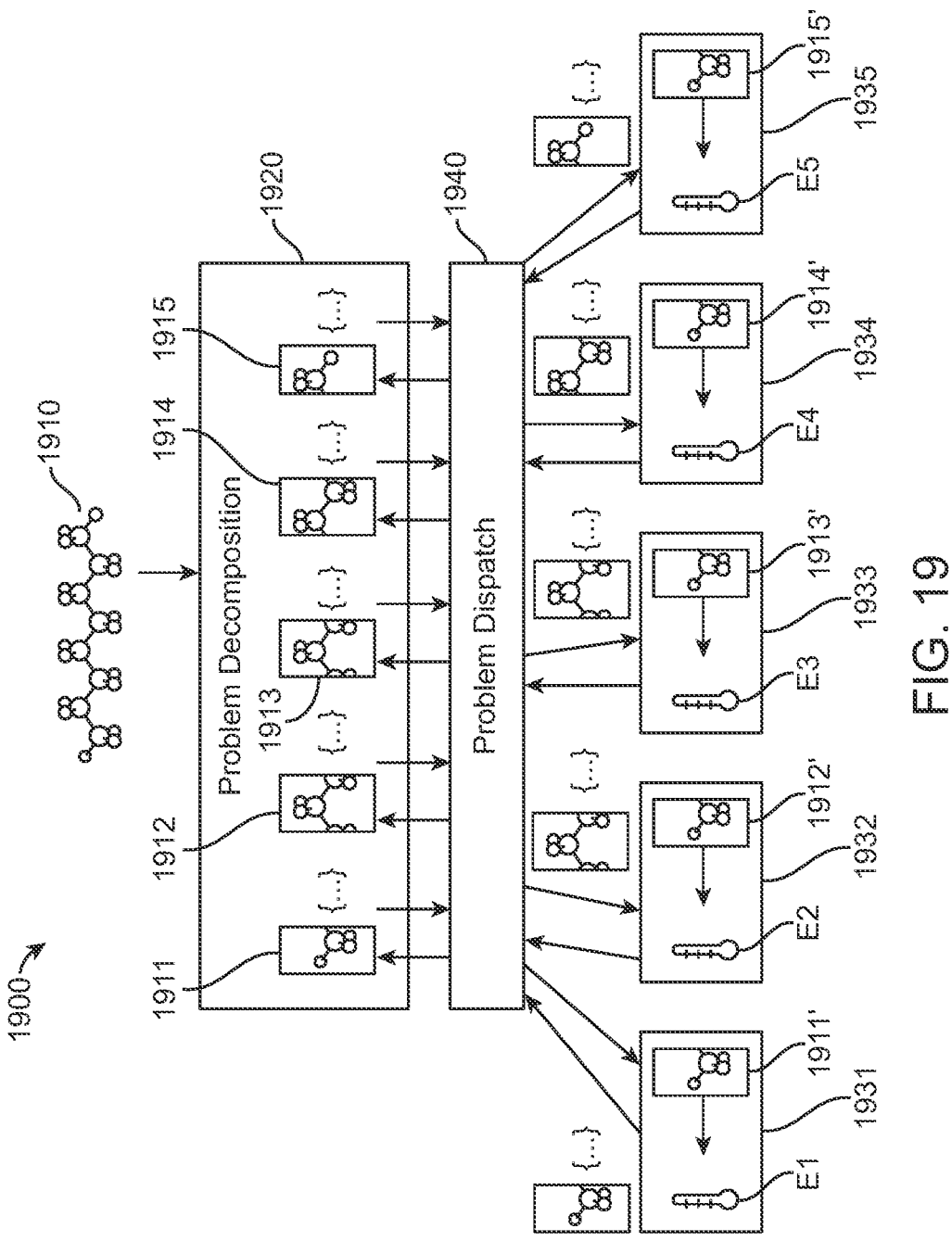
FIG. 19 illustrates a distributed computing system comprising a problem dispatch, in accordance with some embodiments disclosed herein.

FIG. 19 illustrates a distributed computing system 1900 comprising a problem dispatch, in accordance with some embodiments. A problem dispatch may be used to distribute subsystems of the problem over one or more nodes. For example, the problem dispatch may provide a logic that controls the distribution of subsystems to nodes and returns results from the nodes. The problem dispatch may control whether each subsystem of the problem is solved locally (e.g., on the same machine, in the same physical location on a separate machine, etc.), on the cloud, or in a high-performance computing cluster.

The problem decomposition may create subsystems, for example fragments, and a data structure for each fragment. For example, a data structure may contain the type of electronic structure solver and/or the parameters to be passed to the solver. In some cases, the data structure may pass an input from a user. In some cases, the data structure may pass parameters based on the input problem. The problem dispatch may handle the creation and/or implementation of an electronic structure solver with parameters, such as parameters from the dictionary. The problem dispatch may return an output from the solver, such as for example an energy. A simple problem dispatch may create and/or implement each solver serially. In some example, a problem dispatch may use a multiprocessing package to create and/or implement each solver using a parallel scheme, such as for example Python's multiprocessing package.

A target 1910 may comprise a chemical system. A chemical system may comprise, for example, a molecule, a portion of a molecule, a fragment, an aggregate, etc. Target 1910 may be decomposed into one or a plurality of fragments. For example, target 1910 may be decomposed into fragments 1911, 1912, 1913, 1914, and 1915 at a problem decomposer. FIG. 19 shows problem decomposer 1920. The problem decomposer may comprise instructions to perform any of the problem decomposition methods and/or techniques disclosed herein.

After decomposition, the fragments may be distributed to one or more electronic structure solvers 1931, 1932, 1933, 1934, and 1935 by problem dispatch 1940. Problem dispatch 1940 may create and/or implement the electronic structure solver. Problem dispatch 1940 may pass parameters to the solver, such as input parameters from a user. The problem dispatch may return an output from the solver, such as for example an energy.

Fragments 1911, 1912, 1913, 1914, and 1915 may be encoded as fragments 1911', 1912', 1913', 1914', and 1915' on electronic structure solvers 1931, 1932, 1933, 1934, and 1935. Electronic structure solvers 1931, 1932, 1933, 1934, and 1935 may comprise one or more non-classical computing systems, one or more quantum computing systems, or one or more hybrid computing units, as described herein. Electronic structure solvers 1931, 1932, 1933, 1934, and 1935 may calculate energies $E^1$, $E^2$, $E^3$, $E^4$, and $E^5$ for fragments 1911', 1912', 1913', 1914', and 1915', respectively. Electronic structure solver 1931, 1932, 1933, 1934, and 1935 may pass energies $E^1$, $E^2$, $E^3$, $E^4$, and $E^5$ to problem dispatch 1940. The electronic structure solvers may receive and return fragments from the problem dispatch.

All or a portion of the plurality of fragments may be passed to the electronic structure solvers. The plurality of fragments may be passed to the electronic structure solvers in any order, sequentially or in parallel. The problem decomposer 1920, problem dispatch 1930, and electronic structure solvers 1931, 1932, 1933, 1934, and 1935 may comprise portions of a distributed computing system.

The distributed computing system comprising a problem dispatch of FIG. 19 may be implemented in a variety of ways. For example, some code may be run by a "client side" digital computing device, for example the digital computing device of a user, and other code may be run on a portion of a distributed computing system, which distributed computing system may comprise one or more remote endpoints. The distributed computing system may comprise one or more clusters or cloud-based computing systems. The distributed computing systems may comprise a plurality of non-classical computers (such as any non-classical computers described herein), a plurality of classical computers, or both. The distributed computing system may comprise one or more endpoints. The one or more endpoints may comprise representational state transfer (REST) endpoints. The one or more endpoints may execute a response from the client-side library. The REST calls may be executed on the distributed computing system, for example, one or more classical, hybrid, or non-classical computing devices connected via a network such as a cloud network.

While the example illustrated in FIG. 19 shows five fragments and solves, methods of the present disclosure may be used with any number of fragments and solvers. For example, the distributed computing system of FIG. 19 may be configured to perform any one or more of the operations described herein for at least about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000, 000, 70,000,000, 80,000,000, 90,000,000, 100,000,000, 200, 000,000, 300,000,000, 400,000,000, 500,000,000, 600,000, 000, 700,000,000, 800,000,000, 900,000,000, 1,000,000, 000 or more fragments. For example, the distributed computing system of FIG. 19 may be configured to perform any one or more of the operations described herein for at most about 1,000,000,000, 900,000,000, 80,000,000, 7000, 000,000, 600,000,000, 500,000,000, 400,000,000, 300,000, 000, 200,000,000, 100,000,000, 90,000,000, 80,000,000, 70,000,000, 60,000,000, 50,000,000, 40,000,000, 30,000, 000, 20,000,000, 10,000,000, 9,000,000, 8,000,000, 7,000, 000, 6,000,000, 5,000,000, 4,000,000, 3,000,000, 2,000,000, 1,000,000, 900,000, 800,000, 700,000, 600,000, 500,000, 400,000, 300,000, 200,000, 100,000, 90,000, 80,000, 70,000, 60,000, 50,000, 40,000, 30,000, 20,000, 10,000, 9,000, 8,000, 7,000, 6,000, 5,000, 4,000, 3,000, 2,000, 1,000, 900, 800, 700, 600, 500, 400, 300, 200, 100, 90, 80, 70, 60, 50, 40, 30, 20, 10, 9, 8, 7, 6, 5, 4, 3, 2, or 1 fragment(s). For example, the distributed computing system of FIG. 19 may be configured to perform any one or more of the operations described herein for a number of fragments that is within a range defined by any two of the preceding values.

There are many approaches to distributing the problem between the client-side library and the one or more endpoints. The distribution of functionality between the client-side library and the one or more endpoints may be varied based on the problem to be solved and/or the needs of the user.

Figure 20:
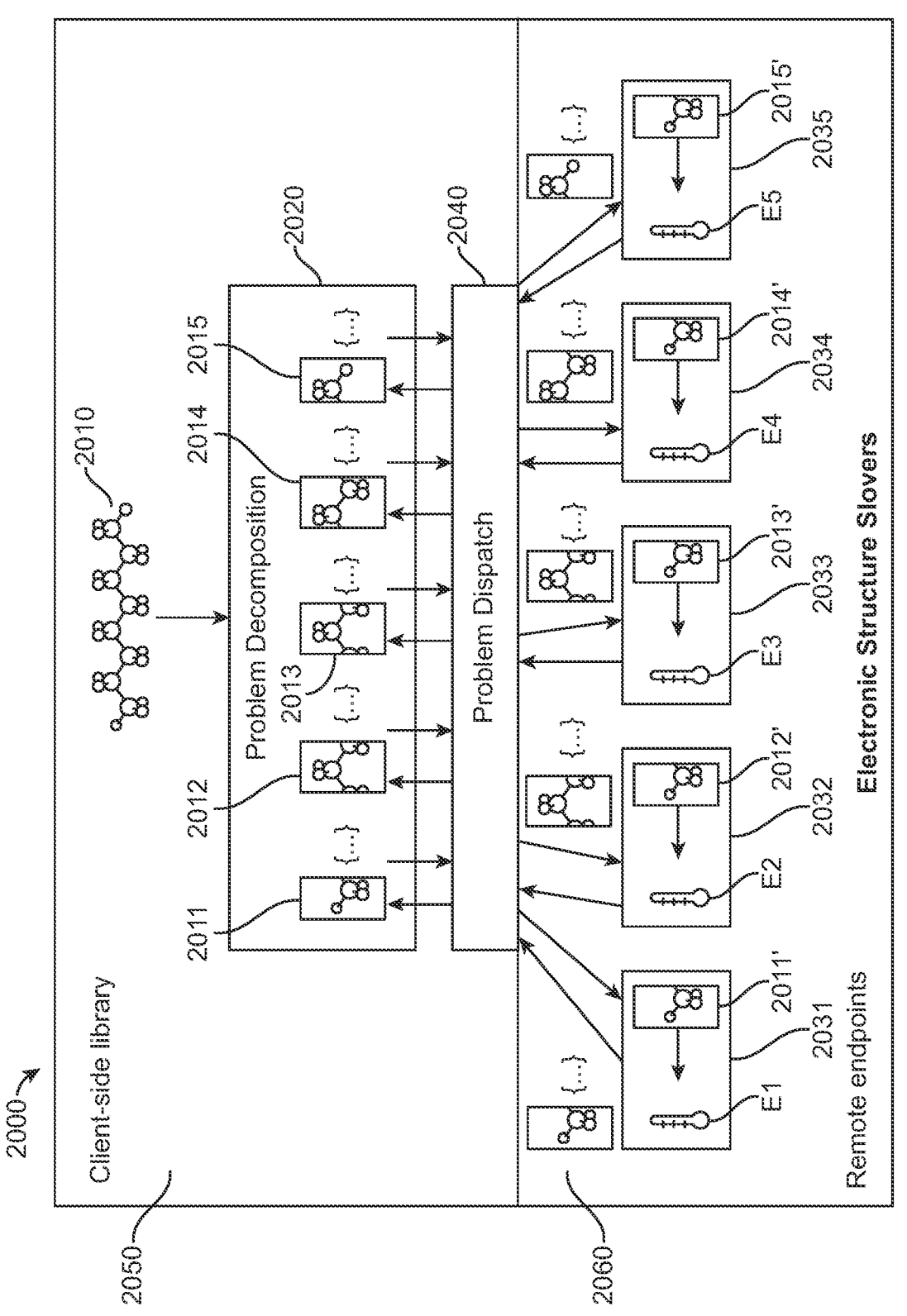
FIG. 20 illustrates an example architecture of a distributed computing system comprising a problem dispatch within a client-side library, in accordance with some embodiments disclosed herein.

In an approach, the problem decomposition and problem dispatch may occur within a client-side library, see for example FIG. 20. The problem decomposition and problem dispatch may occur on the digital computing device of a user. The problem dispatch may distribute the subsystems to electronic structure solvers which may be located at one or more remote endpoints. The remote endpoints may comprise nodes of one or more high performance computing systems, for example, one or more non-classical computing systems, one or more classical computing systems, or a combination thereof.

Figure 21:
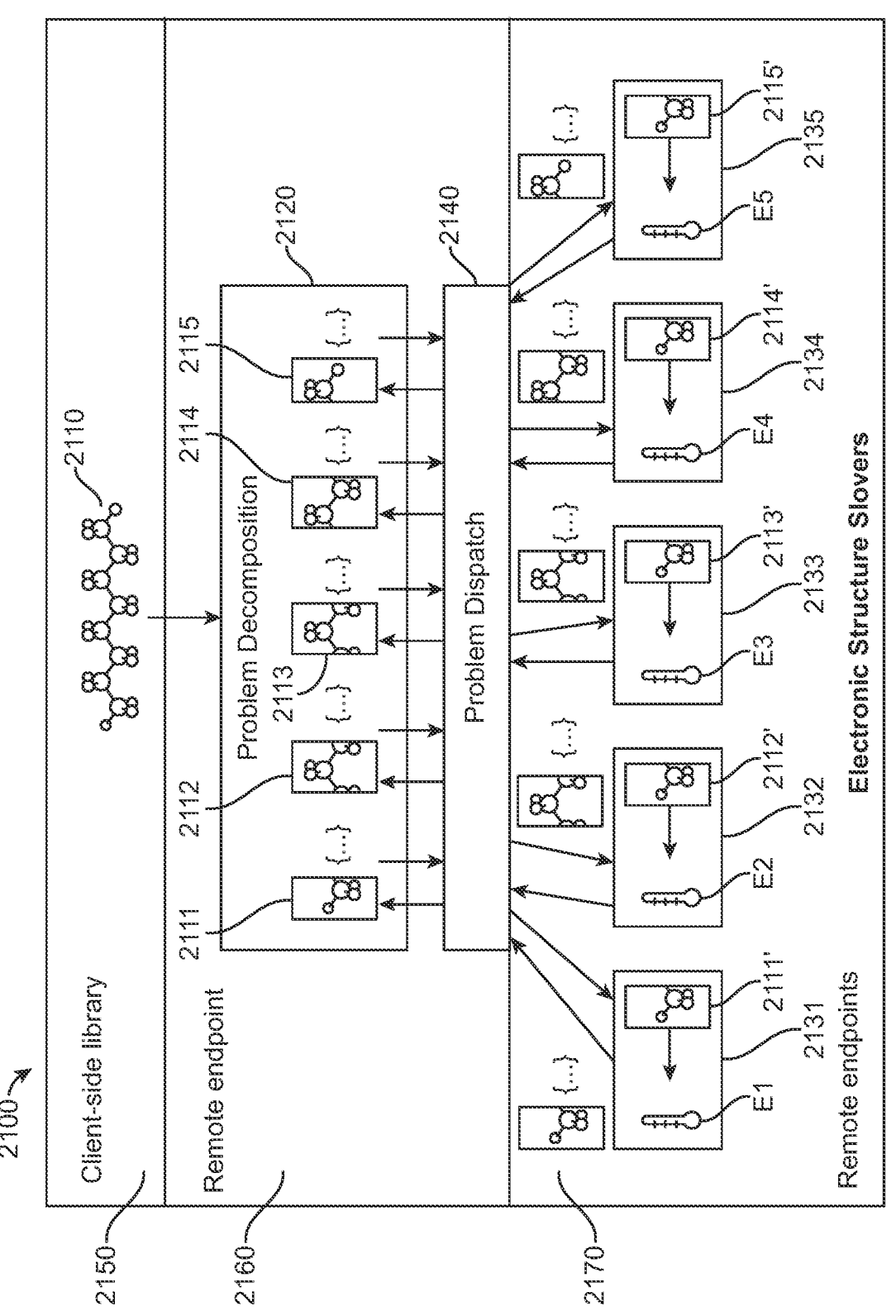
FIG. 21 illustrates an example architecture of a distributed computing system comprising a problem dispatch at a remote endpoint, in accordance with some embodiments disclosed herein.

In another approach, the problem may be transmitted from a client-side library to a remote endpoint, which remote endpoint may decompose the problem and dispatch the problem, see for example FIG. 21. In some cases, the problem may be dispatched from the remote endpoint to one or more second remote endpoints, which second remote endpoints may comprise nodes of one or more high performance computing systems. In some cases, one or more nodes of the one or more second remote endpoints may be local (e.g., on the same machine, in the same physical location on a separate machine, etc.) to the problem dispatch. In some cases, one or more nodes of the one or more second remote endpoints may be remote to the problem dispatch.

In another approach, the problem may be decomposed within the client-side library, transmitted to a remote endpoint comprising the problem dispatch, and transmitted to one or more second remote endpoints comprising the electronic structure solvers.

FIG. 20 illustrates an example architecture 2000 of a distributed computing system comprising a problem dispatch within a client-side library, in accordance with some embodiments. In the illustrated embodiment, the problem decomposition may be executed by client-side code. The problem decomposition may generate the subsystems and/or solver parameters. The client-side system may forward the subsystems and/or solver parameters to the problem dispatch. The problem dispatch may create and make REST calls, map the return values back to the input subsystems, and return the values back to the problem decomposition. The architecture of FIG. 20 may be advantageous if a user does not wish to disclose the problem to be solved, as fragments of the data rather than a more complete implementation of the problem may be transferred to the remote endpoints.

As shown in FIG. 20, a target 2010, problem decomposer 2020, and problem dispatch 2040 may comprise portions of a client-side computing system 2050, e.g., a client-side library. A target 2010 may comprise a chemical system. A chemical system may comprise, for example, a molecule, a portion of a molecule, a fragment, an aggregate, etc. Target 2010 may be decomposed into one or a plurality of fragments. For example, target 2010 may be decomposed into fragments 2011, 2012, 2013, 2014, and 2015 at a problem decomposer. FIG. 20 shows problem decomposer 2020. The problem decomposer may comprise instructions to perform any of the problem decomposition methods and/or techniques disclosed herein.

After decomposition, the fragments may be distributed to one or more electronic structure solvers 2031, 2032, 2033, 2034, and 2035 by problem dispatch 2040. Problem dispatch 2040 may create and/or implement the electronic structure solvers. Problem dispatch 2040 may pass parameters to one or more solvers, such as input parameters from a user. The problem dispatch may return outputs from the solver, such as for example, energies.

Problem dispatch 2040 may serve to communicate with the one or more solvers. In the illustrated embodiment, the one or more solver may comprise portions of one or more remote endpoints 2060. The remote endpoints may be local (e.g., on the same machine, in the same physical location on a separate machine, etc.) to one another or remote to one another. The remote endpoints may comprise remote servers, a cloud network, portions of a distributed computing system, etc. The solver called by the problem dispatch may be specific to the problem type and/or fragment type. The problem dispatch may serve, in part, to distribute computational operations to reduce computation time and/or increase computational accuracy.

Fragments 2011, 2012, 2013, 2014, and 2015 may be encoded as fragments 2011', 2012', 2013', 2014', and 2015' on electronic structure solvers 2031, 2032, 2033, 2034, and 2035. Electronic structure solvers 2031, 2032, 2033, 2034, and 2035 may comprise one or more non-classical computing systems, one or more quantum computing systems, or one or more hybrid computing units, as described herein. Electronic structure solvers 2031, 2032, 2033, 2034, and 2035 may calculate energies $E^1$, $E^2$, $E^3$, $E^4$, and $E^5$ for fragments 2011', 2012', 2013', 2014', and 2015', respectively. Electronic structure solver 2031, 2032, 2033, 2034, and 2035 may pass energies $E^1$, $E^2$, $E^3$, $E^4$, and $E^5$ to problem dispatch 2040. The electronic structure solvers may receive and return fragments from the problem dispatch.

All or a portion of the plurality of fragments may be passed to the electronic structure solvers. The plurality of fragments may be passed to the electronic structure solvers in any order, sequentially or in parallel.

While the example illustrated in FIG. 20 shows five fragments and solves, methods of the present disclosure may be used with any number of fragments and solvers. For example, the distributed computing system of FIG. 20 may be configured to perform any one or more of the operations described herein for at least about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000, 000, 70,000,000, 80,000,000, 90,000,000, 100,000,000, 200, 000,000, 300,000,000, 400,000,000, 500,000,000, 600,000, 000, 700,000,000, 800,000,000, 900,000,000, 1,000,000, 000 or more fragments. For example, the distributed computing system of FIG. 20 may be configured to perform any one or more of the operations described herein for at most about 1,000,000,000, 900,000,000, 80,000,000, 7000, 000,000, 600,000,000, 500,000,000, 400,000,000, 300,000, 000, 200,000,000, 100,000,000, 90,000,000, 80,000,000, 70,000,000, 60,000,000, 50,000,000, 40,000,000, 30,000, 000, 20,000,000, 10,000,000, 9,000,000, 8,000,000, 7,000, 000, 6,000,000, 5,000,000, 4,000,000, 3,000,000, 2,000,000, 1,000,000, 900,000, 800,000, 700,000, 600,000, 500,000, 400,000, 300,000, 200,000, 100,000, 90,000, 80,000, 70,000, 60,000, 50,000, 40,000, 30,000, 20,000, 10,000, 9,000, 8,000, 7,000, 6,000, 5,000, 4,000, 3,000, 2,000, 1,000, 900, 800, 700, 600, 500, 400, 300, 200, 100, 90, 80, 70, 60, 50, 40, 30, 20, 10, 9, 8, 7, 6, 5, 4, 3, 2, or 1 fragment(s). For example, the distributed computing system of FIG. 20 may be configured to perform any one or more of the operations described herein for a number of fragments that is within a range defined by any two of the preceding values.

FIG. 21 illustrates an example architecture 2100 of a distributed computing system comprising a problem dispatch at a remote endpoint, in accordance with some embodiments. In the illustrated embodiment, the problem may be sent from a client-side library to a first remote endpoint. The problem decomposition may be executed by code at a first remote endpoint. The problem decomposition may generate the subsystems and/or solver parameters. The first remote endpoint may forward the subsystems and/or solver parameters to the problem dispatch. The problem dispatch may send and receive to one or more second remote endpoints. For example, the problem dispatch may create and make REST calls to the one or more second remote endpoints, map the return values from the one or more second remote endpoints back to the input subsystems, and return the values back to the problem decomposition.

In the illustrated embodiment, the client code may be a thin library that contains versions of the electronic structure solvers and problem decompositions that make REST calls to a distributed computing system, for example, a cloud infrastructure. For example, the REST call may be made to a problem decomposition endpoint, which performs the problem decomposition and uses the problem dispatch to make calls to as many electronic structure solver endpoints. The problem decomposition remote call may return to the user in the same or similar way as a local call.

The architecture of FIG. 21 may be advantageous for several reasons. For example, a limited client-side library may minimize the amount of code located on a client machine. This may allow for lower performance client-side machines to execute code. This also may allow for easy distribution and updating of software. As a second example, more computationally intensive problem decomposition methods may be implemented by increasing the amount of code on provider-owned hardware. A provider may implement GPU machines or high-performance architectures that the user may not have direct access to for the problem decomposition.

As shown in FIG. 21, a target 2110 may comprise a portion of a client-side computing system 2150, e.g., a client-side library. A target 2110 may comprise a chemical system. A chemical system may comprise, for example, a molecule, a portion of a molecule, a fragment, an aggregate, etc. The architecture of FIG. 21 may limit the computation load on the client-side computing system.

The client-side computing system may be in communication with first one or more remote endpoints 2160. For example, the client-side computing system may transmit one or more of a targets, a molecule, a conformation, one or more fragments, and computational parameters to the first one or more remote endpoints. For example, the client-side computing system may receive one or more of a value corresponding to a solution to a problem (one or more energies, eigenvalues, structures, rates, etc.), information about a status of the computation, parameters relating to the progress of a computation, etc. The first one or more endpoints 2160 may comprise problem decomposer 2120 and problem dispatch 2140. Target 2110 may be decomposed into one or a plurality of fragments at the problem decomposer 2120. For example, target 2110 may be decomposed into fragments 2111, 2112, 2113, 2114, and 2115 at a problem decomposer. The problem decomposer may comprise instructions to perform any of the problem decomposition methods and/or techniques disclosed herein.

After decomposition, the fragments may be distributed to one or more electronic structure solvers 2131, 2132, 2133, 2134, and 2135 by problem dispatch 2140. Problem dispatch 2140 may create and/or implement the electronic structure solvers. Problem dispatch 2040 may pass parameters to one or more solvers, such as input parameters from a user. The problem dispatch may return outputs from the solver, such as for example, energies.

Problem dispatch 2140 may serve to communicate with the one or more solvers. In the illustrated embodiment, the one or more solver may comprise portions of one or more second endpoints 2170. The second endpoints may be local to one another (e.g., on the same machine, in the same physical location on a separate machine, etc.) or remote to one another. The second endpoints may comprise remote servers, a cloud network, portions of a distributed computing system, etc. The solver called by the problem dispatch may be specific to the problem type and/or fragment type. The problem dispatch may serve, in part, to distribute computational operations to reduce computation time and/or increase computational accuracy.

Fragments 2111, 2112, 2113, 2114, and 2115 may be encoded as fragments 2111', 2112', 2113', 2114', and 2115' on electronic structure solvers 2131, 2132, 2133, 2134, and 2135. Electronic structure solvers 2131, 2132, 2133, 2134, and 2135 may comprise one or more non-classical computing systems, one or more quantum computing systems, or one or more hybrid computing units, as described herein. Electronic structure solvers 2131, 2132, 2133, 2134, and 2135 may calculate energies $E^1$, $E^2$, $E^3$, $E^4$, and $E^5$ for fragments 2111', 2112', 2113', 2114', and 2115', respectively. Electronic structure solver 2131, 2132, 2133, 2134, and 2135 may pass energies $E^1$, $E^2$, $E^3$, $E^4$, and $E^5$ to problem dispatch 2140. The electronic structure solvers may receive and return fragments from the problem dispatch.

All or a portion of the plurality of fragments may be passed to the electronic structure solvers. The plurality of fragments may be passed to the electronic structure solvers in any order, sequentially or in parallel.

While the example illustrated in FIG. 21 shows five fragments and solves, methods of the present disclosure may be used with any number of fragments and solvers. For example, the distributed computing system of FIG. 21 may be configured to perform any one or more of the operations described herein for at least about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000, 000, 70,000,000, 80,000,000, 90,000,000, 100,000,000, 200, 000,000, 300,000,000, 400,000,000, 500,000,000, 600,000, 000, 700,000,000, 800,000,000, 900,000,000, 1,000,000, 000 or more fragments. For example, the distributed computing system of FIG. 21 may be configured to perform any one or more of the operations described herein for at most about 1,000,000,000, 900,000,000, 80,000,000, 7000, 000,000, 600,000,000, 500,000,000, 400,000,000, 300,000, 000, 200,000,000, 100,000,000, 90,000,000, 80,000,000, 70,000,000, 60,000,000, 50,000,000, 40,000,000, 30,000, 000, 20,000,000, 10,000,000, 9,000,000, 8,000,000, 7,000, 000, 6,000,000, 5,000,000, 4,000,000, 3,000,000, 2,000,000, 1,000,000, 900,000, 800,000, 700,000, 600,000, 500,000, 400,000, 300,000, 200,000, 100,000, 90,000, 80,000, 70,000, 60,000, 50,000, 40,000, 30,000, 20,000, 10,000, 9,000, 8,000, 7,000, 6,000, 5,000, 4,000, 3,000, 2,000, 1,000, 900, 800, 700, 600, 500, 400, 300, 200, 100, 90, 80, 70, 60, 50, 40, 30, 20, 10, 9, 8, 7, 6, 5, 4, 3, 2, or 1 fragment(s). For example, the distributed computing system of FIG. 21 may be configured to perform any one or more of the operations described herein for a number of fragments that is within a range defined by any two of the preceding values.

Computer Systems

Figure 10:
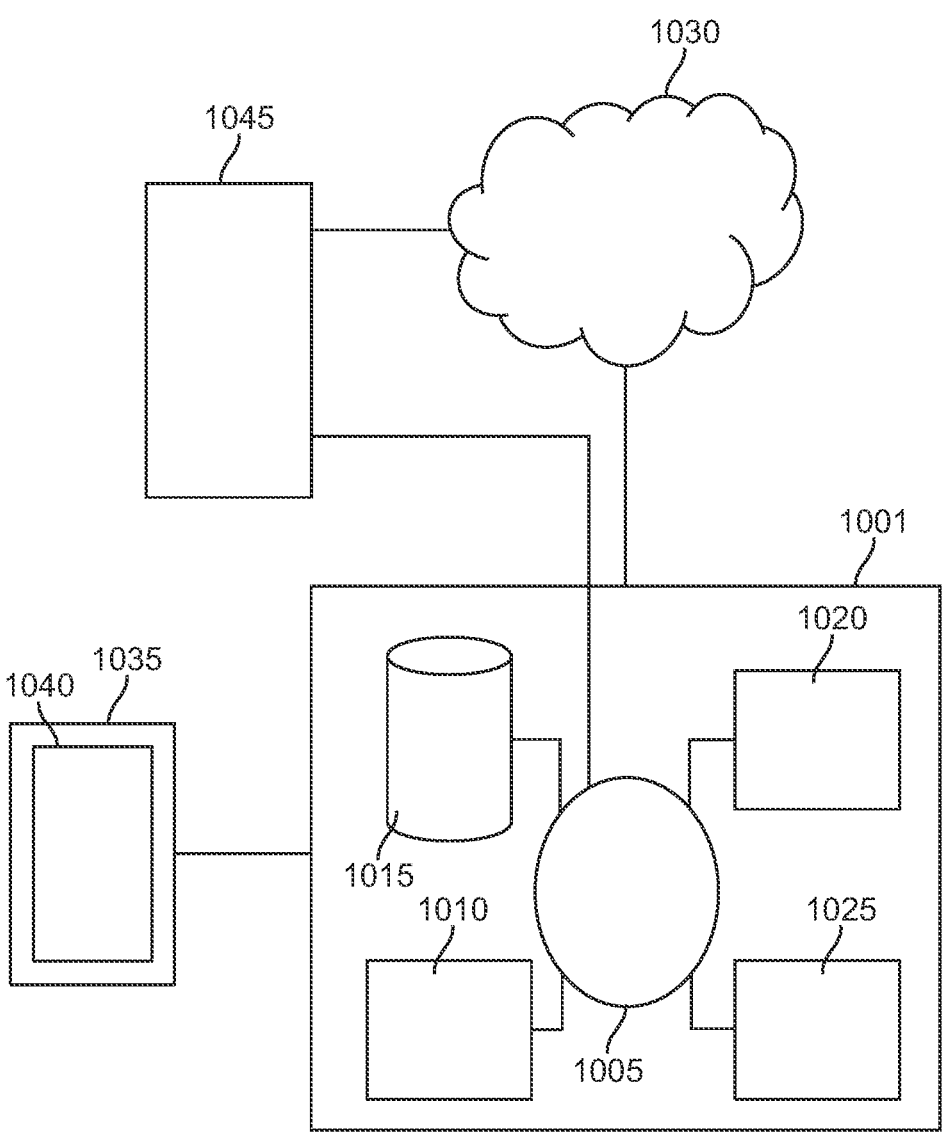
FIG. 10 illustrates a computer control system that is programmed or otherwise configured to implement methods provided herein.

The present disclosure provides computer systems that are programmed to implement methods of the disclosure. FIG. 10 illustrates a computer system 1001 that is programmed or otherwise configured to: determine an ensemble of confor- mations of a chemical system; decompose at least one conformation within the ensemble into a plurality of molecular fragments; determine, using a hybrid computing unit, quantum mechanical energies and/or electronic struc- tures of each of at least a subset of the plurality of molecular fragments; combine the determined quantum mechanical energies and/or electronic structures; and electronically out- put a report indicative of the combined quantum mechanical energies and/or electronic structures.

The computer system 1001 can regulate various aspects of methods and systems of the present disclosure, such as, for example, determining an ensemble of conformations of a chemical system; decomposing at least one conformation within the ensemble into a plurality of molecular fragments; determining, using a hybrid computing unit, quantum mechanical energies and/or electronic structures of each of at least a subset of the plurality of molecular fragments; combining the determined quantum mechanical energies and/or electronic structures; and electronically outputting a report indicative of the combined quantum mechanical ener- gies and/or electronic structures.

The computer system 1001 can be an electronic device of a user or a computer system that is remotely located with respect to the electronic device. The electronic device can be a mobile electronic device. The computer system 1001 includes a central processing unit (CPU, also "processor" and "computer processor" herein) 1005, which can be a single core or multi core processor, or a plurality of proces- sors for parallel processing. The computer system 1001 also includes memory or memory location 1010 (e.g., random- access memory, read-only memory, flash memory), elec- tronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communica- tion bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an internet and/or extranet, or an intranet and/or extranet that is in communication with the Internet.

The network 1030 in some cases is a telecommunication and/or data network. The network 1030 can include one or more computer servers, which can enable distributed com- puting, such as cloud computing. For example, one or more computer servers may enable cloud computing over the network 1030 ("the cloud") to perform various aspects of analysis, calculation, and generation of the present disclo- sure, such as, for example, determining an ensemble of conformations of a chemical system; decomposing at least one conformation within the ensemble into a plurality of molecular fragments; determining, using a hybrid comput- ing unit, quantum mechanical energies and/or electronic structures of each of at least a subset of the plurality of molecular fragments; combining the determined quantum mechanical energies and/or electronic structures; and elec- tronically outputting a report indicative of the combined quantum mechanical energies and/or electronic structures.

Such cloud computing may be provided by cloud computing platforms such as, for example, Amazon Web Services (AWS), Microsoft Azure, Google Cloud Platform, and IBM cloud. The network 1030, in some cases with the aid of the computer system 1001, can implement a peer-to-peer net- work, which may enable devices coupled to the computer system 1001 to behave as a client or a server. 'Cloud' services (including with one or more of the cloud platforms mentioned above) may also be used to provide data storage.

The CPU 1005 can execute a sequence of machine- readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and writeback.

The CPU 1005 can be part of a circuit, such as an integrated circuit. One or more other components of the system 1001 can be included in the circuit. In some cases, the circuit is an application specific integrated circuit (ASIC). The CPU 1005 may comprise one or more general purpose processors, one or more graphics processing units (GPUs), or a combination thereof.

The storage unit 1015 can store files, such as drivers, libraries, and saved programs. The storage unit 1015 can store user data, e.g., an ensemble of conformation of the chemical system, a plurality of decomposed molecular frag- ments, quantum mechanical energies and/or electronic struc- tures of molecular fragments, combined quantum mechani- cal energies and/or electronic structures of conformers, lists of molecular fragments with quantum mechanical energies and/or electronic structures, lists of conformers of a mol- ecule with combined quantum mechanical energies and/or electronic structures, and reports indicative of combined quantum mechanical energies and/or electronic structures (sometimes exchanging data with the memory). The com- puter system 1001 in some cases can include one or more additional data storage units that are external to the com- puter system 1001, such as located on a remote server that is in communication with the computer system 1001 through an intranet or the Internet.

The computer system 1001 can communicate with one or more remote computer systems through the network 1030. For instance, the computer system 1001 can communicate with a remote computer system of a user. Examples of remote computer systems include personal computers (e.g., portable PC), slate or tablet PC's (e.g., Apple® iPad, Sam- sung® Galaxy Tab), telephones, Smart phones (e.g., Apple® iPhone, Android-enabled device, Blackberry®), or personal digital assistants. The user can access the computer system 1001 via the network 1030. The user may control or regulate various aspects of methods and systems of the present disclosure, such as, for example, determining an ensemble of conformations of a chemical system; decomposing at least one conformation within the ensemble into a plurality of molecular fragments; determining, using a hybrid com- puting unit, quantum mechanical energies and/or electronic structures of each of at least a subset of the plurality of molecular fragments; combining the determined quantum mechanical energies and/or electronic structures; and elec- tronically outputting a report indicative of the combined quantum mechanical energies and/or electronic structures.

Methods as described herein can be implemented by way of machine (e.g., computer processor) executable code stored on an electronic storage location of the computer system 1001, such as, for example, on the memory 1010 or electronic storage unit 1015. The machine executable or machine readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory, Solid-state memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electro-magnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1035 that comprises a user interface (UI) 1040 for providing, for example, user selection of an ensemble of conformations of a chemical system; conformations within the ensemble for decomposing into a plurality of molecular fragments; at least a subset of the plurality of molecular fragments for determining quantum mechanical energies and/or electronic structures; and use of the Born-Oppenheimer approximation. Examples of UI's include, without limitation, a graphical user interface (GUI) and web-based user interface.

The computer system 1001 can include or be in communication with a non-classical computer (e.g., a quantum computer) 1045 for performing, for example, quantum algorithms (e.g., quantum mechanical energy and/or electronic structure calculations). The non-classical computer 1045 may be operatively coupled with the central processing unit 1005 and/or the network 1030 (e.g., the cloud).

Computer systems of the present disclosure may be as described, for example, in International Application No. PCT/CA2017/050709, U.S. application Ser. No. 15/486, 960, U.S. Pat. Nos. 9,537,953 and 9,660,859, each of which is entirely incorporated herein by reference.

Methods and systems of the present disclosure can be implemented by way of one or more algorithms. An algorithm can be implemented by way of software upon execution by the central processing unit 1005. The algorithm can, for example, determine an ensemble of conformations of a chemical system; decompose at least one conformation within the ensemble into a plurality of molecular fragments; determine, using a hybrid computing unit, quantum mechanical energies and/or electronic structures of each of at least a subset of the plurality of molecular fragments; combine the determined quantum mechanical energies and/or electronic structures; and electronically output a report indicative of the combined quantum mechanical energies and/or electronic structures.

Though described herein with respect to certain systems, such as hybrid or quantum-classical computing or computing hardware, a problem (such as a quantum chemistry problem or simulation) may be solved using a computing system comprising various types or combinations of systems, such as, for example, one or more classical computers, one or more non-classical computers (such as one or more quantum computers), or a combination of one or more classical computers and one or more non-classical computers. For instance, FIG. 15 illustrates examples of systems or combinations of systems that may be used to solve a problem, such as a quantum chemistry problem or simulation.

Further detail related to systems and methods for performing a quantum mechanical energy or electronic structure calculation for a chemical system may be found in U.S. Provisional Patent Application Ser. No. 62/593,060, filed Nov. 30, 2017 and PCT Application Serial Number PCT/

CA2018/051531, filed Nov. 30, 2018, which applications are entirely incorporated herein by reference for all purposes.

EXAMPLES

Example 1 (n-Heptane)

The correlation between the results of total quantum mechanical energy calculations with and without PD was investigated for different conformations of a compound. The simulation results for a fixed conformation with PD may not be within chemical accuracy. However, if this is due to systematic error, then comparing two erroneous results for different conformers of the same molecule can cancel this error out and may provide an accurate relative quantum mechanical energy difference between the two conformations of the molecule. Therefore, this approach can be used to accurately pick the best conformers (e.g., the most stable conformers) based on their total quantum mechanical energy values, even without having an optimally accurate estimation of total quantum mechanical energy for each individual conformer. Under this approach, more aggressive PD techniques (for example, DC with a relatively small buffer size) can be used to find the best conformers from an ensemble of available conformers. A more aggressive PD technique may yield smaller sub-molecules, which in turn may mean that fewer quantum resources may be required to conduct the experiment for a large molecule. This approach may thereby enable highly efficient and accurate predictions of the most stable conformers of a chemical system using quantum computing resources.

Figure 4:
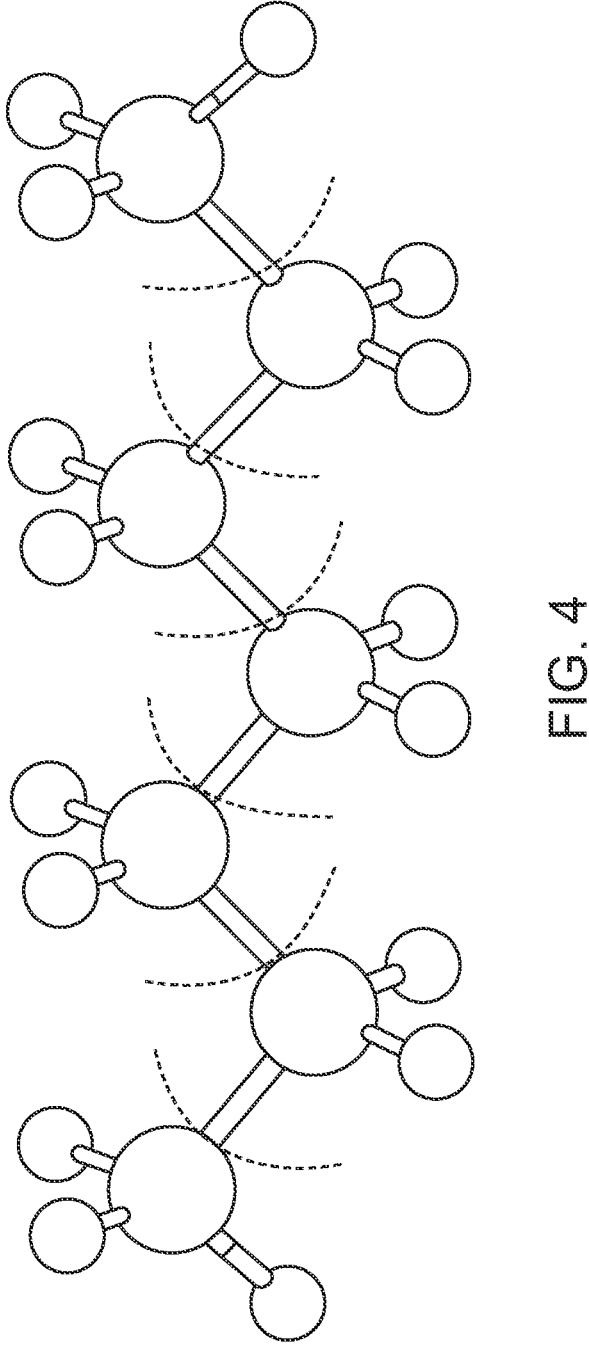
FIG. 4 is an example illustration of n-heptane, where the dotted lines indicate the bond detached atom in the fragment molecular orbital (FMO) fragmentation.

In this example, n-heptane was targeted, as shown in FIG. 4, where the dotted lines indicate the bond detached atom in the fragment molecular orbital (FMO) fragmentation. An ensemble of 40 conformations of n-heptane were generated by varying the four dihedral angles by 120 degrees (trans, gauche, gauche') and then removing symmetrically redundant conformations and high-energy conformations. In order to obtain the correlation between the total energies with and without problem decompositions (PD), CCSD was performed as a baseline reference and two problem decomposition methods, DC-CCSD and FMO-CCSD, were applied to this molecular system. Seven fragments were considered: 2 terminal $CH_3$ groups and 5 $CH_2$ groups. For DC, the buffer sizes of 3 Å, 4 Å, 5 Å, and 6 Å were examined. For FMO, the 2-body and 3-body expansions were examined. All calculations were performed using GAMESS-US with 6-31G basis set. The GAMESS quantum chemistry package was described in Schmidt et al., "General Atomic and Molecular Electronic Structure System," *Journal of Computational Chemistry,* 1993, 14, 1347-1363, which is hereby incorporated by reference in its entirety. The DC method was tested with a buffer size smaller than 3 Å, but the calculations for nearly all the conformers failed to converge to solutions.

Figure 5:
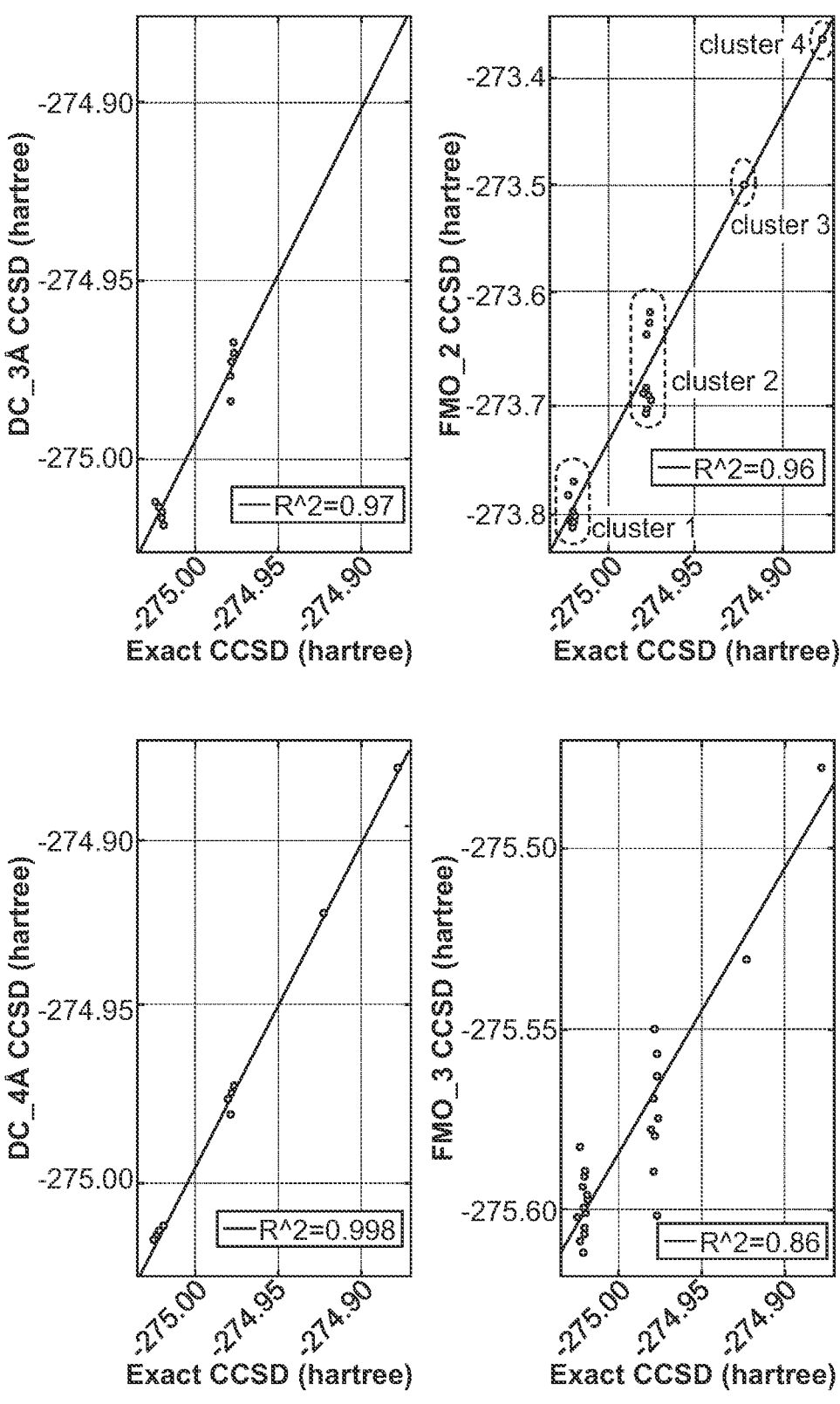
FIG. 5 is an example illustration of n-heptane, showing comparisons between results obtained by exact CCSD and divide-and-conquer CCSD (DC-CCSD), and between results obtained by exact CCSD and fragment molecular orbital CCSD (FMO-CCSD).

FIG. 5 illustrates comparisons (list of conformer quantum mechanical energy values) between the exact CCSD and the DC-CCSD results, and between the exact CCSD and the FMO-CCSD results, for n-heptane. Good correlation was obtained between the results from the exact CCSD and from CCSD with problem decomposition; the coefficients of determination $R^2$ were more than 0.96 except for FMO with 3-body expansion (FMO_3). Although DC-CCSD provides better results, the DC calculations sometimes experienced difficulty with converging to a solution. For n-heptane, FMO provided a solution for all the 40 conformers examined, while DC provided a solution for 35 and 36 conformers using 3 Å and 4 Å buffer sizes, respectively. It is also noted that the number of spin orbitals required to solve one fragment can differ in the case of DC calculations, depending on the conformation, because the buffer region is defined based on the distance from the center of the fragment.

Referring again to FIG. 5, several clusters of conformers were observed, for example, as indicated by the dotted circles in the top right panel. Here, why these clusters are observed is briefly discussed. First, the relation between the exact CCSD energy and the diameter of the minimum sphere that can accommodate the conformer was examined. This diameter can be considered as a measure of the structural compactness of the conformer. As shown in the middle panel in FIG. 6, the total quantum mechanical energy generally increases when the conformer becomes structurally compact due to steric repulsions. However, as seen, the diameter does not fully explain the clustering of the conformers in terms of total quantum mechanical energy. Next, the relation between the total quantum mechanical energy and the distance between the two outermost carbon atoms in a dihedral (1-4 distance) was examined. As illustrated by the right panel in FIG. 6, which illustrates the relation between the total quantum mechanical energy and the smallest 1-4 distance for each conformer, the 1-4 distance explains the clustering behavior very well. The 1-4 distance varies depending on the dihedral angles being trans, gauche, or gauche'. In the case of trans, the 1-4 distance becomes the longest. The dihedral angles of gauche and gauche' have the same 1-4 distance which is shorter than the 1-4 distance of trans, causing the higher (less stable) total quantum mechanical energy due to steric repulsions. This is the main source of the discretization of total energies and is the reason for the observation of clustering of conformers in terms of total quantum mechanical energy in the present molecular system.

Example 2 (3-Methylheptane)

Figure 7:
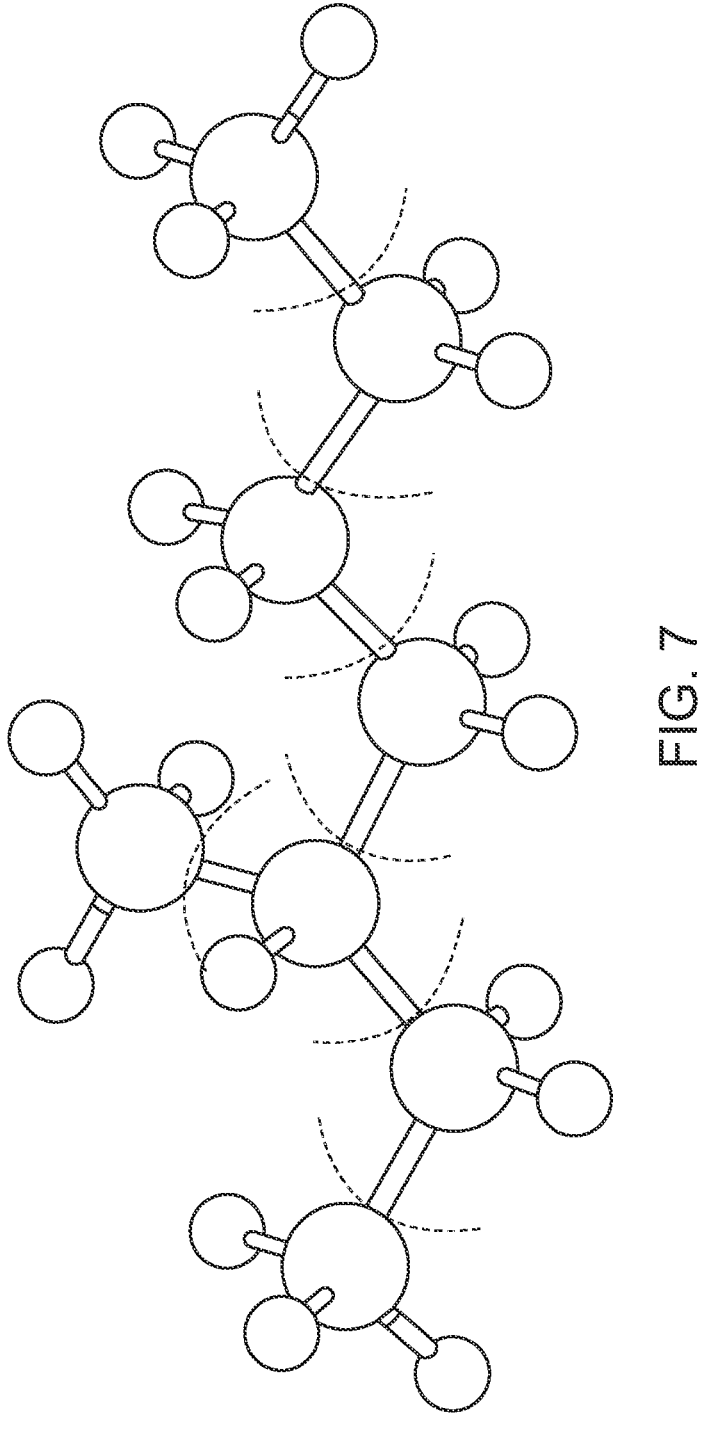
FIG. 7 is an example illustration of 3-methylheptane, where the dotted lines indicate the bond detached atoms in the fragment molecular orbital (FMO) fragmentation.

As observed, both FMO and DC work relatively well for a simple polymer system. Next, a diversified energy landscape was generated for examination by grafting one methyl group to the carbon atom at the "3" position of n-heptane, yielding 3-methylheptane, as shown in FIG. 7. The introduction of a methyl group to the "3" position renders the molecule asymmetric. As in the case of n-heptane, the ensemble of the conformations was generated for 3-methylheptane by varying the four dihedral angles by 120 degree (trans, gauche, gauche'), and 65 conformations were obtained after removing high-energy conformations.

Figure 8:
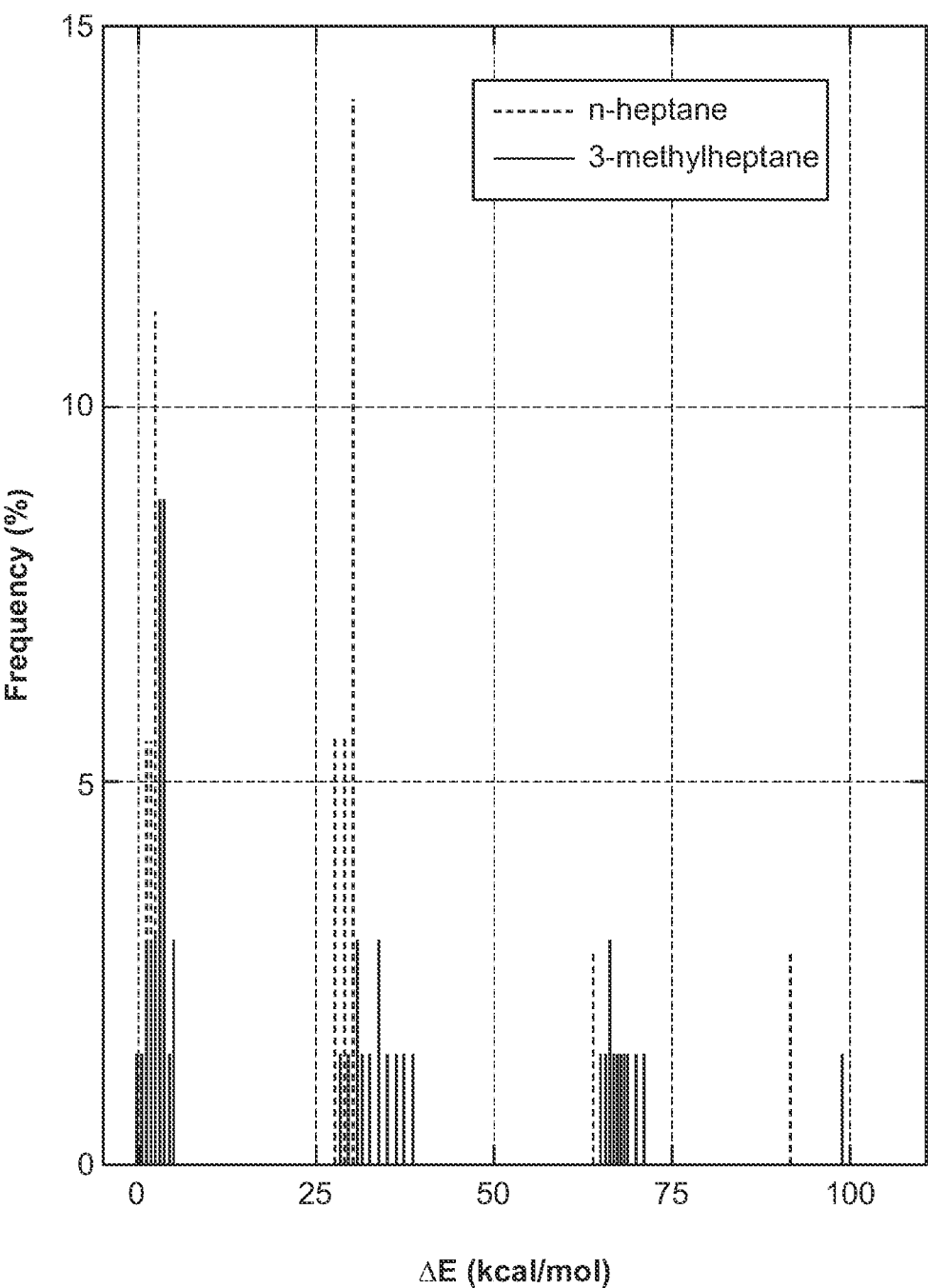
FIG. 8 illustrates the quantum mechanical energy distribution for n-heptane (blue) and 3-methylheptane (red).
Figure 9:
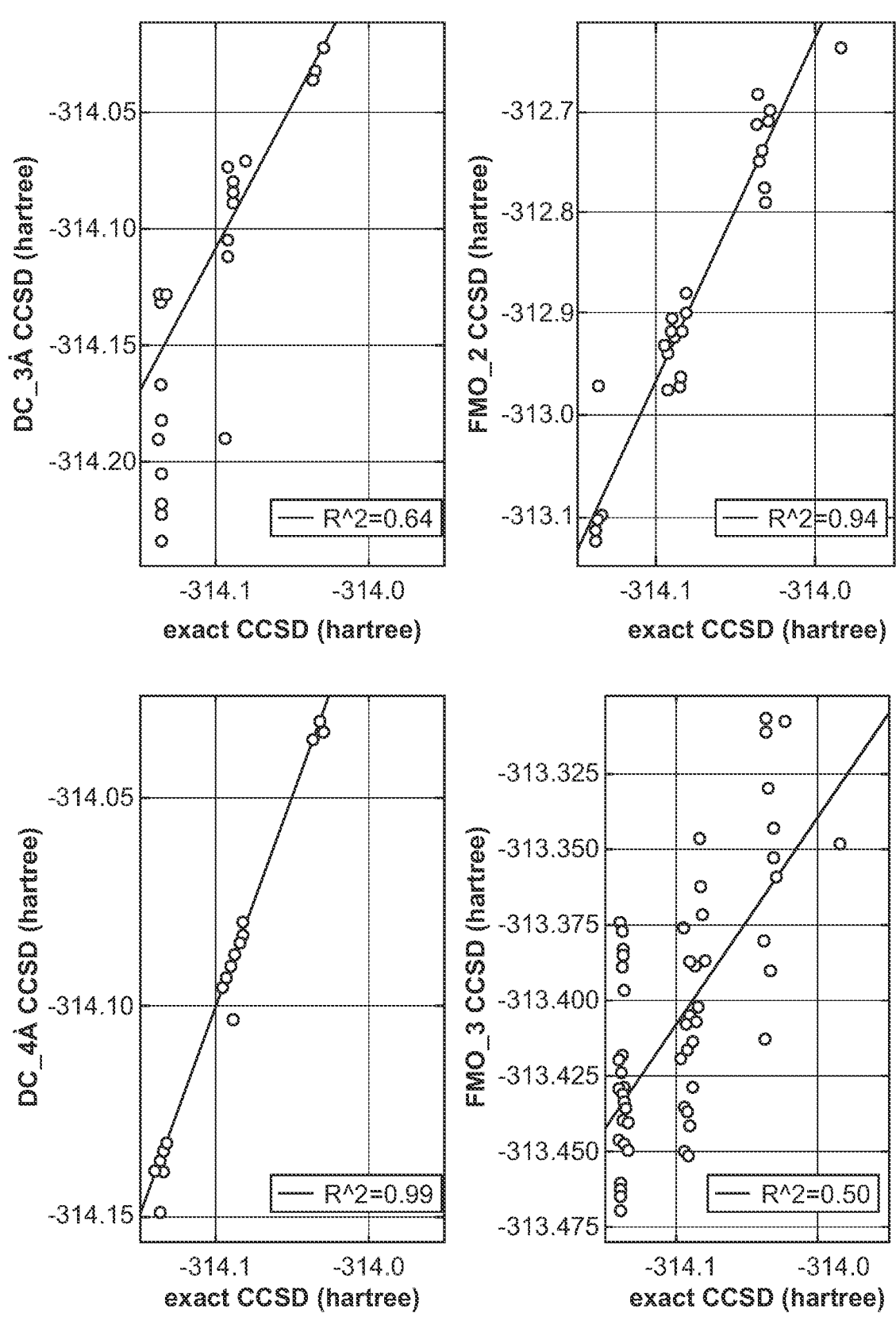
FIG. 9 is an example illustration of 3-methylheptane, showing comparisons between results obtained by exact CCSD and divide-and-conquer CCSD (DC-CCSD), and between results obtained by exact CCSD and fragment molecular orbital CCSD (FMO-CCSD).

FIG. 8 illustrates the quantum mechanical energy distribution (energies relative to the lowest one) obtained by CCSD to illustrate how one methyl group modulates and diversifies the quantum mechanical energy landscape from that of n-heptane. FIG. 9 illustrates comparisons (list of quantum mechanical conformer energy values) between the exact CCSD and the DC-CCSD results, and between the exact CCSD and the FMO-CCSD results, for 3-methylheptane. As shown, the FMO (2-body) approach on 3-methylheptane exhibits stable performance, with an $R^2$ of 0.94. Although the total energies obtained by DC with 3 Å buffer are somewhat closer to the exact CCSD than those obtained by FMO 2-body, the $R^2$ is lower than that of FMO. The DC approach on 3-methylheptane provides excellent agreement with exact CCSD when the buffer is increased to 4 Å. However, it is noted that DC again suffers slightly from the convergence failure issue. FMO provided a solution to all of the 65 conformers examined, while DC was able to provide a solution for 38 and 46 conformers with buffer sizes of 3 Å and 4 Å respectively.

Example 3 (Solver Fragments in DMET)

Example 3 is an example of DMET problem decomposition with a sequential implementation. Example 3 also shows an implementation in which the fragmentation is specified by a user. The user may pass a list of fragments, a specification of the molecule, and a specification of the mean field. The atoms of the molecules may be indexed by the order in which they return from a call to a quantum chemistry package, for example, the PySCF mol atom call. Each fragment may be defined by the indices of the atoms that it contains and, optionally, the type of solver that the user wants to solve the fragment with and/or any parameters that the solver may use.

If the user passes in the solver arguments with the fragment atoms, the fragment may be solved with the specified solver; otherwise, it may be solved with the instance that the problem decomposition object holds.

An example is shown below:
```
pd=DMETProblemDecomposition( )
solver=FCISolver( )
pd.electronic_structure_solver=solver
#Example specification: H4 molecule
H4_RING="""
    H 0.7071067811865476 0.0 0.0
    H 0.0 0.7071067811865476 0.0
    H −1.0071067811865476 0.0 0.0
    H 0.0 −1.0071067811865476 0.0
    """
mol=gto.Mole( )
mol.atom=H4_RING
mol.basis="3-21g"
mol.charge=0
mol.spin=0
mol.build( )
#Fragment specification, example
#Example, fragment 1 comprises first two atoms, solve
    with VQE solver
fragment1=([0,1], {"next_solver": "VQESolver",
    "solver_params":
        {"hardware_backend_type"="MicrosoftQSharp
        ParametricSolver",
        "ansatz_type": "MicrosoftQSharpParametricSolver-
        .Ansatze.UCCSD" }})
#Fragment 2, for example, solved with FCI solver if
    unspecified
fragment2=([0,1], None)
pd.simulate(mol, [fragment1, fragment2])
```

Example 4 (Solver Parameters for Fragments in DMET)

In some cases, the method to specify the fragments in DMET may not work for incremental methods. For example, in incremental methods, the fragments may be generated automatically, and they may not be defined by the atoms in the fragment, but rather by the size of the interactions. In this case, methods and systems disclosed herein may adapt the specification of the fragment so that instead of the list of atoms the first member of the tuple is increment name. A similar approach may be applied to increasingly higher order perturbation theory approaches.

For example:
```
#The one-body terms may be solved with the VQE solver
    with the parameters.
fragment1=("1-body", {"next_solver": "VQESolver",
    "solver_params":
        {"hardware_backend_type"="MicrosoftQSharp
        ParametricSolver",
        "ansatz_type": "MicrosoftQSharpParametricSolver-
        .Ansatze.UCCSD" }})
#The two-body terms may be solved with the default
    solver (e.g., FCI).
fragment2=("2-body", None)
pd.simulate(mol, [fragment1, fragment2])
```
The fragments that do not have a custom solver specified may use the default electronic structure solver that is held by the problem decomposition object, just as in the DMET case above.

Example 5 (FNO, Nested Solvers, and the Nested QEMIST)

Example 5 shows an example where the problem decomposition may not be specified by a user. Example 5 also shows an example implementation of a frozen natural orbitals (FNO) approach. A frozen natural orbital approach may be combined with coupled cluster (CC) methods and may increase speed of CC calculations. FNO approaches may reduce the virtual space of a correlated calculation by at least about half. For example, FNO approaches may reduce computational cost by identifying and removing combinations of virtual orbitals that do not contribute significantly to the CC energy. FNO may be implemented with problem decomposition methods disclosed herein. For example, FNO may be implemented before a problem decomposition, between a problem decomposition and an electronic structure solver, or simply in front of an electronic structure solver. For example, the REST calls sent to the distributed computing system, for example the cloud, may have a nested structure. In a nested structure, each request before the electronic structure solver may have a "next_solver" parameter that contains the call to the next step in the pipeline. Several examples follow:

FNO in Front of an Electronic Structure Solver

To use the FNO solver with an electronic structure solver, the user may specify the electronic structure solver and its parameters in the call to the FNO solver. The FNO solver may make the call to the next step in the pipeline and return its result after the nested solver executes.

For example:
```
next_solver_parameters={"next_solver": "VQESolver",
    "solver_params":
        {"hardware_backend_type"="MicrosoftQSharp
        ParametricSolver",
        "ansatz_type": "MicrosoftQSharpParametricSolver-
        .Ansatze.UCCSD" }}
fno=FNOSolver( )
fno.simulate(molecule, next_solver_parameters)
```
FNO Before DMET Before Electronic Structure Solvers To use DMET after FNO, the FNO solver may nest the DMET call above. Note that the dictionaries that contain the calls to the two fragments may be inserted into the dictionary of the full call.

For example:
```
H4_RING="""
    H 0.7071067811865476 0.0 0.0
    H 0.0 0.7071067811865476 0.0
```

```
    H −1.0071067811865476 0.0 0.0
    H 0.0 −1.0071067811865476 0.0
    """
mol=gto.Mole( )
mol.atom=H4_RING
mol.basis="3-21g"
mol.charge=0
mol.spin=0
mol.build( )
#Create the fragments
#The first one will be solved with VQE and contain the
    first two atoms.
fragment1=([0,1], {"next_solver": "VQESolver",
    "solver_params":
        {"hardware_backend_type"="MicrosoftQSharp
        ParametricSolver",
        "ansatz_type": "MicrosoftQSharpParametricSolver-
            .Ansatze.UCCSD" }})
fragment2=([2,3], {"next_solver": "FCISolver" })
full_pipeline={"next_solver":    "DMETProblemDecom-
    position",
    "solver_parameters": [fragment1, fragment2]}
```
DMET Before FNO Before Electronic Structure Solvers To use FNO on each fragment produced by DMET, one may flip the above call around, adding FNO as the next solver for each DMET fragment, then adding the next solver of the FNO call as an electronic structure solver. In this example, one can use FNO on some fragments, for example, the fragments which may be more computationally expensive.

For Example:
```
H4_RING="""
    H 0.7071067811865476 0.0 0.0
    H 0.0 0.7071067811865476 0.0
    H −1.0071067811865476 0.0 0.0
    H 0.0 −1.0071067811865476 0.0
    """
mol=gto.Mole( )
mol.atom=H4_RING
mol.basis="3-21g"
mol.charge=0
mol.spin=0
mol.build( )
es_solver1={"next_solver": "VQESolver",
    "solver_params":
        {"hardware_backend_type"="MicrosoftQSharp
        ParametricSolver",
        "ansatz_type": "MicrosoftQSharpParametricSolver-
            .Ansatze.UCCSD" }
fragment1=([0,1], {"next_solver": "FNOSolver", "solv-
    er_parameters": es_solver1})
es_solver2={"next_solver": "FCISolver" }
fragment2=([2,3], {"next_solver": "FNOSolver", "solv-
    er_parameters": es_solver2})
pd=DMETProblemDecomposition( )
pd.simulate(mol, [fragment1, fragment2])
```
While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention.

Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

What is claimed is:

1. A method for performing a quantum mechanical energy or electronic structure calculation for a chemical system, said method being implemented by a distributed computing system comprising at least three computers, wherein the at least three computers comprises a central classical computer and multiple electronic structure solvers, each electronic structure solver implementing one or more respective electronic structure solver types, each electronic structure solver type being defined by an algorithmic method, a hardware configuration, or both, the electronic structure solvers comprising quantum computing systems, non-classical computing systems, or hybrid computing units, said method comprising:

(a) decomposing, at the central classical computer, at least one conformation within an ensemble of conformations of said chemical system into a plurality of molecular fragments;

(b) generating, at the central classical computer and for each of one or more of said plurality of molecular fragments, a respective data structure for the molecular fragment, wherein the data structure specifies (i) a specification of the molecular fragment, (ii) an electronic structure solver type and (iii) solver parameters to be passed to an electronic structure solver of the specified type, the solver parameters comprising a hardware backend type and ansatz type to be used by the electronic structure solver of the specified type to determine quantum mechanical energies or electronic structures for the molecular fragment;

(c) identifying, at the central classical computer and for each of the one or more of said plurality of molecular fragments, an electronic structure solver included in the distributed computing system dedicated to the type specified in the data structure for the molecular fragment:

(d) dispatching the one or more of said plurality of molecular fragments and respective data structures from the central classical computer to the electronic structure solvers included in the distributed computing system of the types specified in the respective data structures;

(e) determining, by the electronic structure solvers included in the distributed system of the types specified in the respective data structures, using the hardware backend types specified in the respective data structures and according to the solver parameters in the respective data structures, quantum mechanical energies or electronic structures of at least a subset of said plurality of molecular fragments;

(f) combining, at the central classical computer said quantum mechanical energies or electronic structures determined in (e); and (g) electronically outputting a report indicative of said quantum mechanical energies or electronic structures combined in (f).

2. The method of claim 1, wherein the non-classical computers comprise at least one Hitachi Ising solver or a coherent Ising machine based on optical parameters and wherein the quantum computer systems comprise one or more members selected from the group consisting of: a quantum hardware device and a classical simulator of a quantum circuit.

3. The method of claim 1, wherein a quantum mechanical energy of said quantum mechanical energies comprises nuclear-nuclear repulsion energy.

4. The method of claim 1, further comprising providing an input to said central classical computer, said input comprising a set of atomic coordinates for said chemical system.

5. The method of claim 1, further comprising performing (a)-(f) for two or more conformations within said ensemble of conformations of said chemical system.

6. The method of claim 1, wherein (a) comprises applying one or more members selected from the group consisting of: a fragment molecular orbital (FMO) method, a divide-and-conquer (DC) method, a density matrix embedding theory (DMET) method, a density matrix renormalization group (DMRG) method, a tensor network, and a method of increments.

7. The method of claim 1, wherein (e) comprises: determining a fermionic Hamiltonian of a molecular fragment of said at least said subset of said plurality of molecular fragments; transforming said fermionic Hamiltonian into an equivalent qubit Hamiltonian; transforming said qubit Hamiltonian into a quantum circuit; and determining, using said quantum circuit, a quantum mechanical energy or electronic structure of said molecular fragment.

8. The method of claim 7, further comprising determining said quantum mechanical energy or electronic structure using one or more members selected from the group consisting of: a molecular Hamiltonian and an electronic Hamiltonian.

9. The method of claim 7, wherein transforming said fermionic Hamiltonian into an equivalent qubit Hamiltonian comprises transforming a fermionic operator of a Hamiltonian to a qubit operator.

10. The method of claim 1, further comprising, based on the quantum mechanical energies or electronic structures combined in (f), performing an ab initio molecular dynamics (AIMD) simulation of said chemical system.

11. The method of claim 10, wherein said AIMD simulation comprises:

prior to (a), obtaining an indication of a chemical system, said indication comprising coordinates of each particle of a plurality of particles in said chemical system and velocities of each particle in said chemical system; and subsequent to (f):

(i) determining, from said combined energy or electronic structure, a force on each particle in said chemical system;

(ii) updating said coordinates of said each particle in said chemical system and said velocities of said each particle in said chemical system; and (iii) electronically outputting a report indicative of said coordinates or said velocities.

12. The method of claim 11, wherein (i) comprises applying Jordan's quantum algorithm for numerical gradient estimation to said quantum mechanical energy or electronic structure.

13. The method of claim 11, wherein (ii) comprises applying one or more members selected from the group consisting of: a Verlet procedure, a velocity Verlet procedure, symplectic integration, Runge-Kutta integration, and Beeman integration.

14. The method of claim 1, further comprising dispatching one or more of said plurality of fragments to one or more remote endpoints and receiving said quantum mechanical energies or electronic structures from said one or more remote endpoints, wherein said one or more remote endpoints comprise portions of a cloud computing system.

15. The method of claim 14, wherein at least one of said one or more remote endpoints comprises a non-classical computer.

16. The method of claim 1, further comprising, prior to (a), receiving said at least one conformation from a client-side library and dispatching said at least one conformation to a first remote endpoint, dispatching one or more of said plurality of fragments to one or more remote second endpoints and receiving said quantum mechanical energies or electronic structures from said second one or more remote endpoints, and transmitting said report to said client-side library, and wherein at least one of (a) and (f) occur at said first remote endpoint.

17. A distributed computing system for performing a quantum mechanical energy or electronic structure calculation for a chemical system, the distributed computing system comprising a central classical computer operatively coupled to a memory, said memory comprising instructions for performing a quantum mechanical energy or electronic structure calculation for a chemical system, wherein the distributed computing system further comprises multiple electronic structure solvers, each electronic structure solver implementing one or more respective electronic structure solver types, each electronic structure solver type being defined by an algorithmic method, a hardware configuration, or both, the electronic structure solvers comprising quantum computing systems, non-classical computing systems, or hybrid computing units, wherein said distributed computing system is configured to at least:

(a) decompose, at the central classical computer, at least one conformation within an ensemble of conformations of said chemical system into a plurality of molecular fragments;

(b) generate, at the central classical computer and for each of one or more of said plurality of molecular fragments, a respective data structure for the molecular fragment, wherein the data structure specifies (i) a specification of the molecular fragment, (ii) an electronic structure solver type and (iii) solver parameters to be passed to an electronic structure solver of the specified type, the solver parameters comprising a hardware backend type and ansatz type to be used by the electronic structure solver of the specified type to determine quantum mechanical energies or electronic structures for the molecular fragment;

(c) identify, at the central classical computer and for each of the one or more of said plurality of molecular fragments, an electronic structure solver included in the distributed computing system of the type specified in the data structure for the molecular fragment;

(d) dispatch the one or more of said plurality of molecular fragments and respective data structures to electronic structure solvers included in the distributed computing system of the types specified in the respective data structures;

(e) determine, by the electronic structure solvers included in the distributed system of the types specified in the respective data structures, using the hardware backend types specified in the respective data structures and according to the solver parameters in the respective data structures, quantum mechanical energies or electronic structures of at least a subset of said plurality of molecular fragments;

(f) combine said quantum mechanical energies or electronic structures determined in (e); and (g) electronically output a report indicative of said quantum mechanical energies or electronic structures combined in (f).

\* \* \* \* \*